(12) United States Patent
Clark et al.

(10) Patent No.: US 7,629,463 B2
(45) Date of Patent: Dec. 8, 2009

(54) ORTHO-HETEROCYCLIC SUBSTITUTED ARYL AMIDES FOR CONTROLLING INVERTEBRATE PESTS

(75) Inventors: David Alan Clark, Landenberg, PA (US); Bruce Lawrence Finkelstein, Newark, DE (US); George Philip Lahm, Wilmington, DE (US); Thomas Paul Selby, Hockessin, DE (US); Thomas Martin Stevenson, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/004,395

(22) Filed: Dec. 19, 2007

(65) Prior Publication Data

US 2008/0132524 A1    Jun. 5, 2008

Related U.S. Application Data

(62) Division of application No. 10/483,117, filed as application No. PCT/US02/26968 on Aug. 12, 2002, now Pat. No. 7,375,232.

(60) Provisional application No. 60/312,440, filed on Aug. 15, 2001.

(51) Int. Cl.
*C07D 401/04*   (2006.01)
*A61K 31/4439*  (2006.01)

(52) U.S. Cl. .................................... 544/333; 514/341
(58) Field of Classification Search .................. 544/333
See application file for complete search history.

(56) References Cited

U.S. PATENT DOCUMENTS

| | | | |
|---|---|---|---|
| 4,321,371 A | 3/1982 | Parg et al. | |
| 5,602,126 A | 2/1997 | Barnette et al. | |
| 5,728,693 A | 3/1998 | Stevenson | |
| 5,804,588 A | 9/1998 | Dyke et al. | |
| 5,998,424 A | 12/1999 | Galemmo, Jr. et al. | |
| 6,020,357 A | 2/2000 | Pinto et al. | |
| 6,339,099 B1 * | 1/2002 | Lam et al. ............ | 514/378 |
| 6,403,620 B1 | 6/2002 | Galemmo, Jr. et al. | |
| 6,548,512 B1 | 4/2003 | Pinto et al. | |
| 6,602,826 B1 | 8/2003 | Andree et al. | |
| 6,602,895 B2 | 8/2003 | Galemmo, Jr. et al. | |
| 6,642,379 B1 | 11/2003 | Furuya et al. | |
| 6,806,286 B2 | 10/2004 | Walter et al. | |

FOREIGN PATENT DOCUMENTS

| | | |
|---|---|---|
| DE | 4428380 | 9/1994 |
| DE | 19840322 | 9/1998 |
| EP | 0455830 | 11/1990 |
| EP | 0919542 | 6/1999 |
| EP | 0946508 A1 | 10/1999 |
| EP | 1176140 | 1/2002 |
| EP | 1193254 | 4/2002 |
| EP | 09916251 B1 | 6/2005 |
| JP | 8092223 | 4/1996 |
| NL | 9202078 | 11/1992 |
| WO | WO93/11117 | 6/1993 |
| WO | WO93/16053 | 8/1993 |
| WO | WO94/12032 | 6/1994 |
| WO | WO95/09846 | 4/1995 |
| WO | WO96/16954 | 6/1996 |
| WO | WO96/36419 | 12/1996 |
| WO | WO97/10228 | 3/1997 |
| WO | WO97/30047 | 8/1997 |
| WO | WO98/26269 | 7/1998 |
| WO | WO98/39304 | 9/1998 |
| WO | WO98/57937 | 12/1998 |
| WO | WO99/41239 | 8/1999 |
| WO | WO00/47558 | 8/2000 |
| WO | WO01/00599 | 1/2001 |
| WO | WO01/02354 | 1/2001 |
| WO | WO01/32628 | 5/2001 |
| WO | WO01/49664 A1 | 7/2001 |
| WO | WO01/70671 | 9/2001 |

OTHER PUBLICATIONS

XP-002177117 + Suto, Mark J. et al., Tetrahedron Letters, vol. 36 No. 40. 1996, pp. 7213-7218, Elsevier Science Publishers, Amsterdam, NL.

* cited by examiner

*Primary Examiner*—Rebecca L Anderson
*Assistant Examiner*—Shawquia Young

(57) ABSTRACT

This invention pertains to compounds of Formula I, their N-oxides and suitable salts

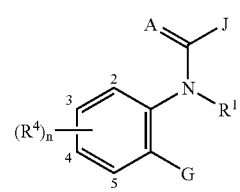

wherein A is O or S; G is a 5- or 6-membered heteroaromatic ring or a 5- or 6-membered nonaromatic heterocyclic ring optionally including one or two ring members selected from the group consisting of C(=O), SO or S(O)$_2$, each ring optionally substituted with from one to four R$^2$; each J is independently a phenyl ring, a 5- or 6-membered heteroaromatic ring or an aromatic 8-, 9- or 10-membered fused carbobicyclic or heterobicyclic ring system, wherein each ring or ring system is optionally substituted with from one to four R$^3$; and R$^1$, R$^2$, R$^3$, R$^4$ and n are as defined in the disclosure. A composition comprising a compound of Formula I, and a method for controlling an invertebrate pest comprising contacting the invertebrate pest or its environment with a biologically effective amount of a compound of Formula I are also disclosed.

9 Claims, No Drawings

ORTHO-HETEROCYCLIC SUBSTITUTED ARYL AMIDES FOR CONTROLLING INVERTEBRATE PESTS

BACKGROUND OF THE INVENTION

This invention relates to certain ortho-heterocyclic substituted aryl amides, their N-oxides, salts and compositions suitable for agronomic and nonagronomic uses, including those uses listed below, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

WO 01/00593 discloses 2-heterocyclyl benzamide derivatives of Formula ii as insecticides

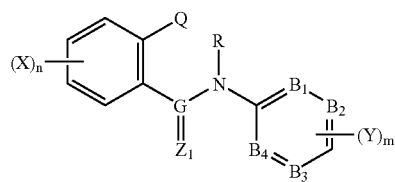

ii wherein, inter alia, R is H alkyl or alkoxycarbonyl; X is halo, CN, $NO_2$, $C_3$-$C_6$ (halo)cycloalkyl; Y is halo, CN, $NO_2$, —$C_3$-$C_6$ (halo)cycloalkyl; $Z_1$ is O or S; $B_1$ through $B_4$ are independently N or C; m is 1-5; and n is 0-4.

SUMMARY OF THE INVENTION

This invention pertains to compounds of Formula I, and N-oxides and salts thereof

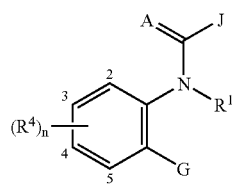

I wherein
A is O or S;
G is a 5- or 6-membered heteroaromatic ring or a 5- or 6-membered nonaromatic heterocyclic ring optionally including one or two ring members independently selected from the group consisting of C(=O), SO or $S(O)_2$, each ring optionally substituted with from one to four $R^2$;
each J is independently a phenyl ring, a 5- or 6-membered heteroaromatic ring or an aromatic 8-, 9- or 10-membered fused carbobicyclic or heterobicyclic ring system, wherein each ring or ring system is optionally substituted with from one to four $R^3$;
$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents independently selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or
$R^1$ is $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or C(=A)J;
each $R^2$ or $R^3$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or
each $R^2$ or $R^3$ is independently a phenyl, benzyl, benzoyl, phenoxy or 5- or 6-membered heteroaromatic ring, a naphthyl ring system, or an aromatic or nonaromatic 8-, 9- or 10-membered fused heterobicyclic ring system, each ring or ring system substituted with from one to three substituents independently selected from $R^5$; or
two $R^3$, when attached to adjacent carbon atoms, can be taken together as —$OCF_2O$—, —$CF_2CF_2O$—, or —$OCF_2CF_2O$—;
each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, or $C_3$-$C_6$ trialkylsilyl; or
each $R^4$ is independently a phenyl, benzyl or phenoxy ring, each ring substituted with from one to three substituents independently selected from $R^5$;
each $R^5$ is independently H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_7$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and
n is an integer from 1 to 4.

This invention also pertains to a method for controlling an invertebrate pest comprising contacting the invertebrate pest or its environment with a biologically effective amount of a compound of Formula I, an N-oxide thereof or a suitable salt of the compound (e.g., as a composition described herein). This invention also relates to such a method wherein the invertebrate pest or its environment is contacted with a biologically effective amount of a compound of Formula I, an N-oxide thereof or a suitable salt thereof, or a composition comprising the compound, N-oxide thereof or a suitable salt thereof, and a biologically effective amount of at least one additional compound or agent for controlling an invertebrate pest.

This invention also pertains to a composition for controlling an invertebrate pest comprising a biologically effective amount of a compound of Formula I, an N-oxide thereof or a suitable salt of the compound and at least one additional component selected from the group consisting of surfactants, solid diluents and liquid diluents. This invention also pertains to a composition comprising a biologically effective amount of a compound of Formula I, an N-oxide thereof or a suitable salt of the compound and an effective amount of at least one additional biologically active compound or agent.

DETAILS OF THE INVENTION

In the above recitations, "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Cycloalkyl" includes, for example, cyclopropyl, cyclobutyl, cyclopentyl and cyclohexyl. "Trialkylsilyl" includes $(CH_3)_3Si$, $(CH_3CH_2)_3Si$ and $[(CH_3)_3C](CH_3)_2Si$.

The term "aromatic" indicates that each of the ring atoms is essentially in the same plane and has a p-orbital perpendicular to the ring plane, and in which $(4n+2)\pi$ elections, when n is 0 or a positive integer, are associated with the ring to comply with Hückel's rule. The term "aromatic ring system" denotes fully unsaturated carbocycles and heterocycles in which at least one ring of a polycyclic ring system is aromatic. Aromatic carbocyclic ring or fused carbobicyclic ring systems includes fully aromatic carbocycles and carbocycles in which at least one ring of a polycyclic ring system is aromatic (e.g. phenyl, naphthyl and 1,2,3,4-tetrahydronaphthyl). The term "nonaromatic carbocyclic ring" denotes fully saturated carbocycles as well as partially or fully unsaturated carbocycles where the Hückel rule is not satisfied by the ring. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH3)C(=O)$.

The total number of carbon atoms in a substituent group is indicated by the "$C_i$-$C_j$" prefix where i and j are integers from 1 to 8. For example, $C_1$-$C_3$ alkylsulfonyl designates methylsulfonyl through propylsulfonyl.

In the above recitations, when a compound of Formula I contains a heterocyclic ring, all substituents are attached to this ring through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted" indicates that a group may be substituted or unsubstituted. The term "optionally substituted with from one to three substituents" and the like indicates that the group may be unsubstituted or from one to three of the available positions on the group may be substituted. When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form. Some compounds of this invention can exist as one or more tautomers, and all tautomeric forms of such compounds are part of the present invention. Accordingly, the compounds of the invention may be present as a mixture of tautomers or the individual tautomers.

The present invention comprises compounds selected from Formula I, N-oxides and agriculturally suitable salts thereof.

One skilled in the art will appreciate that not all nitrogen containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, Vol. 3, pp 18-19, A. J. Boulton and A. McKillop, Eds., Pergamon Press; M. R. Grimmett and B. R. T. Keene in *Advances in Heterocyclic Chemistry*, Vol. 43, pp 139-151, A. R. Katritzky, Ed., Academic Press; M. Tisler and B. Stanovnik in *Advances in Heterocyclic Chemistry*, Vol. 9, pp 285-291, A. R. Katritzky and A. J. Boulton, Eds., Academic Press; and G. W. H. Cheeseman and E. S. G. Werstiuk in *Advances in Heterocyclic Chemistry*, Vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, $R^1$ can be (among others) $C_1$-$C_6$ alkyl, $C_2$-$C_6$ alkenyl, $C_2$-$C_6$ alkynyl or $C_3$-$C_6$ cycloalkyl each optionally substituted with one or more substituents independently selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino. The term "optionally substituted" in connection with these $R^1$ groups refers to $R^1$ groups that are unsubstituted or have at least one non-hydrogen substituent. Examples of optionally substituted $R^1$ groups are those that are optionally substituted by replacement of a hydrogen on a carbon atom of the $R^1$ group with one or more (up to the total number of hydrogens available for replacement in any specific $R^1$ group) substituents independently selected from the substituents listed above. Although these substituents are listed in the examples above, it is noted that they do not need to be present since they are optional substituents. Of note are $R^1$ groups that are unsubstituted. Of note are $R^1$ groups substituted with from one to five substituents. Also of note are $R^1$ groups substituted with one substituent.

As noted above, each J is independently a phenyl ring, a 5- or 6-membered heteroaromatic ring or an aromatic 8-, 9- or 10-membered fused carbobicyclic or heterobicyclic ring system, wherein each ring or ring system is optionally substituted with from one to four $R^3$. The term "optionally substituted" in connection with these J groups refers to groups that are unsubstituted or have at least one non-hydrogen substituent. An example of phenyl optionally substituted with one to four $R^3$ is the ring illustrated as U-1 in Exhibit 1, wherein $R^v$ is $R^3$ and r is an integer from 1 to 4. Examples of aromatic 8-, 9- or 10-membered fused carbobicyclic ring system include a naphthyl group optionally substituted with 1 to 3 $R^3$ illustrated as U-85 in Exhibit 1 and a 1,2,3,4-tetrahydronaphthyl group illustrated as U-89 in Exhibit 1, wherein $R^v$ is $R^3$ and r is an integer from 1 to 4. Examples of 5- or 6-membered heteroaromatic rings optionally substituted with one to four $R^3$ include the rings U-2 through U-53 illustrated in Exhibit 1 wherein $R^v$ is $R^3$ and r is an integer from 1 to 4. Note that J-1 through J-4 below also denote 5- or 6-membered heteroaromatic rings. Note that U-2 through U-20 are examples of J-1, U-21 through U-35 and U-40 are examples of J-2, U-41 through U-48 are examples of J-3 and U-49 through U-53 are examples of J-4. Examples of aromatic 8-, 9- or 10-membered fused heterobicyclic ring systems optionally substituted with one to four $R^3$ include U-54 through U-84 illustrated in Exhibit 1 wherein $R^v$ is $R^3$ and r is an integer from 1 to 4.

Although $R^v$ groups are shown in the structures U-1 through U-89, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom of the U group. Note that when the attachment point on the U group is illustrated as floating, the U group can be attached to the remainder of Formula I through any available carbon of the U group by replacement of a hydrogen atom.

Exhibit 1

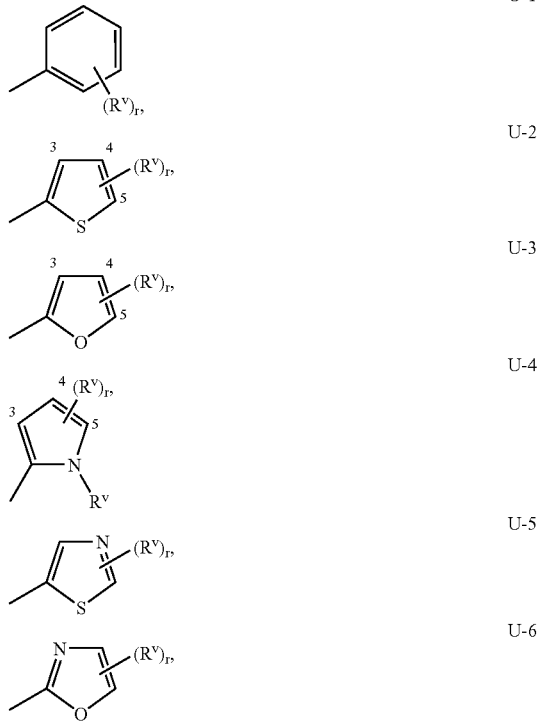

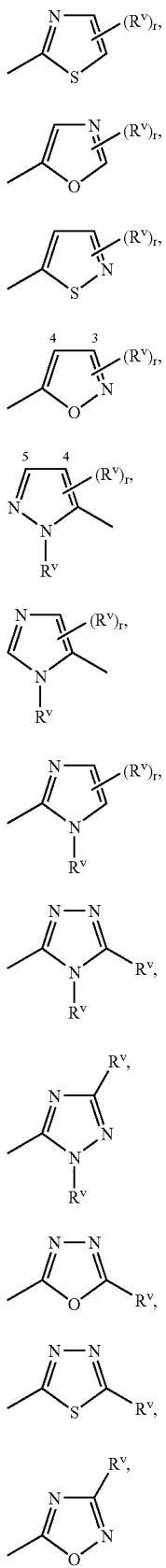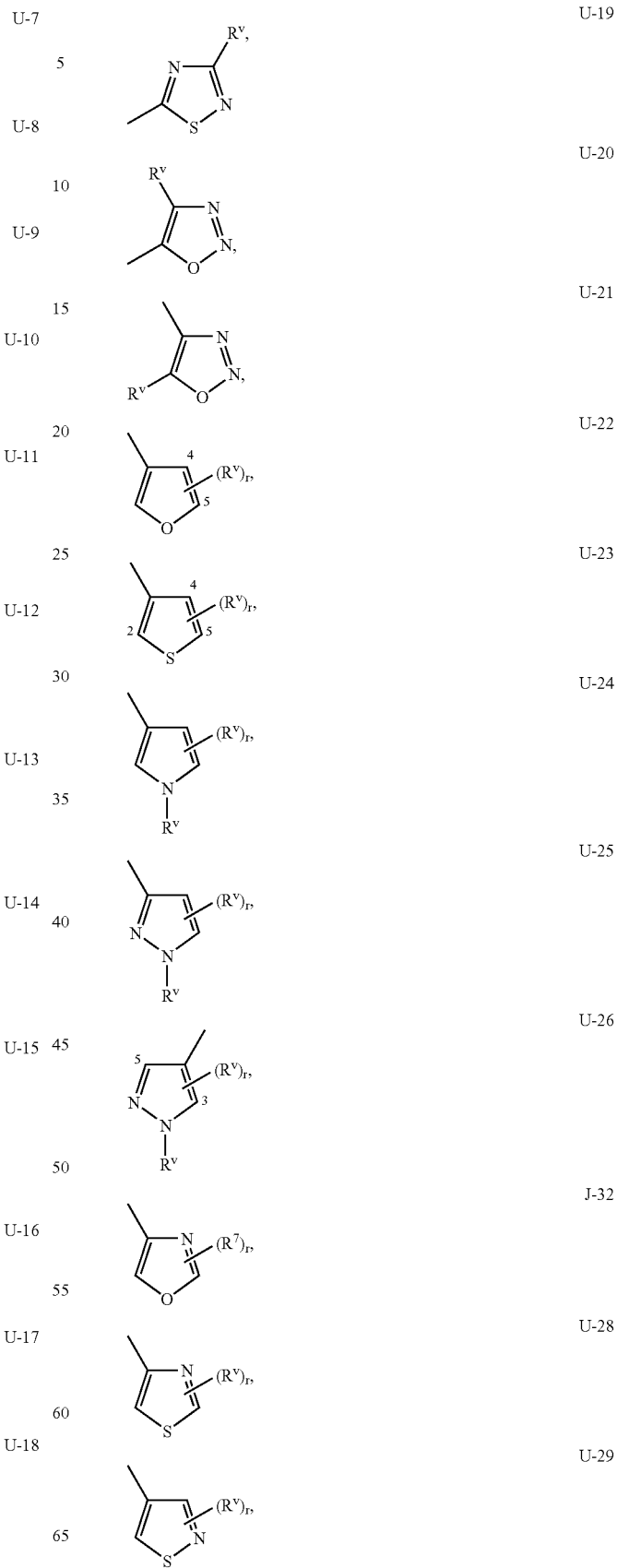

US 7,629,463 B2

-continued

U-30, U-31, U-32, U-33, U-34, U-35, U-36, U-37, U-38, U-39, U-40

-continued

U-41, U-42, U-43, U-44, U-45, U-46, U-47, U-48, U-49, U-50, U-51, U-52

-continued
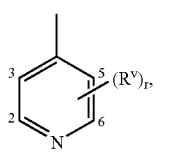 U-53
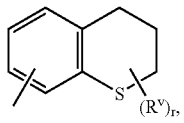 U-54
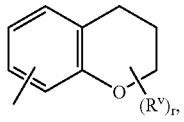 U-55
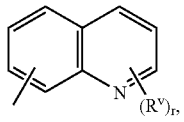 U-56
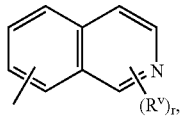 U-57
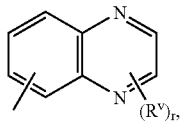 U-58
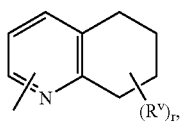 U-59
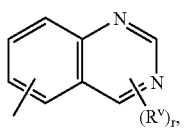 U-60
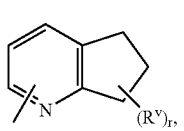 U-61
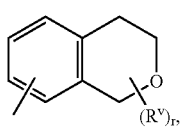 U-62
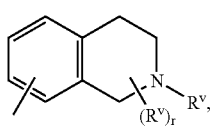 U-63
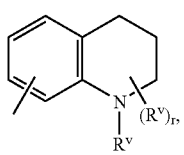 U-64
-continued
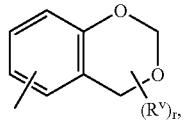 U-65
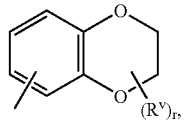 U-66
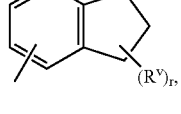 U-67
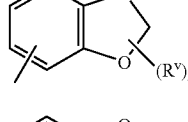 U-68
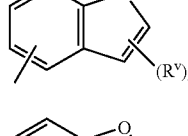 U-69
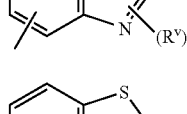 U-70
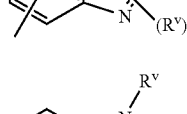 U-71
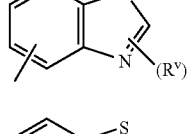 U-72
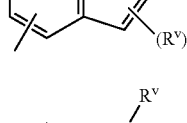 U-73
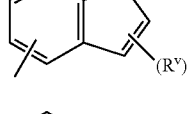 U-74
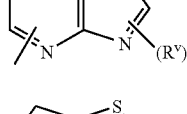 U-75
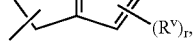 U-76

-continued

U-77 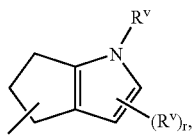
U-78 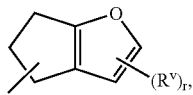
U-79 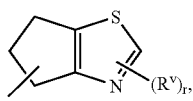
U-80 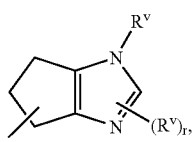
U-81 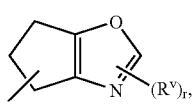
U-82 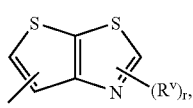
U-83 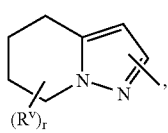
U-84 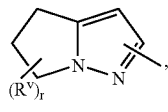
U-85 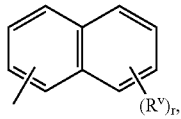
U-86 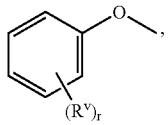
U-87 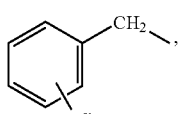
U-88 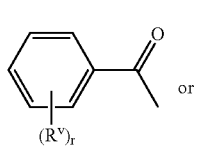

U-89 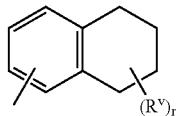

As noted above, G is a 5- or 6-membered heteroaromatic ring or a 5- or 6-membered nonaromatic heterocyclic ring optionally including one or two ring members independently selected from the group consisting of C(=O), SO or S(O)$_2$, each ring optionally substituted with from one to four R$^2$. The term "optionally substituted" in connection with these G groups refers to groups that are unsubstituted or have at least one non-hydrogen substituent. Examples of 5- or 6-membered heteroaromatic rings optionally substituted with one to four R$^2$ include the rings U-2 through U-53 illustrated in Exhibit 1 wherein R$^v$ is R$^2$ and r is an integer from 1 to 4. Note that G-1 through G-5 below also denote 5- or 6-membered heteroaromatic rings. Note that U-2 through U-20 are examples of G-1, U-21 through U-35 and U-40 are examples of G-2, U-36 through U-39 are examples of G-3, U-41 through U-48 are examples of U-4 and U-49 through U-53 are examples of G-5.

Examples of G as a 5- or 6-membered nonaromatic heterocyclic ring optionally including one or two ring members independently selected from the group consisting of C(=O), SO or S(O)$_2$, and optionally substituted with from one to four R$^2$, are illustrated in Exhibit 2. Note that when the attachment point on these G groups is illustrated as floating, the G group can be attached to the remainder of Formula I through any available carbon or nitrogen of the G group by replacement of a hydrogen atom. The optional substituents can be attached to any available carbon or nitrogen by replacing a hydrogen atom. Note that when G comprises a ring selected from G-31 through G-346 and G-39 through G-42, Q is selected from O, S or NR$^2$. Note that when G is G-10, G-12, G-14, G-16, G-23, G-24, G-25, G-30 through G-36 and G-39 through G-42 (when Q is NR$^2$), the nitrogen atoms that require substitution to fill their valence are substituted with H or R$^2$. Note that G-6, G-7 and G-43 below also denote 5- or 6-membered nonaromatic heterocyclic rings. Note that G-19, G-20 and G-23 are examples of G-6 when the attachment point is at the 2-position. Note that G-25, G-26 and G-27 are examples of G-7 when the attachment point is at the 2-position. Note that G-40 is an example of G-43 when the attachment point is at the 2-position.

Exhibit 2

G-8 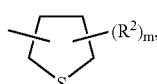

G-9 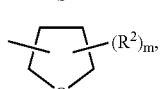

G-10 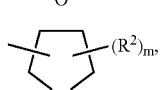

-continued
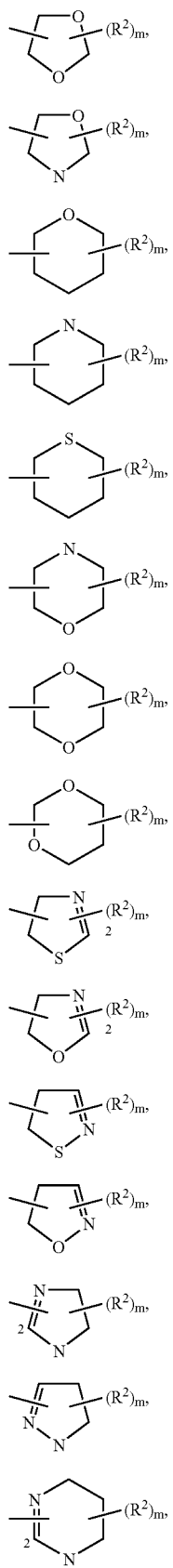
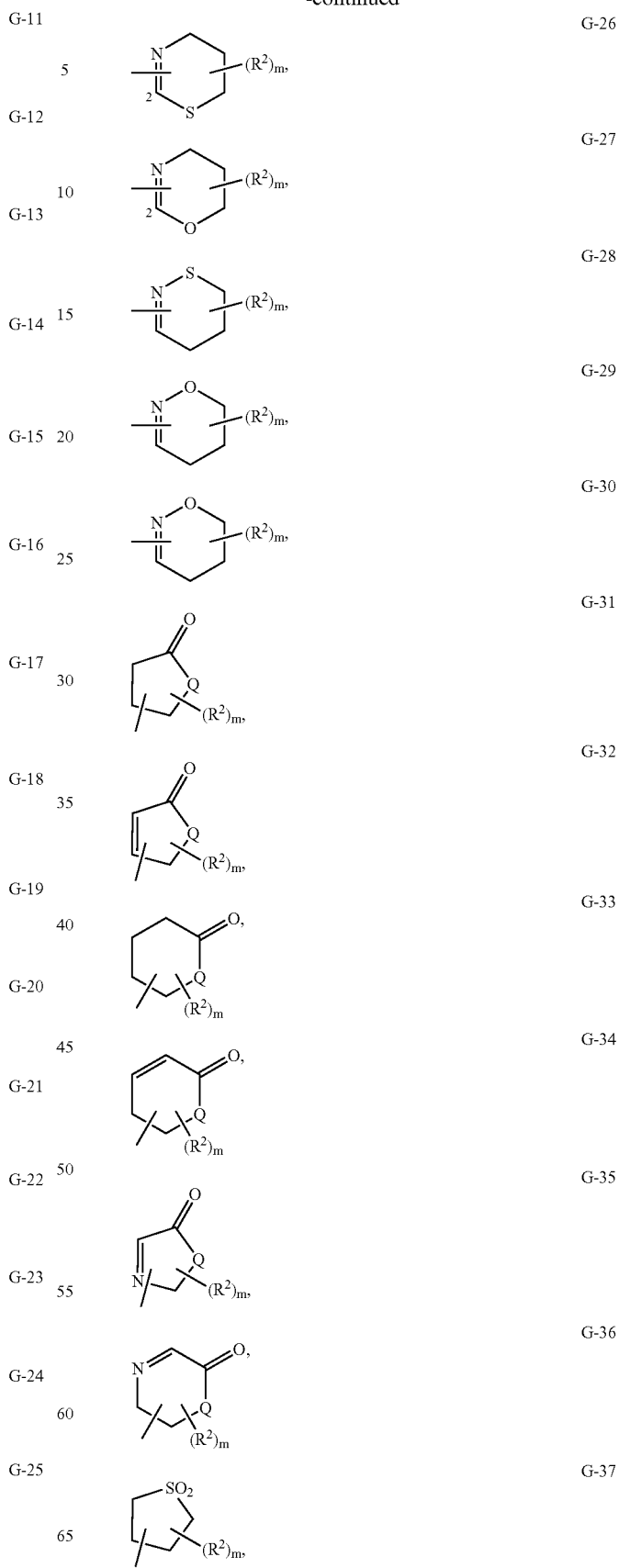

-continued

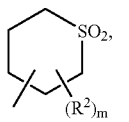
G-38

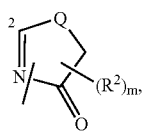
G-39

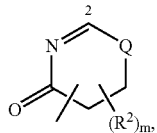
G-40

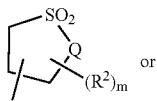
G-41 or

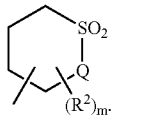
G-42

As noted above, each $R^2$ and each $R^3$ can be independently (among others) a phenyl, benzyl, benzoyl, phenoxy or 5- or 6-membered heteroaromatic ring, a naphthyl ring system, or an aromatic or nonaromatic 8-, 9- or 10-membered fused heterobicyclic ring system, each ring or ring system substituted with from one to three substituents independently selected from $R^5$. Examples of such $R^2$ and $R^3$ groups include the rings or ring systems illustrated as rings U-1 (phenyl), U-87 (benzyl), U-88 (benzoyl), U-86 (phenoxy), U-85 (naphthyl), U-2 through U-53 (5- or 6-membered heteroaromatic rings) and U-54 through U-84 (aromatic or nonaromatic 8-, 9- or 10-membered fused heterobicyclic ring systems) illustrated in Exhibit 1, wherein $R^v$ is $R^5$ and r is an integer from 1 to 3.

As noted above, each $R^4$ can be independently (among others) a phenyl, benzyl, or phenoxy ring, each ring substituted with from one to three substituents independently selected from $R^5$. Examples of such $R^4$ groups include the rings illustrated as rings U-1 (phenyl), U-87 (benzyl) and U-86 (phenoxy) illustrated in Exhibit 1, wherein $R^v$ is $R^5$ and r is an integer from 1 to 3.

Preferred compounds for reasons of better activity and/or ease of synthesis are:

Preferred 1. Compounds of Formula I wherein
  A is O;
  G is selected from the group consisting of G-1, G-2, G-3, G-4, G-5, G-6, G-7 and G-43, each G optionally substituted with from one to four $R^2$

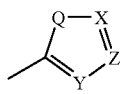
G-1

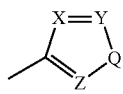
G-2

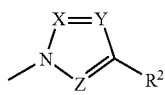
G-3

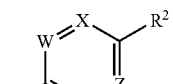
G-4

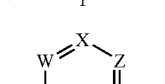
G-5

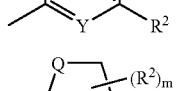
G-6

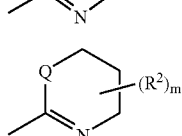
G-7

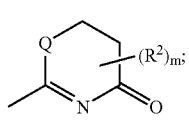
G-43

Q is O, S or $NR^2$;

W, X, Y and Z are independently N or $CR^2$, provided that in G-4 and G-5 at least one of W, X, Y or Z is N;

J is a phenyl ring or a 5- or 6-membered hetero aromatic ring selected from the group consisting of J-1, J-2, J-3 and J-4, each J ring optionally substituted with from one to three $R^3$

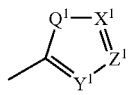
J-1

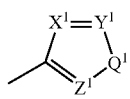
J-2

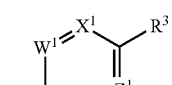
J-3

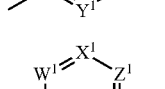
J-4

$Q^1$ is O, S or —$NR^3$;

$W^1, X^1, Y^1$ and $Z^1$ are independently N or $CR^3$, provided that in J-3 and J-4 at least one of $W^1, X^1, Y^1$ or $Z^1$ is N;

each R³ is independently H, C₁-C₄ alkyl, C₁-C₄ haloalkyl, halogen, CN, NO₂, C₁-C₄ alkoxy, C₁-C₄ haloalkoxy, C₁-C₄ alkylthio, C₁-C₄ alkylsulfinyl, C₁-C₄ alkylsulfonyl, C₁-C₄ haloalkylthio, C₁-C₄ haloalkylsulfinyl, C₁-C₄ haloalkylsulfonyl, C₂-C₄ alkoxycarbonyl, C₂-C₆ alkylaminocarbonyl or C₃-C₈ dialkylaminocarbonyl; or each R³ is independently a phenyl, benzyl or a 5- or 6-membered heteroaromatic ring, each ring optionally substituted with from one to three substituents independently selected from R⁵; or two R³, when attached to adjacent carbon atoms, can be taken together as —OCF₂O—, —CF₂CF₂O— or —OCF₂CF₂O—;

one R⁴ group is attached to remainder of Formula I at either the 2-position or 5-position of the phenyl ring, and said R⁴ is C₁-C₄ allyl, C₁-C₄ haloalkyl, halogen, CN, NO₂, C₁-C₄ alkoxy, C₁-C₄ haloalkoxy, C₁-C₄ alkylthio, C₁-C₄ alkylsulfinyl, C₁-C₄ alkylsulfonyl, C₁-C₄ haloalkylthio, C₁-C₄ haloalkylsulfinyl or C₁-C₄ haloalkylsulfonyl; and m is an integer from 0 to 4.

Preferred 2. Compounds of Preferred 1 wherein

R¹ is H or C₂-C₆ alkyl;

there is one R³ group attached to the J at the position ortho to the C=A moiety, and optionally one or two additional R³, and each R³ group is independently H, C₁-C₄ alkyl, C₁-C₄ haloalkyl, halogen, CN, NO₂, C₁-C₄ alkoxy, C₁-C₄ haloalkoxy, C₁-C₄ alkylthio, C₁-C₄ alkylsulfinyl, C₁-C₄ alkylsulfonyl, C₁-C₄ haloalkylthio, C₁-C₄ haloalkylsulfinyl, C₁-C₄ haloalkylsulfonyl, C₂-C₄ alkoxycarbonyl, C₂-C₆ alkylaminocarbonyl, C₃-C₈ dialkylaminocarbonyl; or a phenyl, benzyl, or 5- or 6-membered heteroaromatic ring, each ring optionally substituted with halogen, CN, NO₂, C₁-C₄ alkyl, C₁-C₄ alkenyl, C₂-C₄ alkynyl, C₃-C₆ cycloalkyl, C₁-C₄ haloalkyl, C₁-C₄ alkoxy or C₁-C₄ haloalkoxy; and n is 1 or 2.

Preferred 3. Compounds of Preferred 2 wherein J is a phenyl, pyrazole, pyrrole, pyridine or pyrimidine ring, each substituted with one R³ attached to the J at the position ortho to the C=A moiety and optionally one or two additional R³.

Preferred 4. Compounds of Preferred 3 wherein

R¹ is H;

one R⁴ is attached to remainder of Formula I at the 2-position of the phenyl ring ortho to the NR¹C(=A)J moiety and is selected from the group consisting of C₁-C₃ alkyl, CF₃, OCF₃, OCHF₂, S(O)ₚCF₃, S(O)ₚCHF₂ and halogen and optionally a second R⁴ is attached at the 4-position of the phenyl ring para to the NR¹C(=A)J moiety and is selected from the group consisting of halogen, C₁-C₃ alkyl and C₁-C₃ haloalkyl; and p is 0, 1 or 2.

Preferred 5. Compounds of Preferred 4 wherein

J is a pyrazole or pyrrole ring selected from the group consisting of J-5, J-6, J-7, J-8, J-9 and J-10, each ring substituted with R³ and optionally substituted with R⁶ and R⁷;

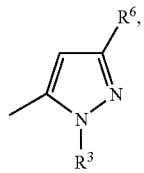

J-5

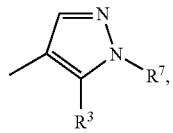

J-6

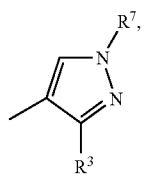

J-7

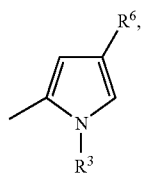

J-8

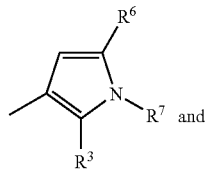

J-9 and

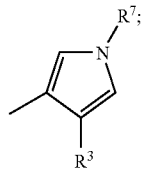

J-10

R³ is H, C₁-C₄ alkyl, C₁-C₄ haloalkyl, or

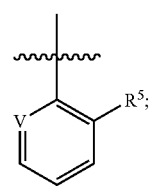

V is N; CH, CF, CCl, CBr or CI;

each R⁵ and each R⁶ is independently H, C₁-C₆ alkyl, C₃-C₆ cycloalkyl, C₁-C₆ haloalkyl, halogen, CN, C₁-C₄ alkoxy, C₁-C₄ haloalkoxy or C₁-C₄ haloalkylthio; and R⁷ is H, C₁-C₆ alkyl, C₁-C₆ haloalkyl, C₃-C₆ alkenyl, C₃-C₆ haloalkenyl, C₃-C₆ alkynyl or C₃-C₆ haloalkynyl.

Note that R⁶ and R⁷ are subsets of R³. Note that the F, Cl, Br or I atoms encompassed within V are a subset of R⁵. Note that the moiety illustrated for $R^3$ is attached to J via the bond highlighted with the wavy line.

Preferred 6. Compounds of Preferred 5 wherein V is N.

Preferred 7. Compounds of Preferred 5 wherein V is CH, CF, CCl or CBr.

Preferred 8. Compounds of Preferred 6 or Preferred 7 wherein
$R^5$ is H, $C_1$-$C_4$ alkyl, $C_1$-$C_4$ haloalkyl, halogen or CN;
$R^6$ is H, $CH_3$, $CF_3$, $OCH_2CF_3$, $OCHF_2$ or halogen; and
$R^7$ is $CH_2$, $CF_3$, $CHF_2$ or $CF_3$.

Preferred 9. Compounds of Preferred 8 wherein J substituted with $R^3$ and optionally substituted with $R^6$ is J-5; $R^5$ is Cl or Br; and $R^6$ is halogen, $OCH_2CF_3$, $OCHF_2$ or $CF_3$.

Preferred 10. Compounds of Preferred 8 wherein J substituted with $R^3$ and optionally substituted with $R^7$ is J-6; $R^9$ is Cl or Br; and $R^7$ is $CH_2CF_3$, $CHF_2$ or $CF_3$.

Preferred 11. Compounds of Preferred 8 wherein J substituted with $R^3$ and optionally substituted with $R^7$ is J-7; $R^9$ is Cl or Br; and $R^7$ is $CH_2CF_3$, $CHF_2$ or $CF_3$.

Preferred 12. Compounds of Preferred 8 wherein J substituted with $R^3$ and optionally substituted with $R^6$ is J-8; $R^5$ is Cl or Br; and $R^6$ is halogen, $OCH_2CF_3$, $OCHF_2$ or $CF_3$.

Preferred 13. Compounds of Preferred 8 wherein J substituted with $R^3$ and optionally substituted with $R^6$ and $R^7$ is J-9; $R^5$ is Cl or Br; and $R^6$ is halogen, $OCH_2CF_3$, $OCHF_2$ or $CF_3$; and $R^7$ is $CH_2CF_3$, $CHF_2$ or $CF_3$.

Preferred 14. Compounds of Preferred 8 wherein J substituted with $R^3$ and optionally substituted with $R^7$ is J-10; $R^9$ is Cl or Br; and $R^7$ is $CH_2CF_3$, $CHF_2$ or $CF_3$.

Of note are compounds of Preferred 6 through Preferred 14 wherein G is G-1, G-2, G-6 or G-43.

Most preferred is the compound of Formula I selected from the group consisting of:

1-(3-chloro-2-pyridinyl)-N-[2-(1H-imidazol-2-yl)-6-methylphenyl]-3-(trifluoromethyl)-1H-pyrazole-5-carboxamide, 1-(2-chloromethyl-N-[2-methyl-6-(1-methyl-1H-imidazol-2-yl)phenyl]-3-(trifluoromethyl)-1H-pyrazole-5-carboxamide, 1-(2-chlorophenyl)-N-[2-(4,5-dihydro-1-methyl-1H-imidazol-2-yl)-6-methylphenyl]-3-(trifluoromethyl)-1H-pyrazole-5-carboxamide, 1-(3-chloro-2-pyridinyl)-N-[2-(4,5-dihydro-1-methyl-1H-imidazol-2-yl)-6-methylphenyl]-3-(trifluoromethyl)-1H-pyrazole-5-carboxamide, N-[4-bromo-2-(4,5-dihydro-1-methyl-1H-imidazol-2-yl)-6-methylphenyl]-1-(2-chlorophenyl)-3-(trifluoromethyl)-1H-pyrazole-5-carboxamide, N-[4-bromo-2-(4,5-dihydro-1-methyl-1H-imidazol-2-yl)-6-methylphenyl]-1-(3-chloro-2-pyridinyl)-3-(trifluoromethyl)-1H-pyrazole-5-carboxamide, 1-(3-chloro-2-pyridinyl)-N-[2-(4,5-dihydro-2-oxazolyl)-6-methylphenyl]-3-(trifluoromethyl)-1H-pyrazole-5-carboxamide, and 1-(3-chloro-2-pyridinyl)-N-[2,4-dichloro-6-(4,5-dihydro-1H-imidazol-2-yl)phenyl]-3-(trifluoromethyl)-1H-pyrazole-5-carboxamide.

This invention also pertains to compositions for controlling an invertebrate pest comprising a biologically effective amount of a compound of Formula I, an N-oxide thereof or a suitable salt of the compound. Preferred compositions are those comprising compounds of Formula I as preferred in Preferred 1 through 14, and the specifically preferred compounds above.

This invention also pertains to methods for controlling an invertebrate pest comprising contacting the invertebrate pest or its environment with a biologically effective amount of a compound of Formula I, an N-oxide thereof or a suitable salt of the compound (e.g., as a composition described herein). Preferred methods are those comprising compounds of Formula I as preferred in Preferred 1 through 14, and the specifically preferred compounds above.

Of note are compounds of Formula Ie, their N-oxides or agriculturally suitable salts

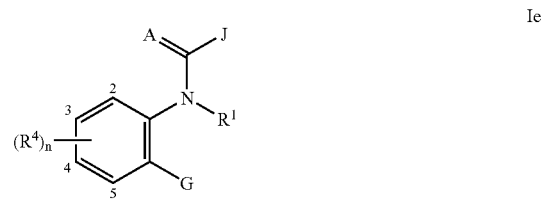

Ie wherein
A is O or S;

G is a 5- or 6-membered heteroaromatic ring or a 5- or 6-membered nonaromatic heterocyclic ring optionally including one or two ring members selected from the group consisting of C(=O), SO or $S(O)_2$, each ring optionally substituted with 1 to 4 $R^2$;

each J is independently a phenyl ring, a naphthyl ring system, a 5- or 6-membered heteroaromatic ring or an, aromatic 8-, 9- or 10-membered fused heterobicyclic ring system wherein each ring or ring system is optionally substituted with 1 to 4 $R^3$;

$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or C(=A)J;

each $R^2$ or $R^3$ is independently H, $C_1$-$C_6$ alkyl, $C_1$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl; or each $R^2$ or $R^3$ is independently a phenyl, benzyl, benzoyl, phenoxy, 5- or 6-membered heteroaromatic ring, a naphthyl ring system, or an aromatic or nonaromatic 8-, 9- or 10-membered fused heterobicyclic ring system, each ring or ring system optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $(R^3)_2$ when attached to adjacent carbon atoms can be taken together as —OCF$_2$O—, —CF$_2$CF$_2$O—, or —OCF$_2$CF$_2$O—;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, or $C_3$-$C_6$ trialkylsilyl; or each $R^4$ is independently phenyl, benzyl or phenoxy, each optionally substituted with $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and n is 1 to 4.

Also of note are selected compounds of Formula Ie:

Selection A. Compounds of Formula Ie wherein

A is O;

G is selected from the group consisting of G-1, G-2, G-3, G-4, G-5, G-6, G-7 and G-43, each G optionally substituted with 1 to 4 $R^2$

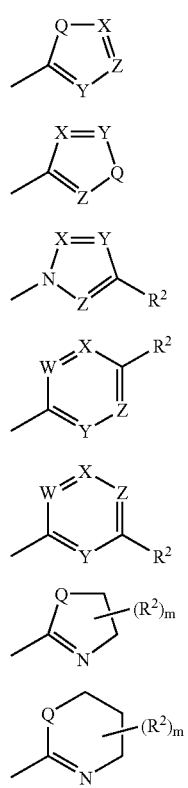

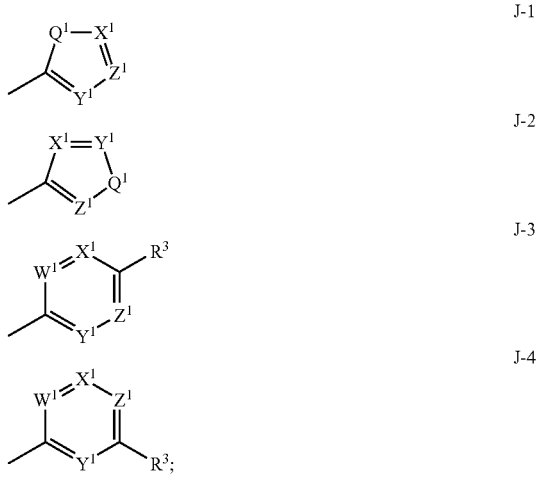

$Q^1$ is O, S or NR$^3$;

$W^1$, $X^1$, $Y^1$ and $Z^1$ are independently N or CR$^3$, provided that in J-3 and J-4 at least one of $W^1$, $X^1$, $Y^1$ or $Z^1$ is N; and m is 0 to 4.

Selection B. Compounds of Selection A wherein n is 1 to 2;

$R^1$ is H or $C_2$-$C_6$ alkyl;

one $R^3$ group is attached to the J at the position ortho to the C=A moiety, and said $R^3$ is $C_1$-$C_4$ alkyl, $C_1$-$C_4$ haloalkyl, halogen, CN, NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; $C_3$-$C_8$ dialkylaminocarbonyl or a phenyl, benzyl, or a 5- or 6-membered heteroaromatic ring, each ring optionally substituted with halogen, CN, NO$_2$, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_1$-$C_4$ alkoxy or $C_1$-$C_4$ haloalkoxy;

and an optional second $R^3$ group is independently $C_1$-$C_4$ allyl, $C_1$-$C_4$ haloalkyl, halogen, CN, NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; $C_3$-$C_8$ dialkylaminocarbonyl or a phenyl, benzyl, or a 5- or 6-membered heteroaromatic ring, each ring optionally substituted with halogen, CN, NO$_2$, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_1$-$C_4$ alkoxy or $C_1$-$C_4$ haloalkoxy.

Selection C. Compounds of Selection B wherein J is phenyl, pyrazole, pyrrole, pyridine or pyrimidine, each substituted with one $R^3$ attached to the J at the position ortho to the nitrogen atom linking J and C=A and a second optional $R^3$.

Selection D. Compounds of Selection C wherein $R^1$ is H; one $R^4$ is attached at the 2-position ortho to the $NR^1C(=A)J$ moiety and is selected from the group consisting of $C_1$-$C_3$ alkyl, $C_3$, $OCF_3$, $OCHF_2$, $S(O)_pCF_3$, $S(O)_pCHF_2$ and halogen and an optional second $R^4$ is attached at the 4-position para to the $NR^1C(=A)J$ moiety and is selected from the group consisting of halogen, $C_1$-$C_3$ alkyl and $C_1$-$C_3$ haloalkyl; and p is 0, 1 or 2.

Selection E. Compounds of Selection D wherein J is J-1; $Q^1$ is $NR^{3a}$; $X^1$ is N or CH; $Y^1$ is CH; $Z^1$ is $CR^{3b}$; $R^{3a}$ is phenyl or 2-pyridyl substituted with one or two substituents selected from halogen, $C_1$-$C_4$ alkyl, $C_1$-$C_4$ haloalkyl or $C_1$-$C_4$ haloalkoxy; and $R^{3b}$ is halogen or $CF_3$.

Selection F. Compounds of Selection D wherein G is G-1, G-2, G-6 or G-43.

One or more of the following methods and variations as described in Schemes 1-45 can be used to prepare the compounds of Formula I. The definitions of A, G, J, $R^1$, $R^2$, $R^3$, $R^4$, $R^5$, $R^6$, $R^7$, V and n in the compounds of Formulae 2-108 below are as defined above. Compounds of Formulae Ia-e, 2a-2b, 4a-v and 5a-y are various subsets of the compounds of Formula I, 2, 4 and 5, respectively. $R^{2a}$ through $R^{2e}$ are subsets of $R^2$ and $R^3(c)$ and $R^3(d)$ are subsets of $R^3$.

A typical procedure is described in Scheme 1 and involves coupling of an amine of Formula 2 with an acid chloride of Formula 3 in the presence of an acid scavenger or base to provide the compound of Formula Ia. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. The coupling can be run in a suitable inert solvent such as tetrahydrofuran, dioxane, diethylether or dichloromethane to afford the anilide of Formula Ia.

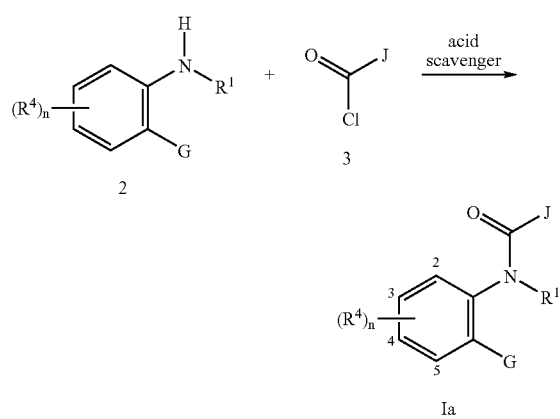

Scheme 1

An alternate procedure for the preparation of compounds of Formula Ia involves coupling of an amine of Formula 2 with an acid of Formula 4 in the presence of a dehydrating agent such as dicyclohexylcarbodiimide (DCC), 1,1'-carbonyldiimidazole, bis(2-oxo-3-oxazolidinyl)-phosphinic chloride or benzotriazol-1-yloxy-tris(dimethylamino)phosphonium hexafluorophosphate. The coupling can be run in a suitable inert solvent such as dichloromethane or N,N-dimethylformamide. Polymer supported reagents are again useful here, such as polymer-bound cyclohexylcarbodiimide. Synthetic procedures of Schemes 1 and 2 are only representative examples of useful methods for the preparation of Formula I compounds as the synthetic literature is extensive for this type of reaction.

Scheme 2

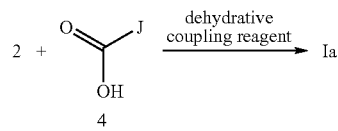

One skilled in the art will also realize that acid chlorides of Formula 3 may be prepared from acids of Formula-4 by numerous well-known methods. For example, acid chlorides of Formula 3 are readily made from carboxylic acids of Formula 4 by reacting the carboxylic acid 4 with thionyl chloride or oxalyl chloride in an inert solvent such as toluene or dichloromethane in the presence of a catalytic amount of N,N-dimethylformamide.

Heterocyclic substituted anilines of Formula 2a are typically available from the corresponding 2-nitrobenzenes of Formula 5 via catalytic hydrogenation of the nitro group (Scheme 3). Typical procedures involve reduction with hydrogen in the presence of a metal catalyst such as palladium on carbon or platinum oxide and in hydroxylic solvents such as ethanol and isopropanol. They can also be prepared by reduction with zinc in acetic acid. These procedures are well documented in the chemical literature. Substituted phenyl-heterocycles of Formula 5 can be made according to general methods such as those described in *Rodd's Chemistry of Organic Compounds: Heterocyclic Compounds*, Volume IV, parts C, F and IJ 1989, *Comprehensive Heterocyclic Chemistry*, Volumes 2, 3, 4, 5 and 6 (1984) and *Comprehensive Heterocyclic Chemistry II*, Volumes 3, 4, 5 and 6 1996, World Patent (PCT Int. Appl.) WO 98/56,789 (1998) and World Patent (PCT Int. Appl.) WO 96/06,096 (1996). $R^1$ substituents such as alkyl, substituted alkyl and the like can generally be introduced at this stage through known procedures including either direct alkylation or through the generally preferred method of reductive alkylation of the aniline. A commonly employed procedure is to combine the aniline 2a with an aldehyde in the presence of a reducing agent such as sodium cyanoborohydride to produce the Formula 2b compounds where $R^1$ is alkyl, alkenyl, alkynyl or substituted derivatives thereof.

Scheme 3

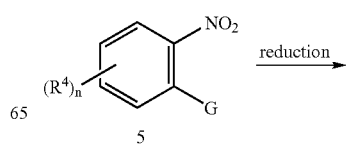

-continued

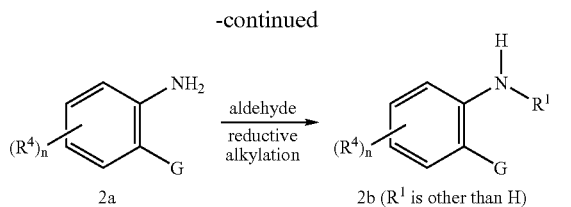

Scheme 4 shows that compounds of Formula Ib can be alkylated with a suitable alkylating agent such as an alkyl halide in the presence of a base such as sodium hydride or n-butyl lithium in all inert solvent such as tetrahydrofuran or N,N-dimethylformamide to afford anilides of Formula Ic wherein $R^1$ is other than hydrogen. This procedure is especially useful for preparing compounds of Formula Ic is which $R^1$ is alkyl, alkenyl or alkynyl.

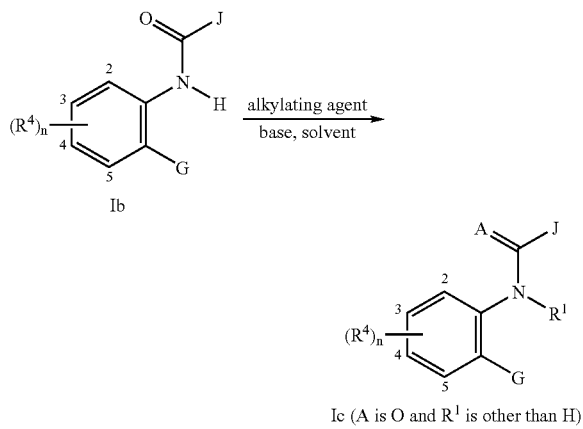

The preparation of thioanilides of Formula Id (where $R^1$ is hydrogen or other substitution as defined in the Summary of the Invention) is outlined in Scheme 5. Reacting an anilide of Formula Ia with phosphorous pentasulfide or Lawesson's Reagent in a suitable solvent such as pyridine at room temperature or on heating affords a thioanilide of Formula Id.

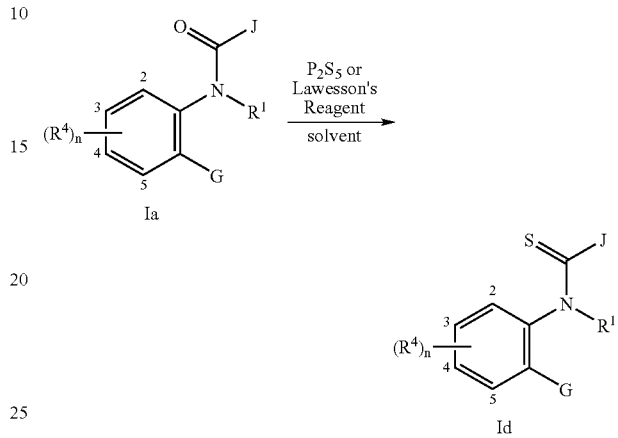

Benzoic acids of Formula 4a (compounds of Formula 4 wherein J is an optionally substituted phenyl ring) are well known in the art. Preparations of certain acids of Formula 4 are described in Schemes 6-11. A variety of heterocyclic acids and general methods for their synthesis may be found in World Patent Application WO 98/57397.

The synthesis of representative pyridine acids (4b) is depicted in Scheme 6. This procedure involves the known synthesis of pyridines from β-ketoesters and 4-aminobutenones (9). Substituent groups $R^3(c)$ and $R^3(d)$ include e.g. alkyl, haloalkyl, and optionally substituted aromatic and heteroaromatic rings.

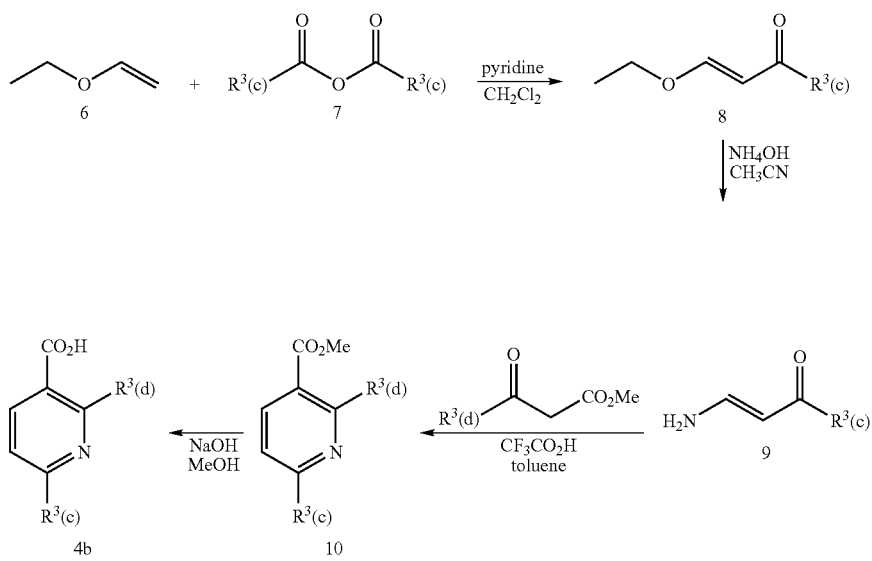

The synthesis of representative pyrimidine acids (4c) is depicted in Scheme 7. This procedure involves the known synthesis of pyrimidines from vinylidene-β-ketoesters (12) and amidines. Substituent groups $R^3$(c) and $R^3$(d) include e.g. alkyl haloalkyl, and optionally substituted aromatic and heteroaromatic rings.

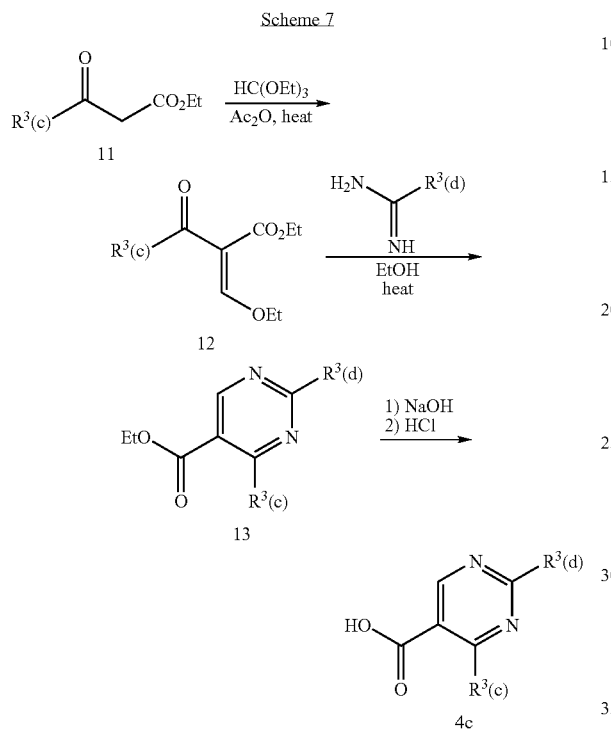

The synthesis of representative pyrazole acids (4d-4h) is depicted in Schemes 8-11. Pyrazoles 4d are described in Scheme 8. The synthesis of 4d in Scheme 8 involves as the key step introduction of the $R^3$(c) substituent via alkylation of the pyrazole. The alkylating agent $R^3$(c)-Lg (wherein Lg is a leaving group such as Cl, Br, I, sulfonates such as p-toluenesulfonate or methanesulfonate or sulfates such as —$SO_2OR^3$(c)) includes $R^3$(c) groups such as $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_1$-$C_6$ haloalkenyl, $C_2$-$C_6$ haloalkynyl, $C_3$-$C_6$ halocycloalkyl, $C_2$-$C_6$ alkylcarbonyl, $C_2$-$C_6$ alkoxycarbonyl, $C_3$-$C_8$ dialkylaminocarbonyl, $C_3$-$C_6$ trialkylsilyl; or phenyl, benzyl, benzoyl, 5- or 6-membered heteroaromatic ring or an aromatic 8-, 9- or 10-membered fused heterobicyclic ring system, each ring or ring system optionally substituted. Oxidation of the methyl group affords the pyrazole carboxylic acid. Some of the more preferred $R^3$(d) groups include haloalkyl and halogen.

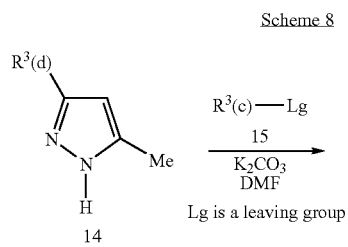

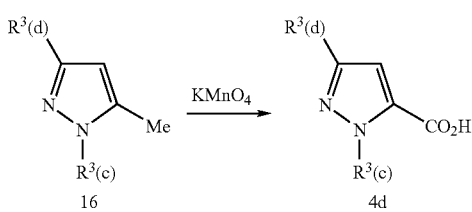

Syntheses of pyrazoles of Formula 4e are described in Scheme 9. These pyrazole acids may be prepared via metallation and carboxylation of pyrazoles of Formula 18 as the key step. The $R^3$(c) group is introduced in a manner similar to that of Scheme 8, i.e. via alkylation with an $R^3$(c) alkylating agent. Representative $R^3$(d) groups include e.g. cyano, and haloalkyl.

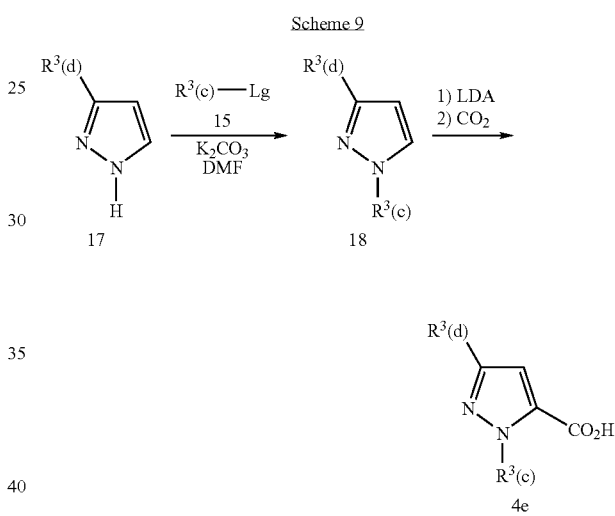

This procedure is particularly useful for preparing 1-(2-pyridinyl)pyrazolecarboxylic acids of Formula 4h, related to the preferred moiety J-5 as shown in Scheme 9a. Reaction of a pyrazole of Formula 17 with a 2,3-dihalopyridine of Formula 15a affords good yields of the 1-pyridylpyrazole of Formula 18a with good specificity for the desired regiochemistry. Metallation of 18a with lithium diisopropylamide (LDA) followed by quenching of the lithium salt with carbon dioxide affords the 1-(2-pyridinyl)pyrazolecarboxylic acid of Formula 4h.

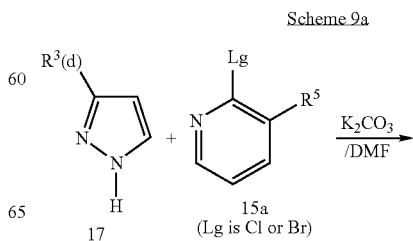

-continued

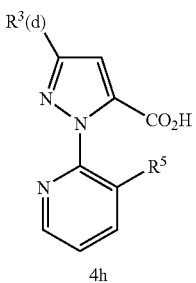
4h

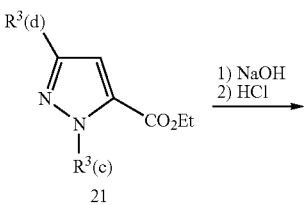
21    4f

Preparation of pyrazoles of Formula 4f is described in Scheme 10. These can be prepared via reaction of an optionally substituted phenyl hydrazine 19 with a ketopyruvate 20 to yield pyrazole esters 21. Hydrolysis of the ester affords the pyrazole acids 4f. This procedure is particularly useful for the preparation of compounds where $R^3(c)$ is optionally substituted phenyl and $R^3(d)$ is haloalkyl.

Scheme 10

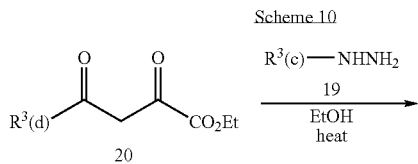

Pyrazole acids of Formula 4g are described in Scheme 11. These can be prepared via 3+2 cycloaddition of an appropriately substituted nitrilimine of Formula 22 with either substituted propiolates (23) or acrylates (26). Cycloaddition with acrylates requires additional oxidation of the intermediate pyrazoline to the pyrazole. Hydrolysis of the ester affords the pyrazole acids 4g. Preferred iminohalides for this reaction include the trifluoromethyl iminochloride (28) and the iminodibromide (29). Compounds such as 28 are known (*J. Heterocycl. Chem.* 1985, 22(2), 565-8). Compounds such as 29 are available by known methods (*Tetrahedron Letters,* 1999, 40, 2605). These procedures are particularly useful for the preparation of compounds where $R^3(c)$ is optionally substituted phenyl and $R^3(d)$ is haloalkyl or halogen.

Scheme 11

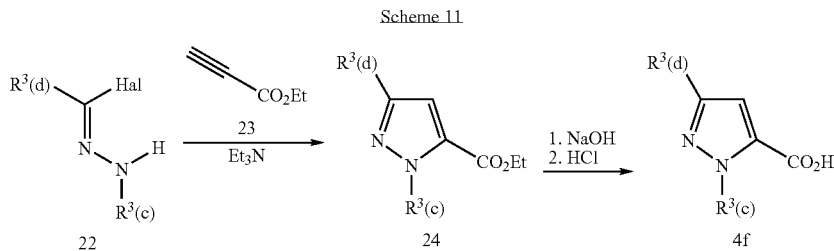

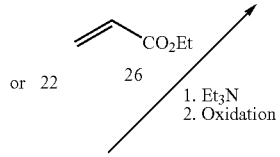

Hal is halogen

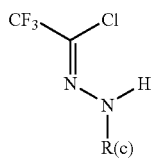 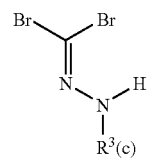
28    29

The preparation of substituted 2-nitrophenyloxazolines of formula 5a from 2-nitrobenzoic acids of Formula 30 is outlined in Scheme 12.

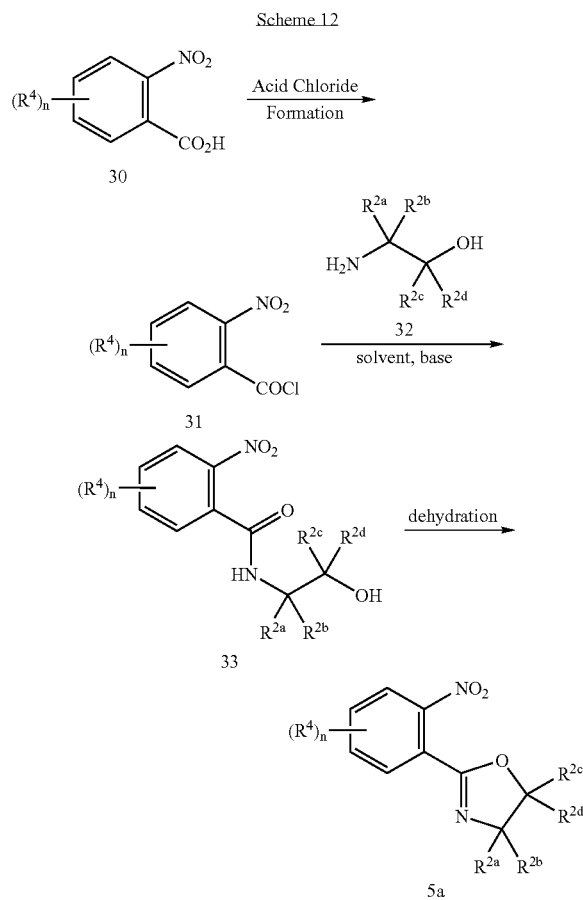

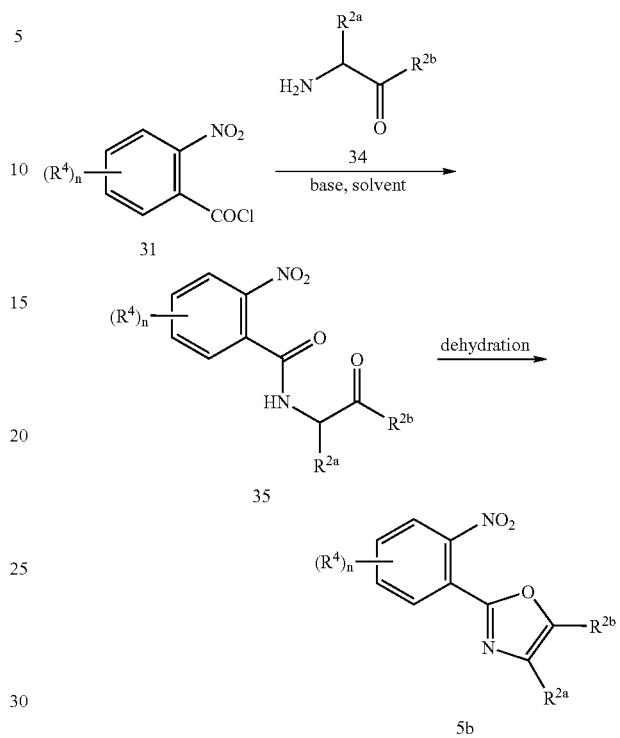

Conversion of nitrobenzoic acids of Formula 30 to acid chlorides of Formula 31 can be achieved by treating 30 with a suitable acid chloride-generating agent, e.g. thionyl chloride, oxalyl chloride, or phosgene, in a solvent such as toluene or dichloromethane. Treatment of acid chlorides of Formula 31 with substituted amino alcohols of Formula 32 in the presence of base, e.g. a tertiary amine or pyridine, in a solvent such as tetrahydrofuran, dioxane or dichloromethane affords nitrophenyl amides of Formula 33. Dehydration of amides of Formula 33 with an appropriate dehydrating agent, e.g., thionyl chloride, oxalyl chloride or phosphorus oxychloride, neat or in a solvent such as dichloromethane or toluene, affords intermediates of Formula 5a.

Scheme 13 outlines the preparation of substituted 2-nitrophenyloxazoles of Formula 5b from 2-nitrobenzoyl chlorides of Formula 31. Treatment of acid chlorides of Formula 31 with substituted aldoamines of Formula 34 (where $R^{2b}$ is hydrogen) or ketoamines of Formula 34 (where $R^{2b}$ is other than hydrogen) in the presence of base, e.g. a tertiary amine or pyridine, in a solvent such as tetrahydrofuran, dioxane or dichloromethane affords nitrophenyl aldoamides and ketoamides of Formula 35. Dehydration of aldoamides and ketoamides of Formula 35 with an appropriate dehydrating agent, e.g. thionyl chloride, oxalyl chloride or phosphorus oxychloride, neat or in a solvent such as dichloromethane or toluene, affords intermediates of Formula 5b.

The preparation of substituted 2-nitrophenyloxadiazoles of Formula 5c from 2-nitrobenzoyl chlorides of Formula 31 is outlined in Scheme 14. Treatment of acid chlorides of Formula 31 with a hydroxyformamidine of Formula 36 (where $R^{2b}$ is hydrogen) or hydroxyacetamidines of Formula 36 (where $R^{2b}$ is other than hydrogen) in the presence of base, e.g. a tertiary amine or pyridine, in a solvent such as tetrahydrofuran, dioxane or dichloromethane gives intermediates of Formula 37, which on dehydration with an appropriate dehydrating agent, e.g. thionyl chloride, oxalyl chloride or phosphorus oxychloride, neat or in a solvent such as dichloromethane or toluene, affords intermediates of Formula 5c.

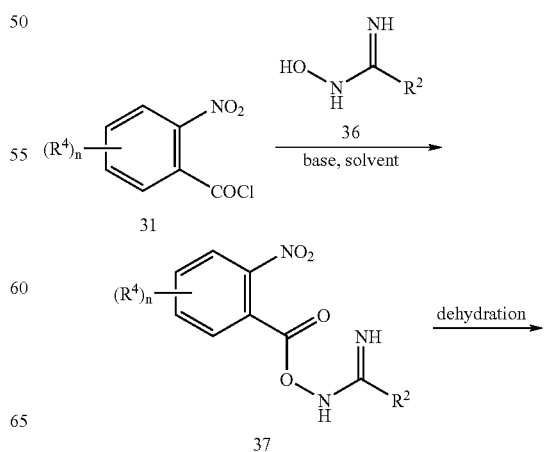

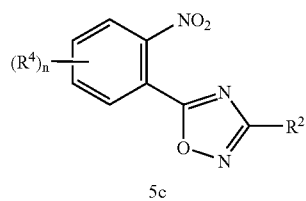

5c

The synthesis of substituted 2-nitrophenyloxadiazoles of Formula 5d from 2-nitrobenzoyl chlorides of Formula 31 is outlined in Scheme 15. Treatment of acid chlorides of Formula 31 with a hydrazides of Formula 38 in the presence of base, e.g., a tertiary amine or pyridine, in a solvent such as tetrahydrofuran, dioxane or dichloromethane gives intermediates of Formula 39, which on dehydration with an appropriate dehydrating agent) e.g., thionyl chloride, oxalyl chloride or phosphorus oxychloride, neat or in a solvent such as dichloromethane or toluene, affords intermediates of Formula 5d.

Scheme 15

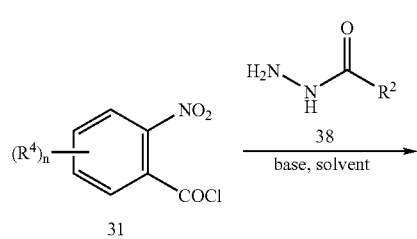

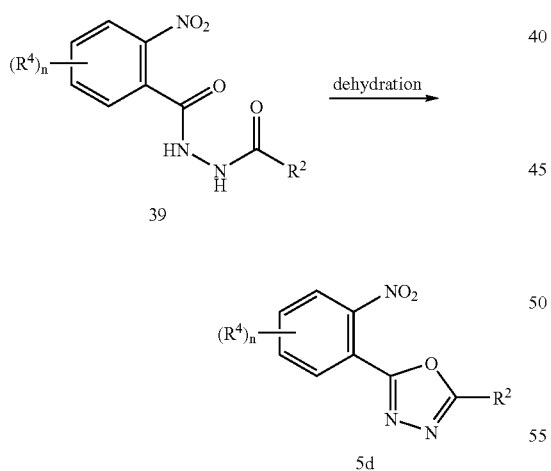

The preparation of substituted 2-nitrophenyloxadiazoles of Formula 5e from 2-nitrobenzonitriles of Formula 40 is outlined in Scheme 16. Treatment benzonitriles of Formula 40 with hydroxylamine in all appropriate solvent, e.g. methanol, ethanol or acetonitrile, gives hydroxybenzamidines of Formula 41. Reaction of 41 with anhydrides of the formula $(R^2CO)_2O$ in a solvent such as tetrahydrofuran, dioxane or pyridine affords intermediates of Formula 5e.

Scheme 16

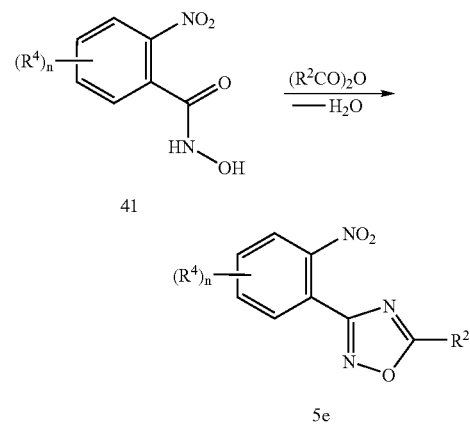

The preparation of substituted 2-nitrophenylthiazoles of Formula 5f from 2-nitrobenzonitriles of Formula 40 is outlined in Scheme 17. Treatment of benzonitriles of Formula 40 with hydrogen sulfide in a solvent such as pyridine gives thiobenzamides of Formula 42. Reaction of 42 with α-haloaldehydes or α-haloketones of Formula 43 in a solvent such as a lower alkyl alcohol, with a base such as trialkylamine, affords intermediates of Formula 5f.

Scheme 17

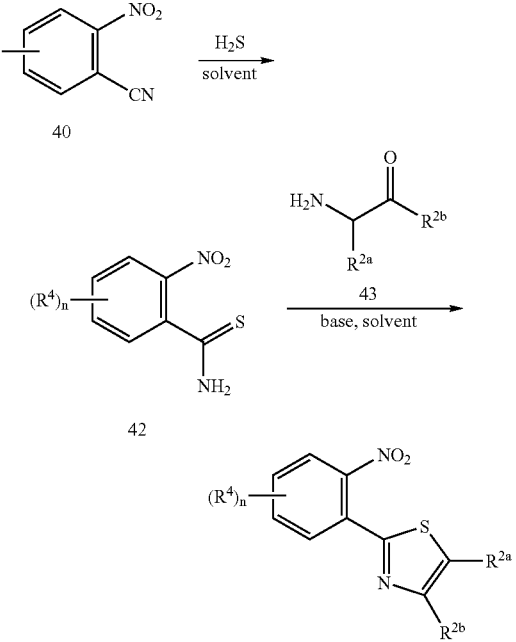

Hal is halogen

Scheme 18 outlines the preparation of substituted 2-nitrophenylthiadiazoles of Formula 5g from 2-nitrobenzoyl chlorides of Formula 31. Treatment of acid chlorides of Formula 31 with hydrazine in a solvent such as ethanol, tetrahydrofuran, dioxane or acetonitrile gives hydrazides of Formula 44, which on reaction with phosphorous pentasulfide or Lawesson's reagent in a solvent such as pyridine provides thiohydrazides of Formula 45. Reaction of 45 with anhydrides of the formula $(R^2CO)_2O$ in an appropriate solvent such as tetrahydrofuran, dioxane, acetonitrile or pyridine gives intermediates of Formula 5g.

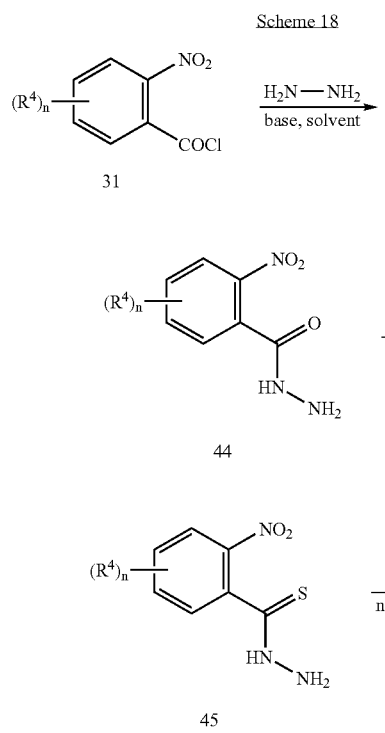

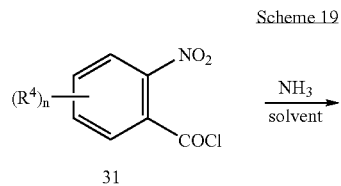

Scheme 19 outlines the preparation of substituted 2-nitrophenyltriazoles of Formulae 5h and 5i from 2-nitrobenzoyl chlorides of Formula 31.

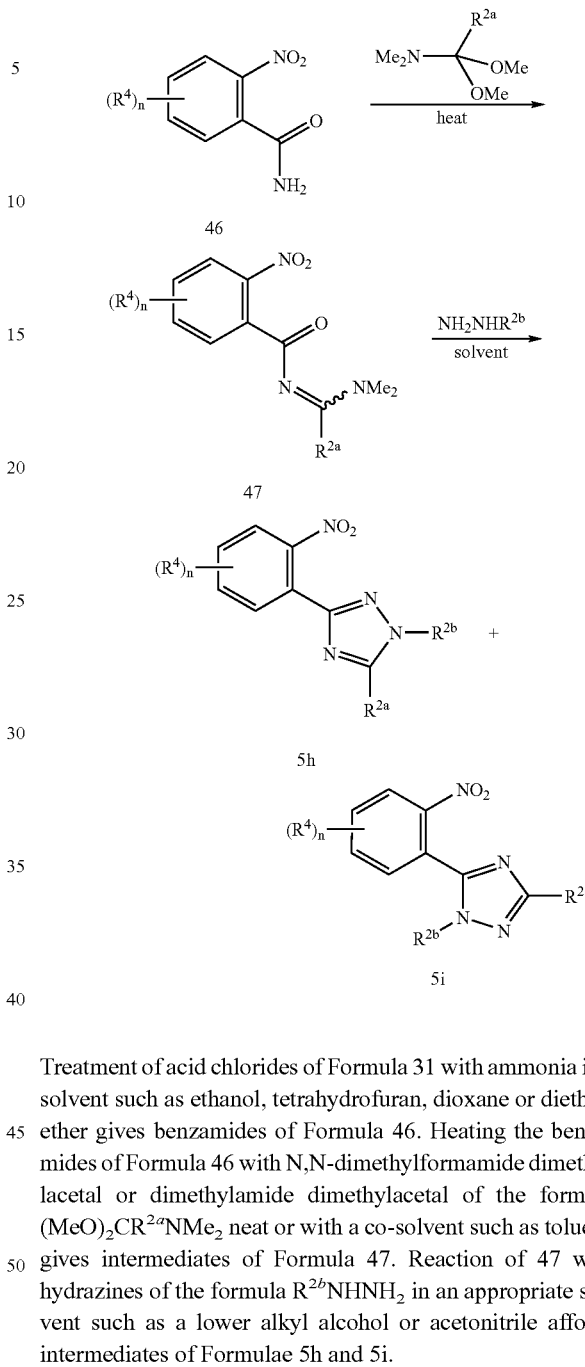

Treatment of acid chlorides of Formula 31 with ammonia in a solvent such as ethanol, tetrahydrofuran, dioxane or diethylether gives benzamides of Formula 46. Heating the benzamides of Formula 46 with N,N-dimethylformamide dimethylacetal or dimethylamide dimethylacetal of the formula $(MeO)_2CR^{2a}NMe_2$ neat or with a co-solvent such as toluene gives intermediates of Formula 47. Reaction of 47 with hydrazines of the formula $R^{2b}NHNH_2$ in an appropriate solvent such as a lower alkyl alcohol or acetonitrile affords intermediates of Formulae 5h and 5i.

Scheme 20 shows the preparation of substituted 2-nitrophenyltetrazoles of Formula 5j, 5k and 5l from 2-nitrobenzonitriles of Formula 40. Treatment of benzonitriles of Formula 40 with sodium azide in N,N-dimethylformamide or acetonitrile gives tetrazoles of Formula 5j. Alkylation of Formula 5j with an alkylating agent of the formula $R^2Lg$ (where $R^2$ is unsubstituted or substituted alkyl or haloalkyl and Lg is a leaving group such as halogen or tosylate) in the presence of a suitable base such as potassium carbonate in a solvent such as N,N-dimethylformamide provides intermediates of Formulae 5k and 5l.

Scheme 20

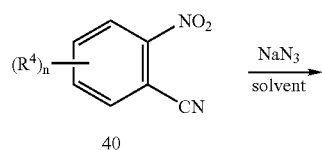

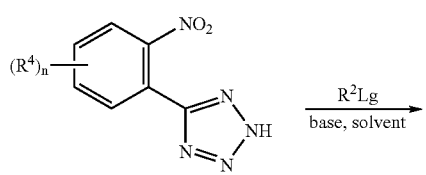

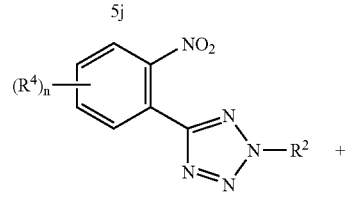

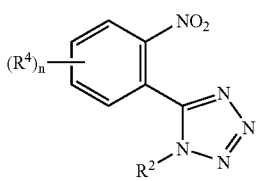

Lg is a leaving group

Scheme 21 illustrates the method for preparing 2-nitrophenylimidazolines of Formulae 5m, 5n and 5o. Heating methyl 2-nitrobenzoates of Formula 49 with a substituted 1,2-diaminoethane of Formula 50 neat or in a suitable solvent such as toluene, xylene or dichlorobenzene at temperatures between 100 and 250° C. gives 2-nitrophenylimidazolines of Formula 5m. Alkylation of 5m with an alkylating agent of formula $R^{2e}$Lg (where Lg is a leaving group such as halogen or tosylate) in the presence of a suitable base such as potassium carbonate or sodium hydride in a solvent such as tetrahydrofuran, dioxane or N,N-dimethylformamide provides intermediates of Formulae 5n and 5o.

Scheme 21

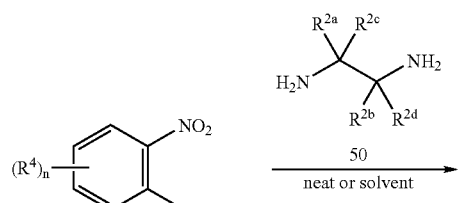

-continued

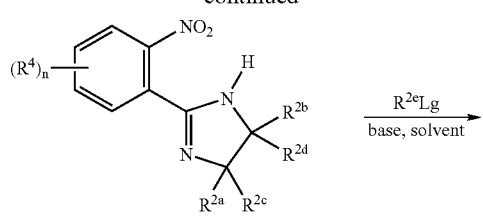

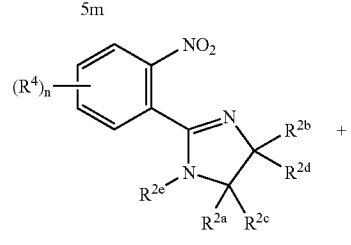

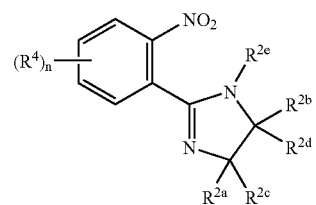

Lg is a leaving group

Scheme 22 outlines a method for preparing 2-nitrophenylimidazoles of Formulae 5p, 5q and 5r.

Scheme 22

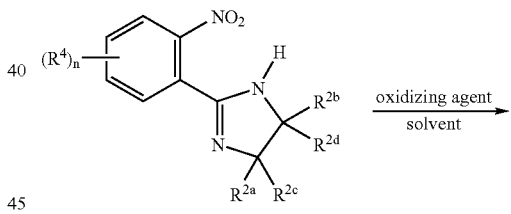

$R^{2c}$ and $R^{2d}$ are both H

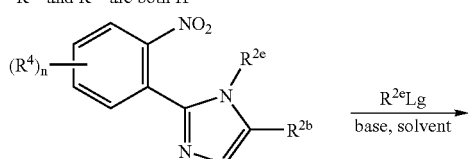

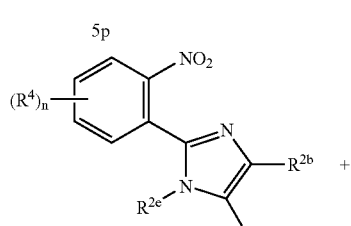

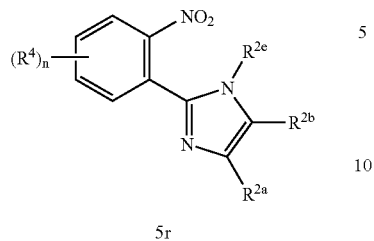

5r

Oxidation of nitrophenylimidazolines of Formula 5m (where $R^{2c}$ and $R^{2d}$ are both hydrogen) with a suitable oxidizing agent such as manganese dioxide or pyridinium dichromate in a solvent such as dichloromethane or N,N-dimethylformamide gives nitrophenylimidazoles of Formula 5p. Alkylation of 5p with an alkylating agent of the formula $R^{2e}$Lg (where Lg is a leaving group such as halogen or tosylate) in the presence of a suitable base such as potassium carbonate or sodium hydride in a solvent such as tetrahydrofuran, dioxane or N,N-dimethylformamide provides intermediates of Formulae 5q and 5r.

Scheme 23 illustrates a method for preparing 2-nitrophenyl tetrahydropyrimidines of Formulae 5s, 5t and 5u. Heating methyl 2-nitrobenzoates of Formula 49 with a substituted 1,3-diaminopropane of Formula 51 neat or in a suitable solvent such as toluene, xylene or dichlorobenzene at temperatures between 100 and 250° C. gives nitrophenyl tetrahydropyrimidines of Formula 5s. Alkylation of 5s with an alkylating agent of the formula $R^{2g}$Lg (where Lg is a leaving group such as halogen or tosylate) in the presence of a suitable base such as potassium carbonate or sodium hydride in a solvent such as tetrahydrofuran, dioxane or N,N-dimethylformamide provides intermediates of Formulae 5t and 5u.

Scheme 23

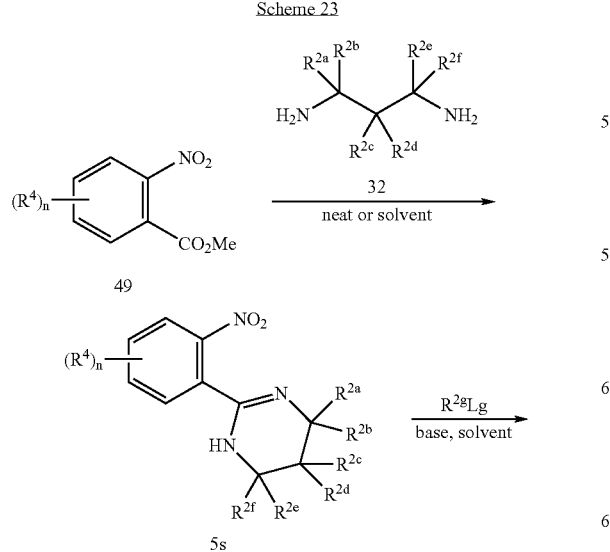

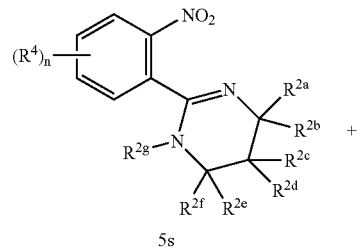

5s

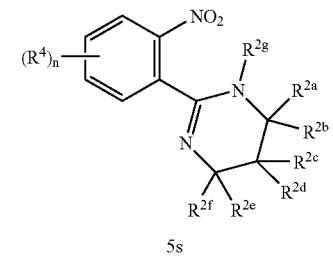

5s

The synthesis of 2-nitrophenylpyrimidines of Formula 5v is illustrated in Scheme 24. Reaction of nitrobenzonitriles of Formula 40 with gaseous HCl in methanol, with or without a cosolvent such as diethyl ether or tetrahydrofuran, affords imidate hydrochloride salts of Formula 52. Treatment of imidates of Formula 52 with ammonium chloride in methanol gives nitrobenzamidine hydrochloride salts of Formula 53. Compounds of Formula 53 afford intermediates of Formula 5v on condensation with aldoketones or diketones of Formula 54 in a suitable solvent, preferably a lower alkyl alcohol, in the presence of a base such as sodium methylate or potassium carbonate.

Scheme 24

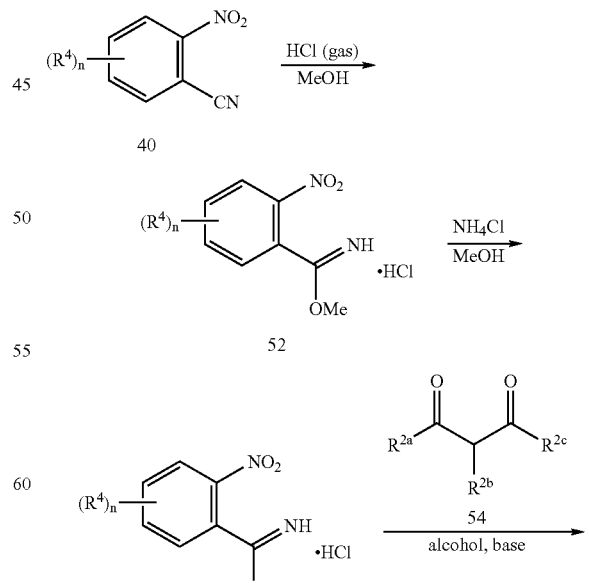

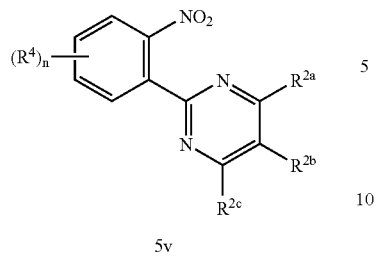

5v

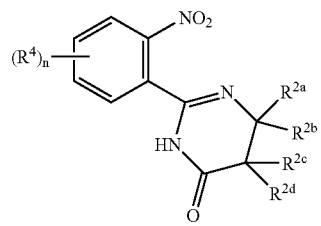

5x

The synthesis of 2-nitrophenyltriazines of Formula 5w is shown in Scheme 25. Condensation of nitrobenzamidine hydrochloride salts of Formula 53 with acylimidates of Formula 55 in a suitable solvent, preferably a lower alkyl alcohol, in the presence of base, e.g. sodium methylate or potassium carbonate, affords intermediates of Formula 5w.

The preparation of nitrophenyl-substituted azoles of Formula 5y is shown in Scheme 27. Reaction of substituted 2-halo nitrobenzenes of Formula 57 (where Hal is halogen, preferably fluorine) with azoles of Formula 58 in the presence of a suitable base such as potassium carbonate or sodium hydride in a solvent such as N,N-dimethylformamide, acetonitrile or dioxane provides intermediates of Formula 5y.

Scheme 25

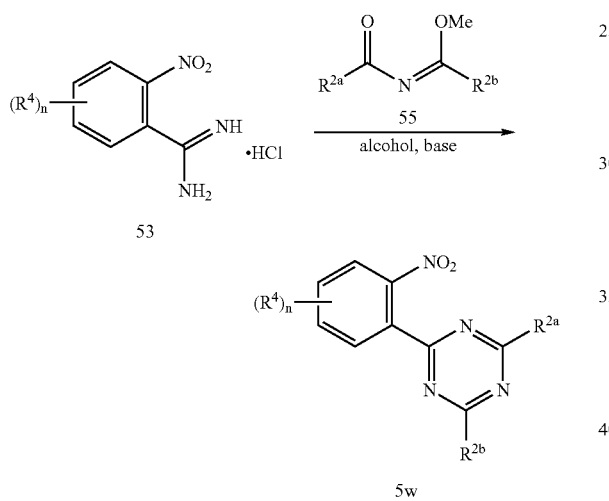

Scheme 27

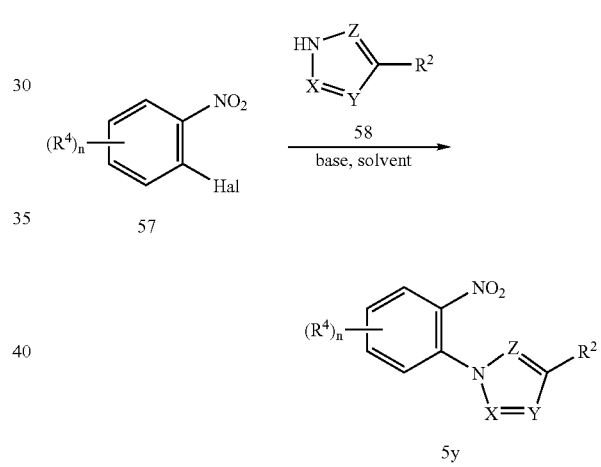

The preparation of 2-nitrophenyltetrahydropyrimidinones of Formula 5x is outlined in Scheme 26. Condensation of a nitrophenyl imidate salt of Formula 52 with substituted β-alanine esters of Formula 56 in a suitable solvent, preferably a lower-alkyl alcohol in the presence of base, e.g. sodium methylate or potassium carbonate, affords intermediates of Formula 5x.

Scheme 26

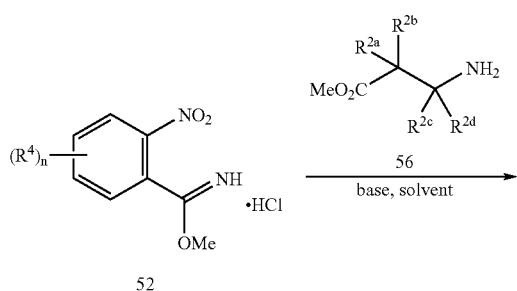

Pyrazoles of Formula 17 wherein $R^3(d)$ is $CF_3$, Cl or Br are known compounds. The pyrazole 17 wherein $R^3(d)$ is $CF_3$ can be prepared by literature procedures (*J. Fluorine Chem.* 1991, 53(1), 61-70). Pyrazoles of Formula 17 wherein $R^3(d)$ is Cl or Br can also be prepared by literature procedures (H. Reimlinger and A. Van Overstraeten, *Chem. Ber.* 1966, 99(10), 3350-7). A useful alternative method for the preparation of pyrazoles of Formula 17 wherein $R^3(d)$ is Cl or Br is depicted in Scheme 28. Metallation of the sulfamoyl pyrazole of Formula 58 with n-butyllithium followed by direct halogenation of the anion with either hexachloroethane (for $R^3(d)$ being Cl) or 1,2-dibromotetrachloroethane (for $R^3(d)$ being Br) affords the halogenated derivatives 59. Removal of the sulfamoyl group with trifluoroacetic acid (TFA) at room temperature proceeds cleanly and in good yield to afford the pyrazoles of Formula 17b wherein $R^3(d)$ is Cl or Br respectively. One skilled in the art will recognize that Formula 17c is a tautomer of Formula 17b.

Scheme 28

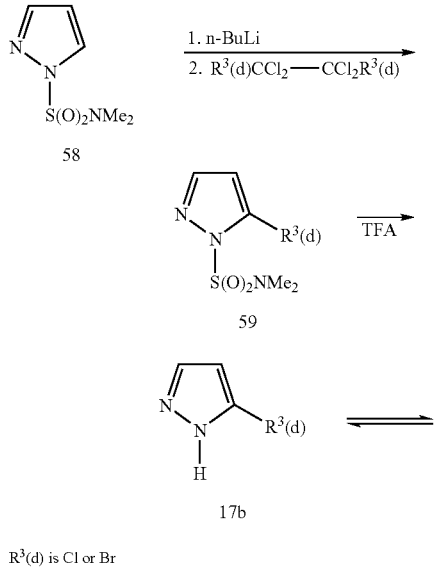

R³(d) is Cl or Br

The synthesis of representative pyrazole acids of Formula 41 is depicted in Scheme 29. Reaction of a dimethylaminoylidene ketoester of Formula 61 with a substituted hydrazine (62) affords the pyrazole of Formula 63. Preferred R³(d) substituents include alkyl and haloalkyl, with 2,2,2-trifluoroethyl especially preferred. The esters of Formula 63 are converted to the acids of Formula 4i by standard hydrolysis.

Scheme 29

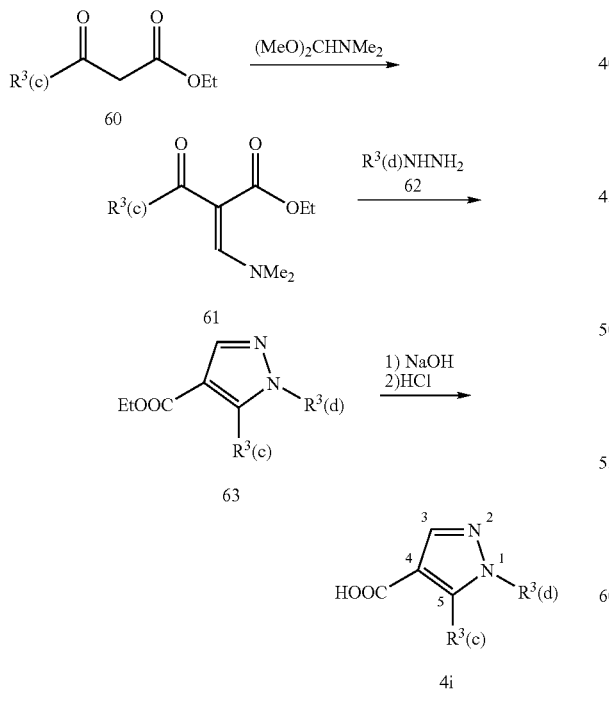

The synthesis of pyrazole acids of Formula 4j, which are related to the preferred moiety J-6 wherein R³ is a substituted 2-pyridyl moiety attached to the 5-position of the pyrazole ring, is depicted in Scheme 30. This synthesis is conducted according to the general synthesis described for Scheme 29.

Scheme 30

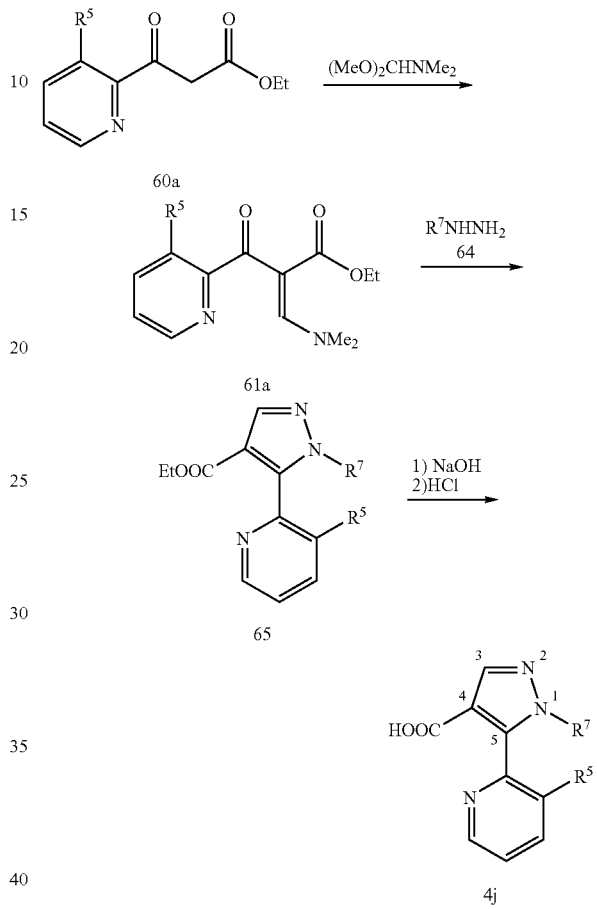

The synthesis of representative pyrazole acids of Formula 4k, as well as an alternative synthesis of Formula 4i, is depicted in Scheme 31.

Scheme 31

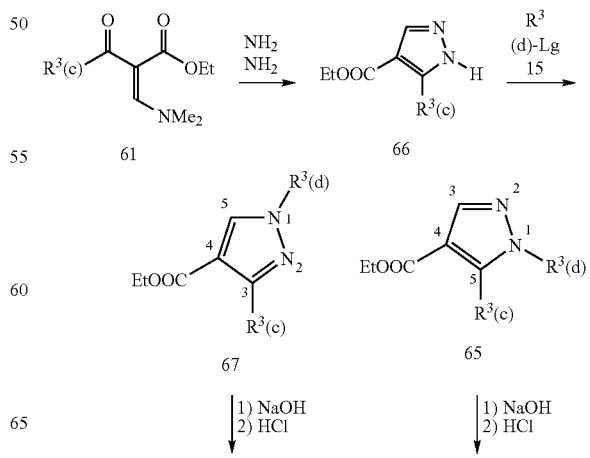

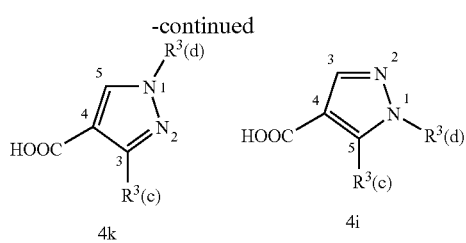

4k  4i

Reaction of the dimethylaminoylidene ketoester of Formula 61 with hydrazine affords the pyrazole of Formula 66. Reaction of the pyrazole 66 with an alkylating agent of Formula 15 (see Scheme 8) affords a mixture of pyrazoles of Formulae 67 and 65. This mixture of pyrazole isomers is readily separated by chromatographic methods and converted to the corresponding acids 4k and 4i, respectively. Preferred $R^3$(d) substituents include alkyl and haloalkyl groups.

The synthesis of pyridinylpyrazole acids of Formula 4m, which are related to the preferred moiety J-7 wherein $R^3$ is a substituted 2-pyridinyl and attached to the 3-position of the pyrazole ring, as well as an alternative synthesis of Formula 4j, is depicted in Scheme 32. This synthesis is conducted according to the general synthesis described for Scheme 31.

Scheme 32

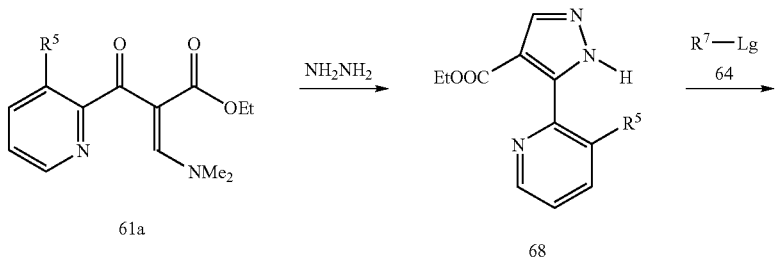

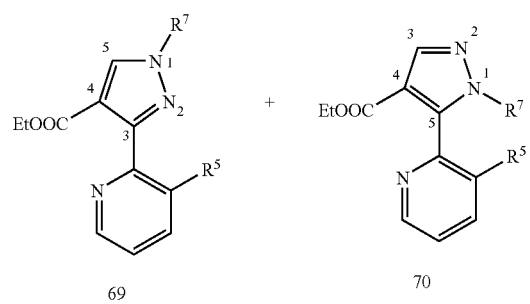

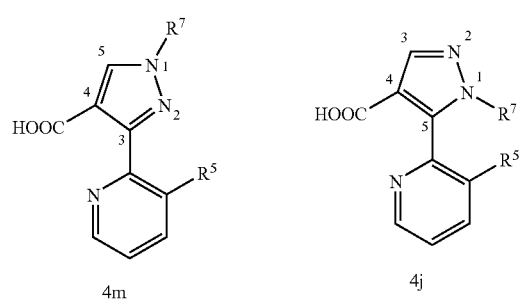

A general synthesis of pyrrole acids of Formula 22 is depicted in Scheme 33. Treatment of a compound of Formula 71 with 2,5-dimethoxytetrahydrofuran (72) affords a pyrrole of Formula 73. Formylation of the pyrrole 73 to provide the aldehyde of Formula 74 can be accomplished by using standard Vilsmeier-Haack formylation conditions, such as treatment with N,N-dimethylformamide (DMF) and phosphorus oxychloride. Halogenation of the compound of Formula 74 with N-halosuccinimides (NXS) such as N-chlorosuccinimide or N-bromosuccinimide occurs preferentially at the 4-position of the pyrrole ring. Oxidation of the halogenated aldehyde affords the pyrrole acid of Formula 4n. The oxidation can be accomplished by using a variety of standard oxidation conditions.

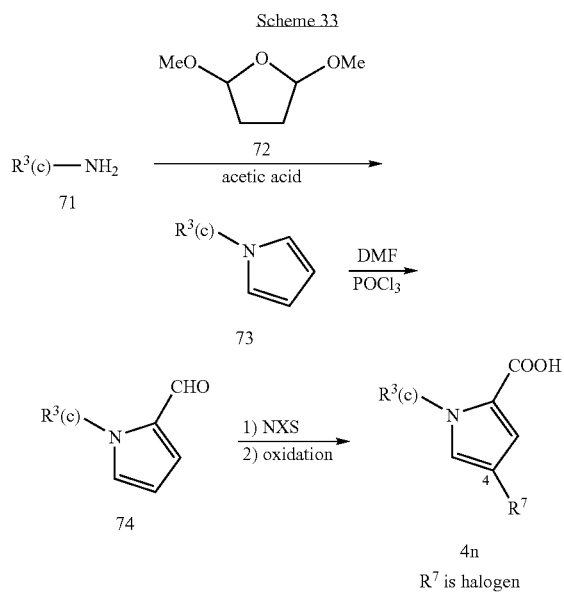

The synthesis of certain pyridinylpyrrole acids of Formula 4o, which are related to the preferred moiety J-4 wherein $R^5$ is a substituted 2-pyridinyl and attached to the nitrogen of the pyrrole ring, is depicted in Scheme 34. This synthesis is conducted according to the general synthesis described for Scheme 33. The compound of Formula 71a, 3-Chloro-2-aminopyridine, is a known compound (see *J. Heterocycl. Chem.* 1987, 24(5), 1313-16).

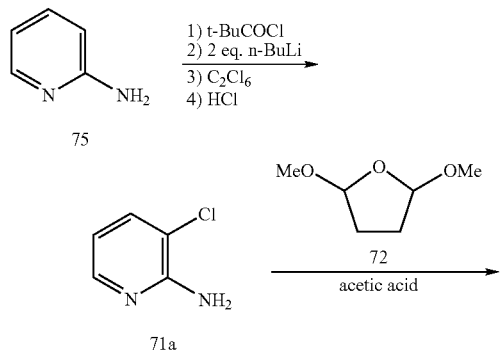

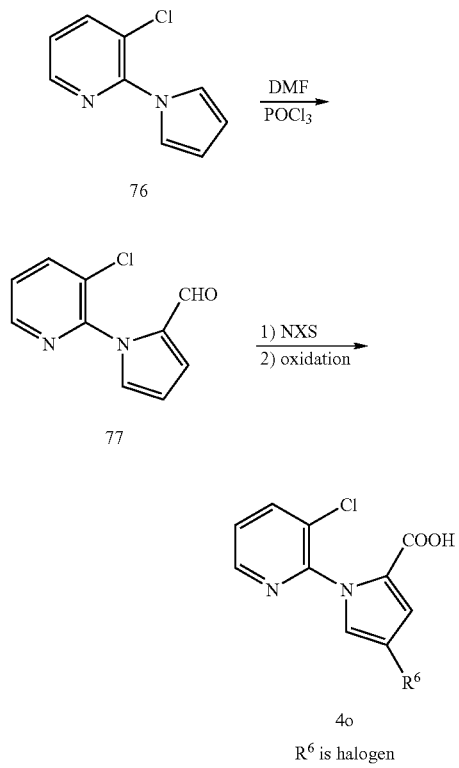

The synthesis of pyrrole acids of Formula 4p is depicted in Scheme 35. Cycloaddition of an allene of Formula 80 with a phenylsulfonyl hydrazide of Formula 79 (see Pavri, N. P.; Trudell, M. L. *J. Org. Chem.* 1997, 62, 2649-2651) affords a pyrroline of Formula 81. Treatment of the pyrroline of Formula 81 with tetrabutylammonium fluoride (TBAF) gives a pyrrole of Formula 82. Reaction of the pyrrole 82 with an alkylating agent $R^3(d)$-Lg (wherein Lg is a leaving group as defined above) followed by hydrolysis affords a pyrrole acid of Formula 4p.

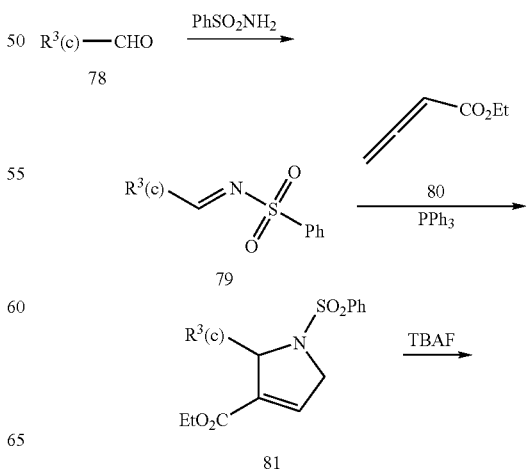

The synthesis of pyrrole acids of Formula 4q, which are related to the preferred moiety J-5 wherein $R^5$ is phenyl or 2-pyridyl and attached to the 2 position of the pyrrole ring, is depicted in Scheme 36. The synthesis is conducted according to the general method described for Scheme 35.

The synthesis of pyrrole acids of Formula 4s, which are related to the preferred moiety J-10, wherein $R^5$ is a substituted phenyl or a substituted 2-pyridinyl ring is depicted in Scheme 38. The synthesis is conducted according to the general method described for Scheme 37.

The synthesis of pyrrole acids of Formula 4r is depicted in Scheme 37. Reaction of an α,β-unsaturated ester of Formula 88 with p-tolylsulfonylmethyl isocyanide (TosMIC) provides a pyrrole of Formula 90. For a leading reference, see Xu, Z. et al, *J. Org. Chem.*, 1988, 63, 5031-5041. Reaction of the pyrrole of Formula 90 with an alkylating agent $R^3(d)$-Lg (wherein Lg is a leaving group as defined above) followed by hydrolysis affords a pyrrole acid of Formula 4r.

Synthesis of certain pyrazole amide analogs of Formula Ie is depicted in Scheme 39.

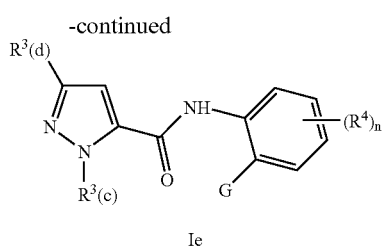

Ie

This procedure takes advantage of the lithiated derivative of Formula 93. Treatment of a compound of Formula 93 with lithium diisopropylamide (LDA) followed by quenching of the lithium salt with an aryl isocyanate of Formula 94 affords compounds of Formula Ic, a subset of the compounds of Formula I. The aryl isocyanates can be prepared from compounds of Formula 2a (see Scheme 3) by, for example, treatment with phosgene or phosgene equivalents such as diphosgene or triphosgene. For leading references for preparing isocyanates, see March, *Advanced Organic Chemistry: Reactions, Mechanisms and Structure, Third Edition*, John Wiley & Sons, New York, 1985; p. 370.

Pyrazolecarboxylic acids of Formula 4t wherein $R^3$ is $CF_3$ can be prepared by the method outlined in Scheme 8.

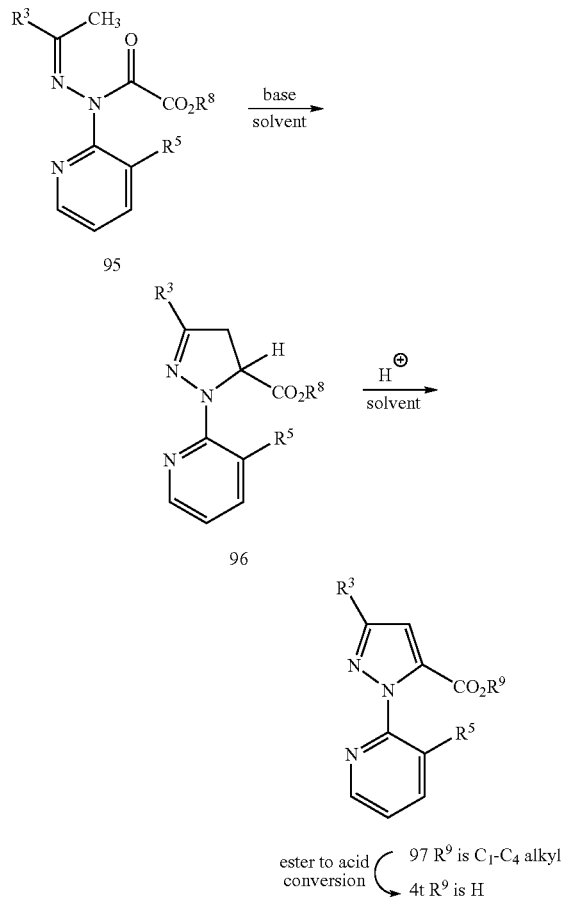

Reaction of a compound of Formula 95 wherein $R^8$ is $C_1$-$C_4$ alkyl with a suitable base in a suitable organic solvent affords the cyclized product of Formula 96 after neutralization with an acid such as acetic acid. The suitable base can be, for example but not limitation, sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 96 to give the compound of Formula 97, followed by converting the carboxylic ester function to carboxylic acid, affords the compound of Formula 4t. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 40, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 40, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4t. The carboxylic acid can be isolated by methods known to those skilled in the art, including crystallization, extraction and distillation.

Compounds of Formula 95 can be prepared by the method outlined in Scheme 41.

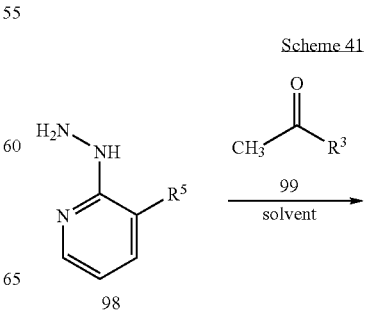

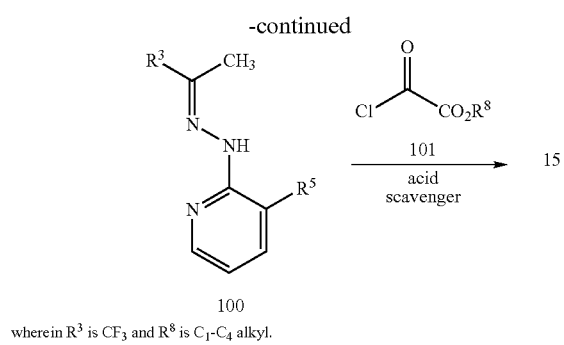

100 wherein $R^3$ is $CF_3$ and $R^8$ is $C_1$-$C_4$ alkyl.

Treatment of a hydrazine compound of Formula 98 with a ketone of Formula 99 in a solvent such as water, methanol or acetic acid gives the hydrazone of Formula 100. One skilled in the art will recognize that this reaction may require catalysis by an optional acid and may also require elevated temperatures depending on the molecular substitution pattern of the hydrazone of Formula 100. Reaction of the hydrazone of Formula 100 with the compound of Formula 101 in a suitable organic solvent such as, for example but not limitation, dichloromethane or tetrahydrofuran in the presence of an acid scavenger such as triethylamine provides the compound of Formula 95. The reaction is usually conducted at a temperature between about 0 and 100° C. Hydrazine compounds of Formula 98 can be prepared by standard methods, such as by contacting the corresponding halo compound of Formula 15a (Scheme 9a) with hydrazine.

Pyrazolecarboxylic acids of Formula 4u wherein $R^3$ is Cl or Br can be prepared by the method outlined in Scheme 42.

Scheme 42

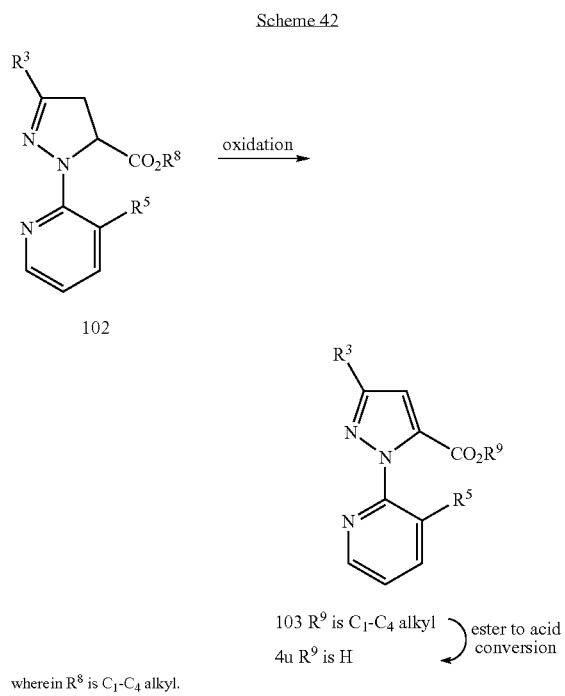

wherein $R^8$ is $C_1$-$C_4$ alkyl.

Oxidization of the compound of Formula 102 optionally in the presence of acid to give the compound of Formula 103 followed by conversion of the carboxylic ester function to the carboxylic acid provides the compound of Formula 4u. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 102 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 102. To obtain complete conversion, one to five equivalents of acid can be used. The preferred oxidant is potassium persulfate and the oxidation is preferably carried out in the presence of sulfuric acid. The reaction can be carried out by mixing the compound of Formula 102 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 103 can be isolated by methods known to those skilled in the art, including crystallization, extraction and distillation. Methods suitable for converting the ester of Formula 103 to the carboxylic acid of Formula 4u are already described for Scheme 40.

Compounds of Formula 102 can be prepared from corresponding compounds of Formula 104 as shown in Scheme 43.

Scheme 43

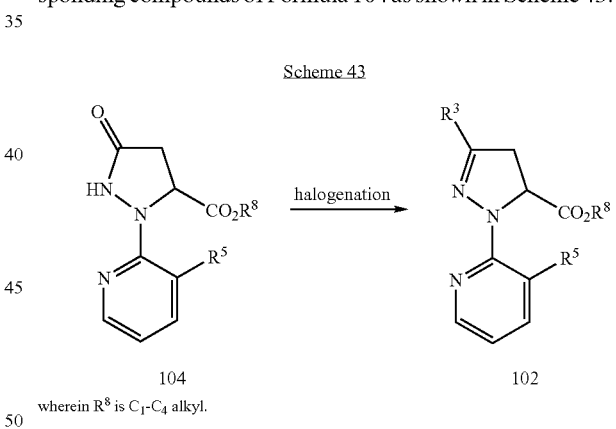

wherein $R^8$ is $C_1$-$C_4$ alkyl.

Treatment of a compound of Formula 104 with a halogenating reagent, usually in the presence of a solvent, affords the corresponding halo compound of Formula 102. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 104 should be used, preferably between about 0.33 and 1.2 equivalents. To obtain complete conversion, at least 0.20 equivalents of phosphorus pentahalide versus the compound of Formula 104 should be used, preferably between about 0.20 and 1.0 equivalents. Compounds of Formula 104 wherein $R^6$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 104 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 102, can be isolated by methods known to those skilled in the art, including crystallization, extraction and distillation.

Alternatively, compounds of Formula 102 wherein $R^3$ is Br or Cl can be prepared by treating the corresponding compounds of Formula 102 wherein $R^3$ is a different halogen (e.g., Cl for making Formula 102 wherein $R^3$ is Br) or a sulfonate group such as p-toluenesulfonate with hydrogen bromide or hydrogen chloride, respectively. By this method the $R^3$ halogen or sulfonate substituent on the Formula 102 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^3$ in the starting compound of Formula 102 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 102 wherein $R^3$ is Br) can facilitate the reaction. The product of Formula 102 is isolated by the usual methods known to those skilled in the art, including extraction, distillation and crystallization.

Starting compounds of Formula 102 wherein $R^3$ is Cl or Br can be prepared from corresponding compounds of Formula 104 as already described. Starting compounds of Formula 102 wherein $R^3$ is a sulfonate group can likewise be prepared from corresponding compounds of Formula 104 by standard methods such as treatment with a sulfonyl chloride (e.g., p-toluenesulfonyl chloride) and base such as a tertiary amine (e.g., triethylamine) in a suitable solvent such as dichloromethane.

Pyrazolecarboxylic acids of Formula 4v wherein $R^3$ is $OCH_2CF_3$ can be prepared by the method outlined in Scheme 44.

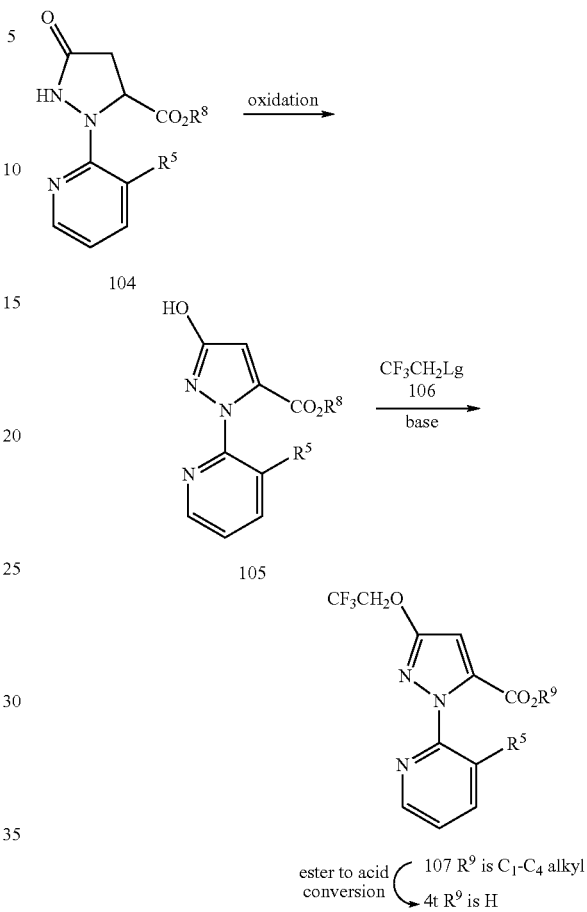

wherein $R^8$ is $C_1$-$C_4$ alkyl, and Lg is a leaving group.

In this method, instead of being halogenated as shown in Scheme 43, the compound of Formula 104 is oxidized to the compound of Formula 105. The reaction conditions for this oxidation are as already described for the conversion of the compound of Formula 102 to the compound of Formula 103 in Scheme 42.

The compound of Formula 105 is then alkylated to form the compound of Formula 107 by contact with an alkylating agent $CF_3CH_2Lg$ (106) in the presence of a base. In the alkylating agent 106, Lg is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C. The product of Formula 107 can be isolated by conventional techniques such as extraction. The ester of Formula 107 can then be converted to the carboxylic acid of Formula 4v by the methods already described for the conversion of Formula 97 to Formula 4t in Scheme 40.

Compounds of Formula 104 can be prepared from compounds of Formula 98 as outlined in Scheme 45.

Scheme 45

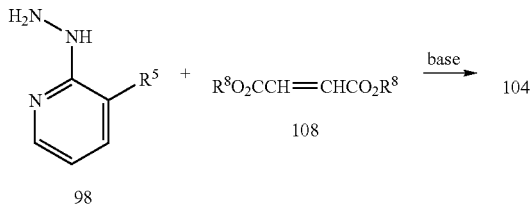

98
wherein $R^8$ is $C_1$-$C_4$ alkyl.

In this method, a hydrazine compound of Formula 98 is contacted with a compound of Formula 108 (a fumarate ester or maleate ester or admixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 108 should be used, preferably between 0.9 and 1.3 equivalents. Greater than 1.0 equivalents of the compound of Formula 108 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 108 and the base in the solvent. The mixture can be heated or cooled to a desired temperature and the compound of Formula 108 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 98 and Formula 108. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^8$ function on the compound of Formula 104 may be hydrolyzed to —$CO_2H$; for example, the presence of water in the reaction mixture can promote such hydrolysis. If the carboxylic acid (—$CO_2H$) is formed, it can be converted back to —$CO_2R^8$ wherein $R^8$ is $C_1$-$C_4$ alkyl using esterification methods well-known in the art. The desired product, a compound of Formula 104, can be isolated by methods known to those skilled in the art, such as crystallization, extraction or distillation.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

Preparation of N-[4-Bromo-2-(4,5-dihydro-1H-imidazol-2-yl)-6-methylphenyl]-1-(3-chloro-2-pyridinyl)-3-(trifluoromethyl)-1H-pyrazole-5-carboxamide Step A. Preparation of 4,5-Dihydro-2-(3-methyl-2-nitrophenyl)-1H-imidazole A solution of methyl 3-methyl-2-nitrobenzoate 3.13 g (16.1 mmol) in ethylenediamine (15 mL) was heated at reflux for 1.5 hours, at which point the solvent was removed at 130° C. under reduced pressure. The residue was then heated at 190° C. for 1.25 hours before being cooled on ice and purified by flash column chromatography (silica gel, 1% to 10% methanol in dichloromethane) to give the title compound of Step A (0.35 g) as a brown oil.

$^1$H NMR (CDCl$_3$) δ 7.52 (m, 1H), 7.39 (t, 1H), 7.35 (m, 1H), 3.74 (s, 4H), 2.33 (s, 3H).

Step B: Preparation of 2-(4,5-Dihydro-1H-imidazol-2-yl)-6-methylbenzenamine

To a solution of the title compound of Step A (0.5 g, 2.44 mmol) in ethanol (50 mL) was added palladium hydroxide (50 mg, 20 wt % on carbon). The flask was twice evacuated and flushed with nitrogen and then twice evacuated and flushed with hydrogen. The mixture was vigorously stirred under a balloon of hydrogen for 3 hours before being evacuated, exposed to air and filtered through a pad of Celite®. The solution was concentrated and filtered through a pad of silica gel, eluting with 5% then 10% methanol in dichloromethane, then 5% triethylamine, 10% methanol, 85% dichloromethane. The material eluting in triethylamine/methanol/dichloromethane was concentrated to give the title compound of Step B (0.38 g) as a light brown oil.

$^1$H NMR (CDCl$_3$) δ 7.3-7.2 (d, 1H), 7.1 (d, 1H), 6.57 (t, 1H), 3.76 (s, 4H), 2.18 (s, 3H).

Step C: Preparation of 4-Bromo-2-(4,5-dihydro-1H-imidazol-2-yl)-6-methylbenzenamine To a solution of the title compound of Step B (0.38 g, 2.17 mmol) in N,N-dimethylformamide (10 mL) was added N-bromosuccinimide (0.38 g, 2.13 mmol) and the mixture was stirred at ambient temperature for 1 hour. Additional N-bromosuccinimide (0.06 g, 0.34 mmol) was added and the mixture stirred for an additional 0.5 hour before being diluted with ethyl acetate and washed three times with water. The combined aqueous fractions were extracted with ethyl acetate and the organic layer was washed with water. The combined organic fractions were dried (magnesium sulfate), concentrated and purified by flash column chromatography (silica gel, 2% then 5% methanol in dichloromethane) to give the title compound of Step C (94 mg) as a light brown oil.

$^1$H NMR (CDCl$_3$) δ 7.33 (d, 1H), 7.18 (d, 1H), 3.76 (s, 4H), 2.15 (s, 3H).

Step D: Preparation of N-[4-Bromo-2-(4,5-dihydro-1H-imidazol-2-yl)-6-methylphenyl]-1-(3-chloro-2-pyridinyl)-3-(trifluoromethyl)-1H-pyrazole-5-carboxamide To a solution of 1-(3-chloro-2-pyridinyl)-3-(trifluoromethyl)-1H-pyrazole-5-carboxylic acid (119 mg, 0.41 mol) in dichloromethane (10 mL)-containing dimethylformamide (1 drop) was added oxalyl chloride (390 μL, 0.48 mmol). The mixture was stirred at ambient temperature for 2 hours before being concentrated under reduced pressure. The mixture was redissolved in dichloromethane (5 mL) and added to a solution of the title compound of Step C (94 mg, 0.37 mmol), dimethylaminopyridine (measured as the amount covering the tip of a small laboratory spatula) and triethylamine (77 μL, 0.56 mmol) in dichloromethane (5 mL). The mixture was stirred overnight at ambient temperature before the addition of a saturated solution of sodium bicarbonate. The mixture was filtered through a column of Celite® filter aid, concentrated and purified by flash column chromatography (silica gel, 5% then 20% acetone in chloroform then 1% then 2% then 5% methanol in dichloromethane) to give the title compound of Example 1, a compound of the invention, as a white solid (22 mg).

$^1$H NMR (CDCl$_3$) δ 8.5 (dd, 1H), 7.9 (dd, 1H), 7.5 (dd, 1H), 7.4 (m, 2H), 7.30 (s, 1H), 3.79 (s, 4H), 2.20 (s, 3H).

EXAMPLE 2

Preparation of 1-(3-Chloro-2-pyridinyl)-N-[2-1H-imidazol-2-yl)-6-methylphenyl]-3-(trifluoromethyl)-1H-pyrazole-5-carboxamide

Step A: Preparation of 2-(3-Methyl-2-nitrophenyl)-1H-imidazole

To a solution of the title compound of Example 1, Step A (0.35 g, 1.71 mmol) in dimethylformamide (20 mL) was added activated manganese dioxide (4.46 g, 51.3 mmol) and the mixture was heated at 120° C. for 2 hours. After cooling, the mixture was diluted with ethyl acetate, filtered through a pad of Celite® and washed three times with water and once with a saturated solution of sodium chloride. The organic phase was dried (magnesium sulfate), concentrated and purified by flash column chromatography (silica gel, 60% then 80% ethyl ether in hexanes then ethyl ether) to give the title compound of Step A (0.1 g) as a white solid.

$^1$H NMR (CDCl$_3$) δ 7.76 (d, 1H), 7.46 (t, 1H), 7.33 (d, 1H), 7.3-7.1 (2×bs, 2H), 2.37 (s, 3H).

Step B: Preparation of 2-(1H-Imidazol-2-yl)-6-methylbenzenamine

To a solution of the title compound of Step A (0.1 g, 0.49 mmol) in ethanol (20 mL) was added palladium hydroxide (20 wt % on carbon) (measured as the amount covering the tip of a small laboratory spatula). The flask was twice evacuated and flushed with nitrogen and then twice evacuated and flushed with hydrogen. The mixture was vigorously stirred under a balloon of hydrogen for 0.45 hour before being evacuated, exposed to air and filtered through a pad of Celite®. Concentration gave the title compound of Step B as an off white solid (82 mg).

$^1$H NMR (CDCl$_3$) δ 7.3-7.2 (m, 2H), 7.1 (m, 2H), 6.67 (t, 1H), 6.0 (bs), 2.23 (s, 3H).

Step C: Preparation of 1-(3-Chloro-2-pyridinyl)-N-[2-1H-imidazol-2-yl)-6-methylphenyl]-3-(trifluoromethyl)-1H-pyrazole-5-carboxamide To a solution of 1-(3-chloro-2-pyridinyl)-3-(trifluoromethyl)-1H-pyrazole-5-carboxylic acid (165 mg, 0.57 mmol) in dichloromethane (5 mL) containing dimethylformamide (1 drop) was added oxalyl chloride (54 μL, 0.61 mmol). The mixture was stirred at ambient temperature for 2 hours before being concentrated under reduced pressure and redissolved in dichloromethane (5 mL). Diisopropylethylamine (127 μL, 0.71 mmol) was added followed by the title compound of Step B (82 mg, 0.47 mmol) and the mixture was stirred at ambient temperature for 4 hours. Dimethylaminopyridine (measured as the amount covering the tip of a small laboratory spatula) was then added and the mixture was stirred at ambient temperature overnight. A saturated solution of sodium bicarbonate was then added and the mixture was filtered-through a column of Celite®. Concentration and purification by flash column chromatography (silica gel, 60% then 80% ethyl ether in hexanes then ethyl ether) gave the title compound of Example 2, a compound of the invention, as a white solid (0.12 g) mp 224-226° C.

EXAMPLE 3

Step A: Preparation of N-[2-(4-Bromo-1H-imidazol-2-yl)-6-methylphenyl]-1-(3-chloro-2-pyridinyl)-3-(trifluoromethyl)-1H-pyrazole-5-carboxamide To a solution of the title compound of Example 2 (0.04 g, 0.09 mmol) in dichloromethane (3 mL) was added N-bromosuccinimide (16 mg, 0.09 mmol) and the mixture was stirred at ambient temperature for 1 hour. Purification by flash column chromatography (silica gel, 40% then 60% then 80% ethyl ether in hexanes) gave the title compound of Example 3, a compound of the invention, as a white solid (52 mg).

$^1$H NMR (CDCl$_3$) δ 11.2 (s, 1H), 10.9 (bs, 1H), 8.5 (dd, 1H), 8.2 (bs, 1H), 8.0-7.9 (dd, 1H), 7.53 (s, 1H), 7.5 (dd, 1H), 7.01 (bd, 1H), 6.70 (t, 1H), 6.63 (bd, 1H), 2.30 (s, 3H).

EXAMPLE 4

Preparation of 1-(3-Chloro-2-pyridinyl)-N-[2,4-dichloro-6-(4,5-dihydro-1H-imidazol-2-yl)phenyl]-3-(trifluoromethyl)-1H-pyrazole-5-carboxamide Step A: Preparation of 2,4-Dichloro-6-(4,5-dihydro-1H-imidazol-2-yl)benzenamine To a solution of ethylene diamine (1.2 mL, 18 mmol) in ethyl ether (50 mL) at −20° C. was added n-butyl lithium (6.4 mL, 2.5 M in hexanes, 16 mmol). The mixture was stirred at 0° C. for 0.3 hour before the addition of 2,4-dichloro-6-trifluoromethyl aniline (0.92 g, 4.2 mmol). The mixture was stirred at 0° C. for an additional 1.5 hour, at which point water (0.36 mL, 20 mmol) was added and the solvent was removed under reduced pressure. Purification by flash column chromatography (silica gel, 1% to 10% methanol in dichloromethane) to give the title compound of Step A (0.35 g) as a yellow solid.

$^1$H NMR (CDCl$_3$) δ 7.30 (d, 1H), 7.23 (d, 1H), 6.8 (bs, 2H), 4.7-4.6 (bs, 1H), 3.77 (bs, 4H).

Step B: Preparation of 1-(3-Chloro-2-pyridinyl)-N-[2,4-dichloro-6-(4,5-dihydro-1H-imidazol-2-yl)phenyl]-3-(trifluoromethyl)-1H-pyrazole-5-carboxamide To a solution of 1-(3-chloro-2-pyridinyl)-3-(trifluoromethyl)-1H-pyrazole-5-carboxylic acid (0.6 g, 2.02 mol) in dichloromethane (10 mL) containing dimethylformamide (1 drop) was added oxalyl chloride (198 μL, 2.22 mmol). The mixture was stirred at ambient temperature for 2 hours before being concentrated under reduced pressure and redissolved in dichloromethane (5 mL). Seven tenths of this solution was added to a solution of the title compound of Step A (0.3 g, 1.3 mmol), triethylamine (272 mL, 1.95 mmol) and dimethylaminopyridine (16 mg, 0.13 mmol) in dichloromethane (5 mL) and the mixture was stirred at ambient temperature overnight. A saturated solution of sodium bicarbonate was then added and the mixture was filtered through a column of Celite®. Concentration and purification by flash column chromatography (silica gel, 1% then 2% then 5% methanol in dichloromethane then again in 10% then 20% acetone in chloroform then 5% methanol in dichloromethane) gave the title compound of Example 4, a compound of the invention, as a yellow solid (31 mg).

$^1$H NMR (CDCl$_3$) δ 8.5-8.4 (d, 1H), 7.9 (d, 1H), 7.46 (d, 1H), 7.41 (d, 1H), 7.4 (dd, 1H), 7.31 (s, 1H), 3.77 (s, 4H).

EXAMPLE 5

Preparation of 1-(2-Chlorophenyl)-N-[2-(4,5-dihydro-1-methyl-1H-imidazol-2-yl)-6-methylphenyl]-3-(trifluoromethyl)-1H-pyrazole-5-carboxamide Step A: Preparation of 4,5-Dihydro-1-methyl-2-(3-methyl-2-nitrophenyl)-1H-imidazole A solution of methyl 3-methyl-2-nitrobenzoate (3.0 g, 15.4 mmol) in N-methylethylene diamine (5 g, 68 mmol) was heated at reflux for 1.5 hour, at which point the solvent was removed at 130° C. under reduced pressure. The residue was then heated at 190° C. for 1.25 hour before being cooled on ice to give the title compound of Step A (75% pure) as a brown oil.

$^1$H NMR (CDCl$_3$) δ 7.5 (m, 1H), 7.4 (m, 2H), (3.90 (t, 2H), 3.51 (t, 2H), 2.74 (s, 3H), 2.43 (s, 3H).

Step B: Preparation of 2-(4,5-Dihydro-1-methyl-1H-imidazol-2-yl)-6-methylbenzenamine To a solution of the title compound of Step A (3.37 g, 75% pure) in ethanol (15 mL) was added palladium hydroxide (170 mg, 20 wt % on carbon). The flask was twice evacuated and flushed with nitrogen and then twice evacuated and flushed with hydrogen. The mixture was vigorously stirred under a balloon of hydrogen for 3 hours before being evacuated, exposed to air and filtered through a pad of Celite®. The solution was concentrated and filtered through a pad of silica gel, eluting with 1% then 5% then 10% methanol in dichloromethane, then 5% triethylamine, 10% methanol, 85% dichloromethane. The material eluting in triethylamine/methanol/dichloromethane was concentrated to give the title compound of Step B (1.5 g) as an off white solid.

$^1$H NMR (CDCl$_3$) δ 7.3 (d, 1H), 7.1 (d, 1H), 6.9 (bs, 1H), 6.6 (t, 1H), 5.6 (bs, 1H), 3.6-3.5 (m, 2H), 2.9 (t, 2H), 2.47 (s, 3H), 2.16 (s, 3H).

Step C: Preparation of 1-(2-Chlorophenyl)-N-[2-(4,5-dihydro-1-methyl-1H-imidazol-2-yl)-6-methylphenyl]-3-(trifluoromethyl)-1H-pyrazole-5-carboxamide To a solution of 1-(2-chlorophenyl)-3-(trifluoromethyl)-1H-pyrazole-5-carboxylic acid (1.2 g, 4.13 mol) in dichloromethane (10 mL) containing dimethylformamide (1 drop) was added oxalyl chloride (390 μL, 4.47 mmol). The mixture was stirred at ambient temperature for 1 h before being concentrated under reduced pressure. The mixture was redissolved in dichloromethane (5 mL) and added to a solution of the title compound of Step B (0.65 g, 3.44 mmol), dimethylaminopyridine (42 mg, 0.34 mmol) and triethylamine (766 μL, 5.50 mmol) in dichloromethane (10 mL). The mixture was stirred for 3 days at ambient temperature before the addition of a saturated solution of sodium bicarbonate. The mixture was twice extracted with dichloromethane and the combined organic phases were dried (magnesium sulfate), concentrated and purified by flash column chromatography (silica gel, ethyl ether then ethyl acetate then 2% then 5% methanol in dichloromethane). The material eluting in 5% methanol/dichloromethane was concentrated, redissolved in dichloromethane and shaken with 1 g of 1,5,7-triazabicyclo-[4.4.0]-dec-5-ene on polystyrene resin (Fluka catalog number 90603) for 0.5 hour. Filtration and concentration gave the title compound of Example 5, a compound of the invention (0.16 g).

$^1$H NMR (CDCl$_3$) δ 7.6-7.5 (m, 1H, 7.4 (m, 3H), 7.2 (m, 4H), 3.85 (t, 2H), 3.4 (bm, 2H), 2.71 (s, 3H), 2.17 (s, 3H).

EXAMPLE 6

Preparation of 1-(2-Chlorophenyl)-N-[2-methyl-6-(1-methyl-1H-imidazol-2-yl)phenyl]-3-(trifluoromethyl)-1H-pyrazole-5-carboxamide To a solution of the title compound of Example 5 (35 mg, 76 µmol) in toluene (20 mL) was added activated manganese dioxide (132 mg, 1.52 mmol) and the mixture was heated at reflux for 3 days before being filtered through a pad of Celite®. Concentration and purification by flash column chromatography (silica gel, 60% then 80% ethyl ether in hexanes then ethyl ether) gave the title compound of Example 6, a compound of the invention (19 mg).

$^1$H NMR (CDCl$_3$) δ 10.5 (bs, 1H), 7.5 (m, 1H), 7.4 (m, 3H), 7.3-7.2 (m, 4H), 7.13 (d, 1H), 6.95 (d, 1H), 3.65 (s, 3H), 2.26 (s, 3H).

EXAMPLE 7

Preparation of N-[4-Bromo-2-(4,5-dihydro-1-methyl-1H-imidazol-2-yl)-6-methylphenyl]-1-(2-chlorophenyl)-3-(trifluoromethyl)-1H-pyrazole-5-carboxamide To a solution of the title compound of Example 5 (68 mg, 0.15 mmol) in dichloromethane (3 mL) was added N-bromosuccinimide (26 mg, 0.15 mmol). The mixture was stirred at ambient temperature overnight before being purified by flash column chromatography (silica get, 2% then 5% methanol in dichloromethane) to give the title compound of Example 7, a compound of the invention (36 mg).

$^1$H NMR (CDCl$_3$) δ 8.02 (s, 1H), 7.7-7.6 (d, 1H), 7.5-7.4 (m, 4H), 7.3 (d, 1H), 4.0-3.8 (bm, 4H), 2.94 (s, 3H), 2.34 (s, 3H).

EXAMPLE 8

Preparation of 1-(3-Chloro-2-pyridinyl)-N-[2-methyl-6-(1,4,5,6-tetrahydro-4-oxo-2-pyrimidinyl)phenyl]-3-(trifluoromethyl)-1H-pyrazole-5-carboxamide Step A: Preparation of 3-Methyl-2-nitrobenzamide Methyl 3-methyl-2-nitrobenzoate (10.02 g, 51.3 mmol) was added to a 7N solution of ammonia in methanol (50 mL) and the mixture was heated at 100° C. in a Fisher-Porter tube for 3 hours. The solution was then cooled, concentrated and triturated with dichloromethane to give the title compound of Step A as a white solid (1.4 g).

$^1$H NMR (CDCl$_3$) δ 8.2 (bs, 1H), 7.7 (bs, 1H), 7.6 (m, 3H), 2.28 (s, 3H).

Step B: Preparation of Methyl 3-methyl-2-nitrobenzenecarboximidate tetrafloroborate To a solution of the title compound of Step A (1.07 g, 5.9 mmol) in dichloromethane (15 mL) was added trimethyloxonium tetrafluoroborate (1.06 g, 7.1 mmol) and the mixture was stirred overnight at ambient temperature. Concentration gave the title compound of Step B as a white solid (1.7 g).

$^1$H NMR (DMSO-d$_6$) δ 7.8 (m, 3H), 7.1 (t, 1H), 4.00 (s, 3H), 2.41 (s, 3H).

Step C: Preparation of 5,6-Dihydro-2-(3-methyl-2-nitrophenyl)-4(1H)-pyrimidinone To a solution of the title compound of Step B (1.7 g, 5.9 mmol) in methanol (20 mL) was added β-alanine methyl ester hydrochloride (832 mg, 5.9 mmol) followed by sodium methoxide (2.7 mL, 25 wt % in methanol, 11.8 mmol) and the mixture was heated at reflux for 1.5 hour. The mixture was then cooled, stirred overnight at ambient temperature and again heated at reflux for 3 hours. The mixture was then cooled, concentrated and triturated with dichloromethane. The soluble fraction was then purified by flash column chromatography (silica gel, ethyl ether) to give the title compound of Step C as a white solid (0.12 g).

$^1$H NMR (CDCl$_3$) δ 8.4-8.2 (bs, 1H), 7.6-7.4 (m, 3H), 3.80 (t, 2H), 2.53 (t, 2H), 2.40 (s, 3H).

Step D: Preparation of 2-(2-Amino-3-methylphenyl-5,6-dihydro-4(1H)-pyrimidinone

To a solution of the title compound of Step C (0.12 g, 0.52 mmol) in ethanol (10 mL) was added palladium hydroxide (20 wt % on carbon) (measured as the amount covering the tip of a small laboratory spatula). The flask was twice evacuated and flushed with nitrogen and then twice evacuated and flushed with hydrogen. The mixture was vigorously stirred under a balloon of hydrogen for 2 hours before being evacuated, exposed to air and filtered through a pad of Celite®. The solution was concentrated to give the title compound of Step D (0.11 g).

$^1$H NMR (CDCl$_3$) δ 8.0 (bs, 1H), 7.2-7.1 (m, 2H), 6.7-6.6 (t, 1H), 6.2 (bs, 2H), 3.91 (t, 2H), 2.56 (t, 2H), 2.19 (s, 3H).

Step E: Preparation of 1-(3-Chloro-2-pyridinyl)-N-[2-methyl-6-(1,4,5,6-tetrahydro-4-oxo-2-pyrimidinyl)phenyl]-3-(trifluoromethyl)-1H-pyrazole-5-carboxamide To a solution of 1-(2-chlorophenyl)-3-(trifluoromethyl)-1H-pyrazole-5-carboxylic acid (0.6 g, 2.02 mol) in dichloromethane (10 mL) containing dimethylformamide (1 drop) was added oxalyl chloride (198 µL, 2.22 mmol). The mixture was stirred at ambient temperature for 2 hours before being concentrated under reduced pressure and redissolved in dichloromethane (5 mL). Three tenths of this solution was added to a solution of the title compound of Step D (0.11 g, 0.54 mmol), triethylamine (113 mL, 0.81 mmol) and dimethylamino-pyridine (7 mg, 0.05 mmol) in dichloromethane (5 mL) and the mixture was stirred at ambient temperature overnight. A saturated solution of sodium bicarbonate was then added and the mixture was filtered through a column of Celite®. Concentration and purification by flash column chromatography (silica gel, 1% then 5% then 10% then 20% acetone in chloroform) gave the title compound of Example 8, a compound of the invention, as a white solid (64 mg).

$^1$H NMR (CDCl$_3$) δ 11.3 (bs, 1H), 8.5 (dd, 1H), 7.9 (dd, 1H), 7.5-7.4 (m, 1H), 7.4-7.2 (m, 3H), 7.18 (s, 1H), 3.85 (t, 3H), 2.54 (t, 2H), 2.23 (s, 3H).

By the procedures described herein together with methods known in the art, the following compounds of Tables 1 to 37 can be prepared. The following abbreviations are used in the Tables: Me means methyl, Et means ethyl and Ph means phenyl.

TABLE 1

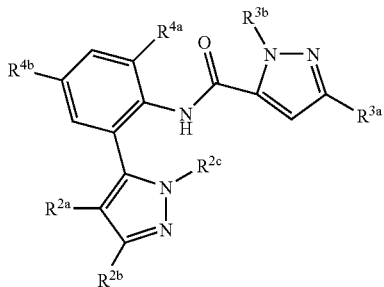

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 3-Cl-2-pyridyl | Me | H |
| H | H | H | CF3 | 3-Cl-2-pyridyl | Me | H |
| H | H | H | CF3 | 2-ClPh | Cl | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |
| Me | H | H | CF3 | 3-Cl-2-pyridyl | Cl | H |
| Me | H | H | CF3 | 3-Cl-2-pyridyl | Me | Br |
| Me | H | H | CF3 | Me | Me | Cl |
| Me | H | H | CF3 | Et | Me | Br |
| Me | H | H | CF3 | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF3 | 2-ClPh | Me | H |
| H | Me | H | CF3 | 2-ClPh | Me | Cl |
| H | Me | H | CF3 | 3-Cl-2-pyridyl | Me | H |
| H | Me | H | CF3 | 3-Cl-2-pyridyl | Me | H |
| H | Me | H | CF3 | 2-ClPh | Cl | H |
| H | Me | H | CF3 | 3-Cl-2-pyridyl | Cl | H |
| H | Me | H | CF3 | 3-Cl-2-pyridyl | Me | Br |
| H | Me | H | CF3 | Me | Me | Cl |
| H | Me | H | CF3 | Et | Me | Br |
| H | Me | H | CF3 | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | CF3 | 2-ClPh | Me | H |
| Me | Me | H | CF3 | 2-ClPh | Me | Cl |
| Me | Me | H | CF3 | 3-Cl-2-pyridyl | Me | H |
| Me | Me | H | CF3 | 3-Cl-2-pyridyl | Me | H |
| Me | Me | H | CF3 | 2-ClPh | Cl | H |
| Me | Me | H | CF3 | 3-Cl-2-pyridyl | Cl | H |
| Me | Me | H | CF3 | 3-Cl-2-pyridyl | Me | Br |
| Me | Me | H | CF3 | Me | Me | Cl |
| Me | Me | H | CF3 | Et | Me | Br |
| Me | Me | H | CF3 | Ph | Me | Cl |
| Me | Me | H | Br | 2-ClPh | Cl | H |

TABLE 1-continued

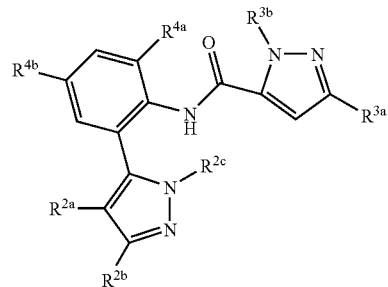

| R2a | R2b | R2c | R3a | R3b | R4a | R4b |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | Me | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 2

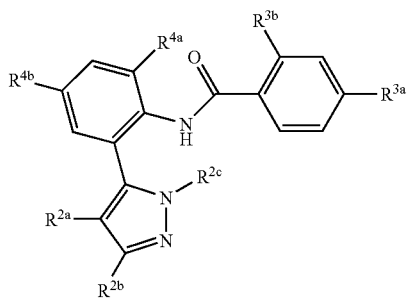

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 2-ClPh | Me | H |
| H | H | H | CF3 | 2-ClPh | Me | H |
| H | H | H | CF3 | 2-ClPh | Cl | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |
| Me | H | H | CF3 | 3-Cl-2-pyridyl | Cl | H |
| Me | H | H | CF3 | 3-Cl-2-pyridyl | Me | Br |

TABLE 2-continued

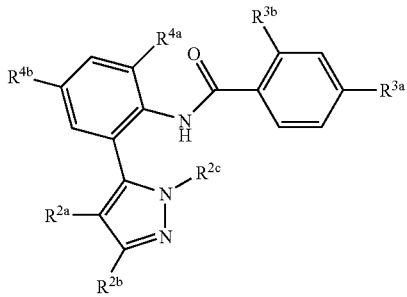

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | H |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF$_3$ | 2-ClPh | Me | H |
| H | H | Me | CF$_3$ | 2-ClPh | Me | Cl |
| H | H | Me | CF$_3$ | 3-Cl-2-pyridyl | Me | H |
| H | H | Me | CF$_3$ | 3-Cl-2-pyridyl | Me | Cl |
| Me | H | Me | CF$_3$ | 3-Cl-2-pyridyl | Me | H |
| Me | H | Me | CF$_3$ | 3-Cl-2-pyridyl | Me | Cl |
| H | Me | Me | CF$_3$ | 3-Cl-2-pyridyl | Me | H |
| H | Me | Me | CF$_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 3

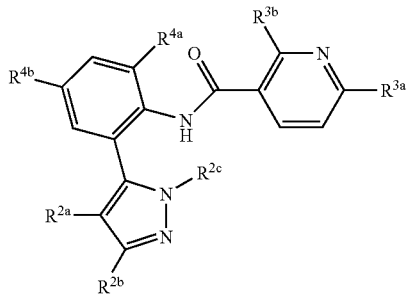

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 2-ClPh | Me | H |
| H | H | H | CF$_3$ | 2-ClPh | Me | H |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 3-Cl-2-pyridyl | Me | H |
| Me | H | H | CF$_3$ | 3-Cl-2-pyridyl | Me | H |
| Me | H | H | CF$_3$ | 2-ClPh | Cl | H |
| Me | H | H | CF$_3$ | 3-Cl-2-pyridyl | Cl | H |
| Me | H | H | CF$_3$ | 3-Cl-2-pyridyl | Me | Br |
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | H |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |

TABLE 3-continued

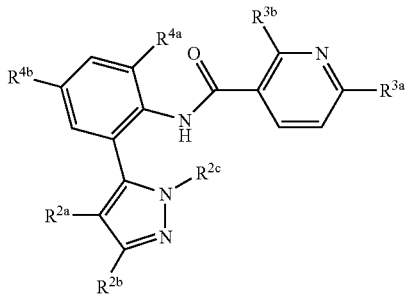

| R²ᵃ | R²ᵇ | R²ᶜ | R³ᵃ | R³ᵇ | R⁴ᵃ | R⁴ᵇ |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF₃ | 2-ClPh | Me | H |
| H | H | Me | CF₃ | 2-ClPh | Me | Cl |
| H | H | Me | CF₃ | 3-Cl-2-pyridyl | Me | H |
| H | H | Me | CF₃ | 3-Cl-2-pyridyl | Me | Cl |
| Me | H | Me | CF₃ | 3-Cl-2-pyridyl | Me | H |
| Me | H | Me | CF₃ | 3-Cl-2-pyridyl | Me | Cl |
| H | Me | Me | CF₃ | 3-Cl-2-pyridyl | Me | H |
| H | Me | Me | CF₃ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 4

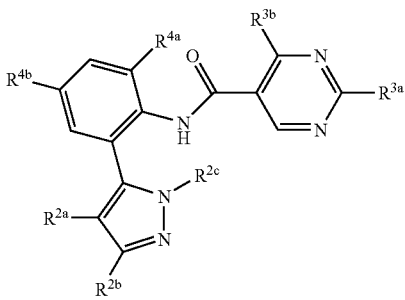

| R²ᵃ | R²ᵇ | R²ᶜ | R³ᵃ | R³ᵇ | R⁴ᵃ | R⁴ᵇ |
|---|---|---|---|---|---|---|
| H | H | H | CF₃ | 2-ClPh | Me | H |
| H | H | H | CF₃ | 2-ClPh | Me | Cl |
| H | H | H | CF₃ | 2-ClPh | Me | H |
| H | H | H | CF₃ | 2-ClPh | Me | H |
| H | H | H | CF₃ | 2-ClPh | Cl | H |
| H | H | H | CF₃ | 3-Cl-2-pyridyl | Cl | H |
| H | H | H | CF₃ | 3-Cl-2-pyridyl | Me | Br |
| H | H | H | CF₃ | Me | Me | Cl |
| H | H | H | CF₃ | Et | Me | Br |
| H | H | H | CF₃ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF₃ | 2-ClPh | Me | H |
| Me | H | H | CF₃ | 2-ClPh | Me | Cl |
| Me | H | H | CF₃ | 3-Cl-2-pyridyl | Me | H |
| Me | H | H | CF₃ | 3-Cl-2-pyridyl | Me | H |
| Me | H | H | CF₃ | 2-ClPh | Cl | H |
| Me | H | H | CF₃ | 3-Cl-2-pyridyl | Cl | H |
| Me | H | H | CF₃ | 3-Cl-2-pyridyl | Me | Br |

TABLE 4-continued

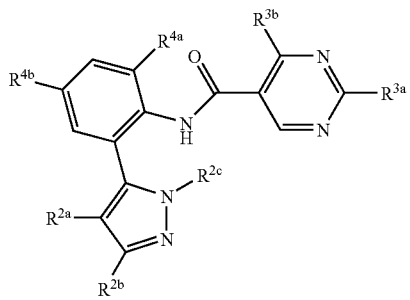

| R²ᵃ | R²ᵇ | R²ᶜ | R³ᵃ | R³ᵇ | R⁴ᵃ | R⁴ᵇ |
|---|---|---|---|---|---|---|
| Me | H | H | CF₃ | Me | Me | Cl |
| Me | H | H | CF₃ | Et | Me | Br |
| Me | H | H | CF₃ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF₃ | 2-ClPh | Me | H |
| H | Me | H | CF₃ | 2-ClPh | Me | Cl |
| H | Me | H | CF₃ | 3-Cl-2-pyridyl | Me | H |
| H | Me | H | CF₃ | 3-Cl-2-pyridyl | Me | H |
| H | Me | H | CF₃ | 2-ClPh | Cl | H |
| H | Me | H | CF₃ | 3-Cl-2-pyridyl | Cl | H |
| H | Me | H | CF₃ | 3-Cl-2-Pyridyl | Me | Br |
| H | Me | H | CF₃ | Me | Me | Cl |
| H | Me | H | CF₃ | Et | Me | Br |
| H | Me | H | CF₃ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF₃ | 2-ClPh | Me | H |
| Me | Me | H | CF₃ | 2-ClPh | Me | Cl |
| Me | Me | H | CF₃ | 2-ClPh | Me | H |
| Me | Me | H | CF₃ | 3-Cl-2-pyridyl | Me | H |
| Me | Me | H | CF₃ | 2-ClPh | Cl | H |
| Me | Me | H | CF₃ | 2-ClPh | Cl | H |
| Me | Me | H | CF₃ | 3-Cl-2-pyridyl | Me | Br |
| Me | Me | H | CF₃ | Me | Me | Cl |
| Me | Me | H | CF₃ | Et | Me | Br |
| Me | Me | H | CF₃ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF₃ | 2-ClPh | Me | H |
| H | H | Me | CF₃ | 2-ClPh | Me | Cl |
| H | H | Me | CF₃ | 3-Cl-2-pyridyl | Me | H |
| H | H | Me | CF₃ | 3-Cl-2-pyridyl | Me | Cl |
| Me | H | Me | CF₃ | 3-Cl-2-pyridyl | Me | H |
| Me | H | Me | CF₃ | 3-Cl-2-pyridyl | Me | Cl |
| H | Me | Me | CF₃ | 3-Cl-2-pyridyl | Me | H |
| H | Me | Me | CF₃ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 5

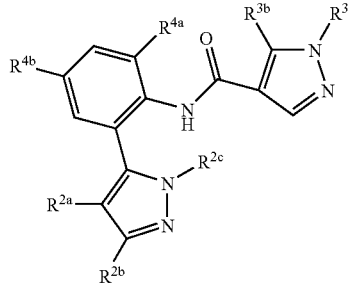

| R$^{2a}$ | R$^{2b}$ | R$^{2c}$ | R$^{3a}$ | R$^{3b}$ | R$^{4a}$ | R$^{4b}$ |
|---|---|---|---|---|---|---|
| H | H | H | CH$_2$CF$_3$ | 2-ClPh | Me | H |
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | H |
| H | H | H | CH$_2$CF$_3$ | 2-ClPh | Cl | H |
| H | H | H | CHF$_2$ | 3-Cl-2-pyridyl | Cl | H |
| H | H | H | CH$_2$CF$_3$ | 3-Cl-2-pyridyl | Me | Br |
| H | H | H | CH$_2$CF$_3$ | Me | Me | Cl |
| H | H | H | CH$_2$CF$_3$ | Et | Me | Br |
| H | H | H | CHF$_2$ | Ph | Me | Cl |
| H | H | H | CH$_2$CF$_3$ | 2-ClPh | Cl | H |
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | Cl |
| H | H | H | CH$_2$CF$_3$ | 3-Cl-2-pyridyl | Me | Br |
| H | H | H | CHF$_2$ | 2-ClPh | Cl | H |
| H | H | H | CH$_2$CF$_3$ | 3-Cl-2-pyridyl | Cl | H |
| Me | H | H | CH$_2$CF$_3$ | 2-ClPh | Me | H |
| Me | H | H | CH$_2$CF$_3$ | 2-ClPh | Me | Cl |
| Me | H | H | CH$_2$CF$_3$ | 3-Cl-2-pyridyl | Me | H |
| Me | H | H | CHF$_2$ | 3-Cl-2-pyridyl | Me | H |
| Me | H | H | CH$_2$CF$_3$ | 2-ClPh | Cl | H |
| Me | H | H | CH$_2$CF$_3$ | 3-Cl-2-pyridyl | Cl | H |
| Me | H | H | CHF$_2$ | 3-Cl-2-pyridyl | Me | Br |
| Me | H | H | CH$_2$CF$_3$ | Me | Me | Cl |
| Me | H | H | CH$_2$CF$_3$ | Et | Me | Br |
| Me | H | H | CH$_2$CF$_3$ | Ph | Me | Cl |
| Me | H | H | CH$_2$CF$_3$ | 2-ClPh | Cl | H |
| Me | H | H | CHF$_2$ | 2-ClPh | Me | Cl |
| Me | H | H | CH$_2$CF$_3$ | 3-Cl-2-pyridyl | Me | H |
| Me | H | H | CH$_2$CF$_3$ | 3-Cl-2-pyridyl | Me | Cl |
| Me | H | H | CH$_2$CF$_3$ | 3-Cl-2-pyridyl | Me | Br |
| Me | H | H | CH$_2$CF$_3$ | 2-ClPh | Cl | H |
| Me | H | H | CHF$_2$ | 3-Cl-2-pyridyl | Cl | H |
| H | Me | H | CH$_2$CF$_3$ | 2-ClPh | Me | H |
| H | Me | H | CH$_2$CF$_3$ | 2-ClPh | Me | Cl |
| H | Me | H | CH$_2$CF$_3$ | 3-Cl-2-pyridyl | Me | H |
| H | Me | H | CHF$_2$ | 3-Cl-2-pyridyl | Me | H |
| H | Me | H | CH$_2$CF$_3$ | 2-ClPh | Cl | H |
| H | Me | H | CH$_2$CF$_3$ | 3-Cl-2-pyridyl | Cl | H |
| H | Me | H | CHF$_2$ | 3-Cl-2-pyridyl | Me | Br |
| H | Me | H | CH$_2$CF$_3$ | Me | Me | Cl |
| H | Me | H | CH$_2$CF$_3$ | Et | Me | Br |
| H | Me | H | CH$_2$CF$_3$ | Ph | Me | Cl |
| H | Me | H | CHF$_2$ | 2-ClPh | Cl | H |
| H | Me | H | CH$_2$CF$_3$ | 2-ClPh | Me | Cl |
| H | Me | H | CH$_2$CF$_3$ | 2-ClPh | Me | H |
| H | Me | H | CHF$_2$ | 2-ClPh | Me | Cl |
| H | Me | H | CH$_2$CF$_3$ | 3-Cl-2-pyridyl | Me | Br |
| H | Me | H | CH$_2$CF$_3$ | 2-ClPh | Cl | H |
| H | Me | H | CH$_2$CF$_3$ | 2-ClPh | Cl | H |
| Me | Me | H | CHF$_2$ | 2-ClPh | Me | H |
| Me | Me | H | CH$_2$CF$_3$ | 2-ClPh | Me | Cl |
| Me | Me | H | CH$_2$CF$_3$ | 2-ClPh | Me | H |
| Me | Me | H | CH$_2$CF$_3$ | 3-Cl-2-pyridyl | Me | H |
| Me | Me | H | CH$_2$CF$_3$ | 2-ClPh | Cl | H |
| Me | Me | H | CHF$_2$ | 2-ClPh | Cl | H |
| Me | Me | H | CH$_2$CF$_3$ | 3-Cl-2-pyridyl | Me | Br |
| Me | Me | H | CH$_2$CF$_3$ | Me | Me | Cl |
| Me | Me | H | CH$_2$CF$_3$ | Et | Me | Br |
| Me | Me | H | CH$_2$CF$_3$ | Ph | Me | Cl |
| Me | Me | H | CH$_2$CF$_3$ | 2-ClPh | Cl | H |

TABLE 5-continued

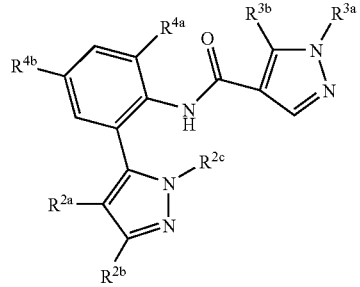

| R$^{2a}$ | R$^{2b}$ | R$^{2c}$ | R$^{3a}$ | R$^{3b}$ | R$^{4a}$ | R$^{4b}$ |
|---|---|---|---|---|---|---|
| Me | Me | H | CHF$_2$ | 2-ClPh | Me | Cl |
| Me | Me | H | CH$_2$CF$_3$ | 3-Cl-2-pyridyl | Me | H |
| Me | Me | H | CH$_2$CF$_3$ | 3-Cl-2-pyridyl | Me | Cl |
| Me | Me | H | CH$_2$CF$_3$ | 3-Cl-2-pyridyl | Me | Br |
| Me | Me | H | CHF$_2$ | 2-ClPh | Cl | H |
| Me | Me | H | CH$_2$CF$_3$ | 3-Cl-2-pyridyl | Cl | H |
| H | H | Me | CH$_2$CF$_3$ | 2-ClPh | Me | H |
| H | H | Me | CH$_2$CF$_3$ | 2-ClPh | Me | Cl |
| H | H | Me | CH$_2$CF$_3$ | 3-Cl-2-pyridyl | Me | H |
| H | H | Me | CH$_2$CF$_3$ | 3-Cl-2-pyridyl | Me | Cl |
| Me | H | Me | CH$_2$CF$_3$ | 3-Cl-2-pyridyl | Me | H |
| Me | H | Me | CH$_2$CF$_3$ | 3-Cl-2-pyridyl | Me | Cl |
| H | Me | Me | CH$_2$CF$_3$ | 3-Cl-2-pyridyl | Me | H |
| H | Me | Me | CH$_2$CF$_3$ | 3-Cl-2-pyridyl | Me | Cl |
| H | Me | Me | CH$_2$CF$_3$ | 3-Cl-2-pyridyl | Me | H |
| H | Me | Me | CH$_2$CF$_3$ | 3-Cl-2-pyridyl | Me | Cl |

TABLE 6

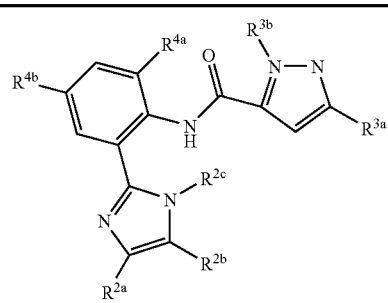

| R$^{2a}$ | R$^{2b}$ | R$^{2c}$ | R$^{3a}$ | R$^{3b}$ | R$^{4a}$ | R$^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 3-Cl-2-pyridyl | Me | H |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 3-Cl-2-pyridyl | Me | H |
| Me | H | H | CF$_3$ | 3-Cl-2-pyridyl | Me | Cl |
| Me | H | H | CF$_3$ | 2-ClPh | Cl | H |
| Me | H | H | CF$_3$ | 3-Cl-2-pyridyl | Cl | H |
| Me | H | H | CF$_3$ | 3-Cl-2-pyridyl | Me | Br |

TABLE 6-continued

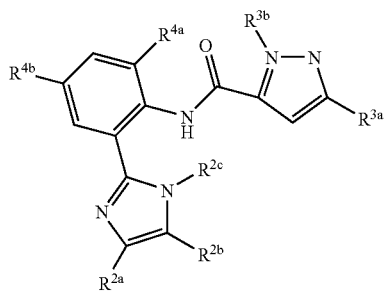

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | Cl |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 3-Cl-2-pyridyl | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 3-Cl-2-pyridyl | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF$_3$ | 2-ClPh | Me | H |
| H | H | Me | CF$_3$ | 2-ClPh | Me | Cl |
| H | H | Me | CF$_3$ | 3-Cl-2-pyridyl | Me | H |
| H | H | Me | CF$_3$ | 3-Cl-2-pyridyl | Me | Cl |
| Me | H | Me | CF$_3$ | 3-Cl-2-pyridyl | Me | H |
| Me | H | Me | CF$_3$ | 3-Cl-2-pyridyl | Me | Cl |
| H | Me | Me | CF$_3$ | 3-Cl-2-pyridyl | Me | H |
| H | Me | Me | CF$_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 7

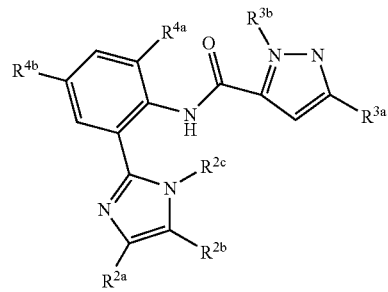

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 2-ClPh | Me | H |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 2-ClPh | Me | H |
| Me | H | H | CF$_3$ | 3-Cl-2-pyridyl | Me | H |
| Me | H | H | CF$_3$ | 2-ClPh | Cl | H |
| Me | H | H | CF$_3$ | 3-Cl-2-pyridyl | Cl | H |
| Me | H | H | CF$_3$ | 3-Cl-2-pyridyl | Me | Br |
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | H |
| H | Me | H | CF$_3$ | 2-ClPh | Cl | H |
| H | Me | H | CF$_3$ | 3-Cl-2-pyridyl | Cl | H |

TABLE 7-continued

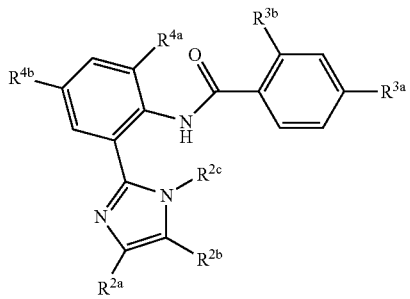

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF$_3$ | 2-ClPh | Me | H |
| H | H | Me | CF$_3$ | 2-ClPh | Me | Cl |
| H | H | Me | CF$_3$ | 3-Cl-2-pyridyl | Me | H |
| H | H | Me | CF$_3$ | 3-Cl-2-pyridyl | Me | Cl |
| Me | H | Me | CF$_3$ | 3-Cl-2-pyridyl | Me | H |
| Me | H | Me | CF$_3$ | 3-Cl-2-pyridyl | Me | Cl |
| H | Me | Me | CF$_3$ | 3-Cl-2-pyridyl | Me | H |
| H | Me | Me | CF$_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 8

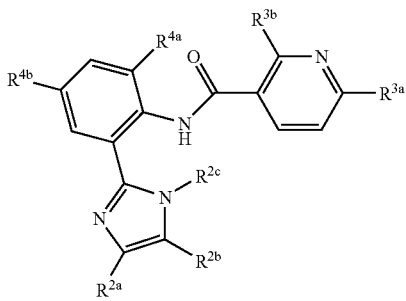

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |

TABLE 8-continued

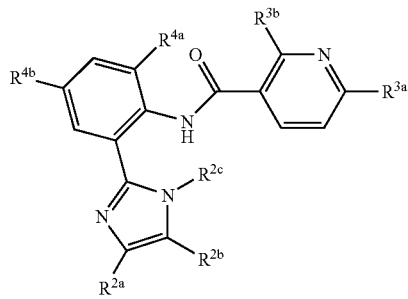

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 3-Cl-2-pyridyl | Me | H |
| Me | H | H | CF$_3$ | 3-Cl-2-pyridyl | Me | H |
| Me | H | H | CF$_3$ | 2-ClPh | Cl | H |
| Me | H | H | CF$_3$ | 3-Cl-2-pyridyl | Cl | H |
| Me | H | H | CF$_3$ | 3-Cl-2-pyridyl | Me | Br |
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | Cl |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |

TABLE 8-continued

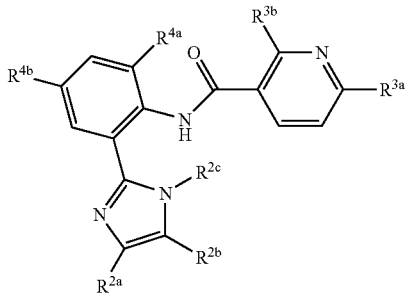

| R2a | R2b | R2c | R3a | R3b | R4a | R4b |
|---|---|---|---|---|---|---|
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 9

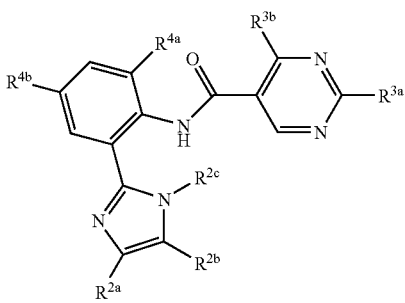

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 2-ClPh | Me | H |
| H | H | H | CF3 | 2-ClPh | Me | Cl |
| H | H | H | CF3 | 2-ClPh | Me | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |
| Me | H | H | CF3 | 3-Cl-2-pyridyl | Cl | H |
| Me | H | H | CF3 | 3-Cl-2-pyridyl | Me | Br |
| Me | H | H | CF3 | Me | Me | Cl |
| Me | H | H | CF3 | Et | Me | Br |

TABLE 9-continued

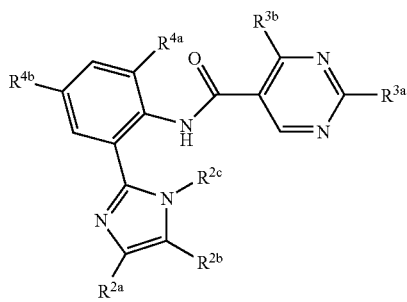

| R2a | R2b | R2c | R3a | R3b | R4a | R4b |
|---|---|---|---|---|---|---|
| Me | H | H | CF3 | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF3 | 2-ClPh | Me | H |
| H | Me | H | CF3 | 2-ClPh | Me | Cl |
| H | Me | H | CF3 | 3-Cl-2-pyridyl | Me | H |
| H | Me | H | CF3 | 3-Cl-2-pyridyl | Me | H |
| H | Me | H | CF3 | 2-ClPh | Cl | H |
| H | Me | H | CF3 | 3-Cl-2-pyridyl | Cl | H |
| H | Me | H | CF3 | 3-Cl-2-pyridyl | Me | Br |
| H | Me | H | CF3 | Me | Me | Cl |
| H | Me | H | CF3 | Et | Me | Br |
| H | Me | H | CF3 | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF3 | 2-ClPh | Me | H |
| Me | Me | H | CF3 | 2-ClPh | Me | Cl |
| Me | Me | H | CF3 | 2-ClPh | Me | H |
| Me | Me | H | CF3 | 3-Cl-2-pyridyl | Me | H |
| Me | Me | H | CF3 | 2-ClPh | Cl | H |
| Me | Me | H | CF3 | 2-ClPh | Cl | H |
| Me | Me | H | CF3 | 3-Cl-2-pyridyl | Me | Br |
| Me | Me | H | CF3 | Me | Me | Cl |
| Me | Me | H | CF3 | Et | Me | Br |
| Me | Me | H | CF3 | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 10

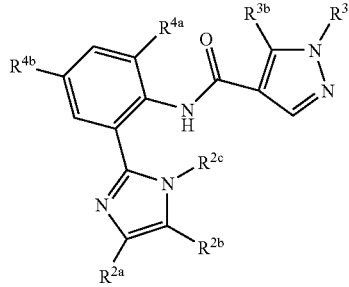

| R$^{2a}$ | R$^{2b}$ | R$^{2c}$ | R$^{3a}$ | R$^{3b}$ | R$^{4a}$ | R$^{4b}$ |
|---|---|---|---|---|---|---|
| H | H | H | CH$_2$CF$_3$ | 2-ClPh | Me | H |
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | H |
| H | H | H | CH$_2$CF$_3$ | 2-ClPh | Cl | H |
| H | H | H | CHF$_2$ | 3-Cl-2-pyridyl | Cl | H |
| H | H | H | CH$_2$CF$_3$ | 3-Cl-2-pyridyl | Me | Br |
| H | H | H | CH$_2$CF$_3$ | Me | Me | Cl |
| H | H | H | CH$_2$CF$_3$ | Et | Me | Br |
| H | H | H | CHF$_2$ | Ph | Me | Cl |
| H | H | H | CH$_2$CF$_3$ | 2-ClPh | Cl | H |
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | Cl |
| H | H | H | CH$_2$CF$_3$ | 3-Cl-2-pyridyl | Me | Br |
| H | H | H | CHF$_2$ | 2-ClPh | Cl | H |
| H | H | H | CH$_2$CF$_3$ | 3-Cl-2-pyridyl | Cl | H |
| Me | H | H | CH$_2$CF$_3$ | 2-ClPh | Me | H |
| Me | H | H | CH$_2$CF$_3$ | 2-ClPh | Me | Cl |
| Me | H | H | CH$_2$CF$_3$ | 3-Cl-2-pyridyl | Me | H |
| Me | H | H | CHF$_2$ | 3-Cl-2-pyridyl | Me | H |
| Me | H | H | CH$_2$CF$_3$ | 2-ClPh | Cl | H |
| Me | H | H | CH$_2$CF$_3$ | 3-Cl-2-pyridyl | Cl | H |
| Me | H | H | CHF$_2$ | 3-Cl-2-pyridyl | Me | Br |
| Me | H | H | CH$_2$CF$_3$ | Me | Me | Cl |
| Me | H | H | CH$_2$CF$_3$ | Et | Me | Br |
| Me | H | H | CH$_2$CF$_3$ | Ph | Me | Cl |
| Me | H | H | CH$_2$CF$_3$ | 2-ClPh | Cl | H |
| Me | H | H | CHF$_2$ | 2-ClPh | Me | Cl |
| Me | H | H | CH$_2$CF$_3$ | 3-Cl-2-pyridyl | Me | H |
| Me | H | H | CH$_2$CF$_3$ | 3-Cl-2-pyridyl | Me | Cl |
| Me | H | H | CH$_2$CF$_3$ | 3-Cl-2-pyridyl | Me | Br |
| Me | H | H | CH$_2$CF$_3$ | 2-ClPh | Cl | H |
| Me | H | H | CHF$_2$ | 3-Cl-2-pyridyl | Cl | H |
| H | Me | H | CH$_2$CF$_3$ | 2-ClPh | Me | H |
| H | Me | H | CH$_2$CF$_3$ | 2-ClPh | Me | Cl |
| H | Me | H | CH$_2$CF$_3$ | 3-Cl-2-pyridyl | Me | H |
| H | Me | H | CHF$_2$ | 3-Cl-2-pyridyl | Me | H |
| H | Me | H | CH$_2$CF$_3$ | 2-ClPh | Cl | H |
| H | Me | H | CH$_2$CF$_3$ | 3-Cl-2-pyridyl | Cl | H |
| H | Me | H | CHF$_2$ | 3-Cl-2-pyridyl | Me | Br |
| H | Me | H | CH$_2$CF$_3$ | Me | Me | Cl |
| H | Me | H | CH$_2$CF$_3$ | Et | Me | Br |
| H | Me | H | CH$_2$CF$_3$ | Ph | Me | Cl |
| H | Me | H | CHF$_2$ | 2-ClPh | Cl | H |
| H | Me | H | CH$_2$CF$_3$ | 2-ClPh | Me | Cl |
| H | Me | H | CH$_2$CF$_3$ | 2-ClPh | Me | H |
| H | Me | H | CHF$_2$ | 2-ClPh | Me | Cl |
| H | Me | H | CH$_2$CF$_3$ | 3-Cl-2-pyridyl | Me | Br |
| H | Me | H | CH$_2$CF$_3$ | 2-ClPh | Cl | H |
| H | Me | H | CH$_2$CF$_3$ | 2-ClPh | Cl | H |
| Me | Me | H | CHF$_2$ | 2-ClPh | Me | H |
| Me | Me | H | CH$_2$CF$_3$ | 2-ClPh | Me | Cl |
| Me | Me | H | CH$_2$CF$_3$ | 2-ClPh | Me | H |
| Me | Me | H | CH$_2$CF$_3$ | 3-Cl-2-pyridyl | Me | H |
| Me | Me | H | CH$_2$CF$_3$ | 2-ClPh | Cl | H |
| Me | Me | H | CHF$_2$ | 2-ClPh | Cl | H |
| Me | Me | H | CH$_2$CF$_3$ | 3-Cl-2-pyridyl | Me | Br |
| Me | Me | H | CH$_2$CF$_3$ | Me | Me | Cl |
| Me | Me | H | CH$_2$CF$_3$ | Et | Me | Br |
| Me | Me | H | CH$_2$CF$_3$ | Ph | Me | Cl |
| Me | Me | H | CH$_2$CF$_3$ | 2-ClPh | Cl | H |

TABLE 10-continued

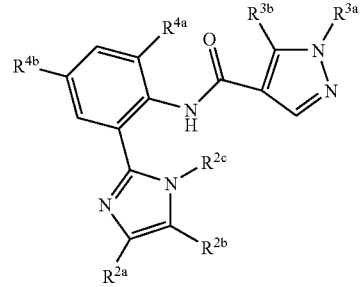

| R$^{2a}$ | R$^{2b}$ | R$^{2c}$ | R$^{3a}$ | R$^{3b}$ | R$^{4a}$ | R$^{4b}$ |
|---|---|---|---|---|---|---|
| Me | Me | H | CHF$_2$ | 2-ClPh | Me | Cl |
| Me | Me | H | CH$_2$CF$_3$ | 3-Cl-2-pyridyl | Me | H |
| Me | Me | H | CH$_2$CF$_3$ | 3-Cl-2-pyridyl | Me | Cl |
| Me | Me | H | CH$_2$CF$_3$ | 3-Cl-2-pyridyl | Me | Br |
| Me | Me | H | CHF$_2$ | 2-ClPh | Cl | H |
| Me | Me | H | CH$_2$CF$_3$ | 3-Cl-2-pyridyl | Cl | H |
| H | H | Me | CH$_2$CF$_3$ | 2-ClPh | Me | H |
| H | H | Me | CH$_2$CF$_3$ | 2-ClPh | Me | Cl |
| H | H | Me | CH$_2$CF$_3$ | 3-Cl-2-pyridyl | Me | H |
| H | H | Me | CH$_2$CF$_3$ | 3-Cl-2-pyridyl | Me | Cl |
| Me | H | Me | CH$_2$CF$_3$ | 3-Cl-2-pyridyl | Me | H |
| Me | H | Me | CH$_2$CF$_3$ | 3-Cl-2-pyridyl | Me | Cl |
| H | Me | Me | CH$_2$CF$_3$ | 3-Cl-2-pyridyl | Me | H |
| H | Me | Me | CH$_2$CF$_3$ | 3-Cl-2-pyridyl | Me | Cl |
| H | Me | Me | CH$_2$CF$_3$ | 3-Cl-2-pyridyl | Me | H |
| H | Me | Me | CH$_2$CF$_3$ | 3-Cl-2-pyridyl | Me | Cl |

TABLE 11

| R$^{2a}$ | R$^{2b}$ | R$^{3a}$ | R$^{3b}$ | R$^{4a}$ | R$^{4b}$ |
|---|---|---|---|---|---|
| H | H | CF$_3$ | 2-ClPh | Me | H |
| H | H | CF$_3$ | 2-ClPh | Me | Cl |
| H | H | CF$_3$ | 2-ClPh | Cl | H |
| H | H | CF$_3$ | Me | Me | Cl |
| H | H | CF$_3$ | Et | Me | Br |
| H | H | CF$_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF$_3$ | 2-ClPh | Me | H |
| Me | H | CF$_3$ | 2-ClPh | Me | Cl |
| Me | H | CF$_3$ | 2-ClPh | Cl | H |
| Me | H | CF$_3$ | Me | Me | Cl |
| Me | H | CF$_3$ | Et | Me | Br |
| Me | H | CF$_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF$_3$ | 2-ClPh | Me | H |
| H | Me | CF$_3$ | 2-ClPh | Me | Cl |
| H | Me | CF$_3$ | 2-ClPh | Cl | H |
| H | Me | CF$_3$ | Me | Me | Cl |

TABLE 11-continued

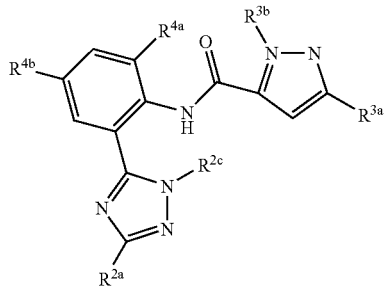

| $R^{2a}$ | $R^{2b}$ | $R^{3a}$ | $R^{3b}$ | $R^{4a}$ | $R^{4b}$ |
|---|---|---|---|---|---|
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |
| H | Me | CF₃ | 3-Cl-2-pyridyl | Cl | H |
| H | Me | CF₃ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF₃ | 3-Cl-2-pyridyl | Me | H |
| Me | Me | CF₃ | 3-Cl-2-pyridyl | Me | Cl |
| Me | Me | CF₃ | 3-Cl-2-pyridyl | Cl | H |
| Me | Me | CF₃ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 12

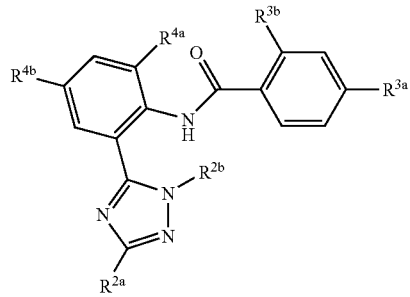

| $R^{2a}$ | $R^{2b}$ | $R^{3a}$ | $R^{3b}$ | $R^{4a}$ | $R^{4b}$ |
|---|---|---|---|---|---|
| H | H | CF₃ | 2-ClPh | Me | H |
| H | H | CF₃ | 2-ClPh | Me | Cl |
| H | H | CF₃ | 2-ClPh | Cl | H |
| H | H | CF₃ | Me | Me | Cl |
| H | H | CF₃ | Et | Me | Br |
| H | H | CF₃ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF₃ | 2-ClPh | Me | H |
| Me | H | CF₃ | 2-ClPh | Me | Cl |
| Me | H | CF₃ | 2-ClPh | Cl | H |
| Me | H | CF₃ | Me | Me | Cl |
| Me | H | CF₃ | Et | Me | Br |
| Me | H | CF₃ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF₃ | 2-ClPh | Me | H |
| H | Me | CF₃ | 2-ClPh | Me | Cl |
| H | Me | CF₃ | 2-ClPh | Cl | H |
| H | Me | CF₃ | Me | Me | Cl |
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |

TABLE 12-continued

| $R^{2a}$ | $R^{2b}$ | $R^{3a}$ | $R^{3b}$ | $R^{4a}$ | $R^{4b}$ |
|---|---|---|---|---|---|
| H | Me | $CF_3$ | 3-Cl-2-pyridyl | Cl | H |
| H | Me | $CF_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | $CF_3$ | 3-Cl-2-pyridyl | Me | H |
| Me | Me | $CF_3$ | 3-Cl-2-pyridyl | Me | Cl |
| Me | Me | $CF_3$ | 3-Cl-2-pyridyl | Cl | H |
| Me | Me | $CF_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 13

| $R^{2a}$ | $R^{2b}$ | $R^{3a}$ | $R^{3b}$ | $R^{4a}$ | $R^{4b}$ |
|---|---|---|---|---|---|
| H | H | $CF_3$ | 2-ClPh | Me | H |
| H | H | $CF_3$ | 2-ClPh | Me | Cl |
| H | H | $CF_3$ | 2-ClPh | Cl | H |
| H | H | $CF_3$ | Me | Me | Cl |
| H | H | $CF_3$ | Et | Me | Br |
| H | H | $CF_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | $CF_3$ | 2-ClPh | Me | H |
| Me | H | $CF_3$ | 2-ClPh | Me | Cl |
| Me | H | $CF_3$ | 2-ClPh | Cl | H |
| Me | H | $CF_3$ | Me | Me | Cl |
| Me | H | $CF_3$ | Et | Me | Br |
| Me | H | $CF_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | $CF_3$ | 2-ClPh | Me | H |
| H | Me | $CF_3$ | 2-ClPh | Me | Cl |

TABLE 13-continued

| $R^{2a}$ | $R^{2b}$ | $R^{3a}$ | $R^{3b}$ | $R^{4a}$ | $R^{4b}$ |
|---|---|---|---|---|---|
| H | Me | $CF_3$ | 2-ClPh | Cl | H |
| H | Me | $CF_3$ | Me | Me | Cl |
| H | Me | $CF_3$ | Et | Me | Br |
| H | Me | $CF_3$ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | $CF_3$ | 2-ClPh | Me | H |
| Me | Me | $CF_3$ | 2-ClPh | Me | Cl |
| Me | Me | $CF_3$ | 2-ClPh | Cl | H |
| Me | Me | $CF_3$ | Me | Me | Cl |
| Me | Me | $CF_3$ | Et | Me | Br |
| Me | Me | $CF_3$ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | $CF_3$ | 3-Cl-2-pyridyl | Me | H |
| H | H | $CF_3$ | 3-Cl-2-pyridyl | Me | Cl |
| H | H | $CF_3$ | 3-Cl-2-pyridyl | Cl | H |
| H | H | $CF_3$ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | $CF_3$ | 3-Cl-2-pyridyl | Me | H |
| Me | H | $CF_3$ | 3-Cl-2-pyridyl | Me | Cl |
| Me | H | $CF_3$ | 3-Cl-2-pyridyl | Cl | H |
| Me | H | $CF_3$ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | $CF_3$ | 3-Cl-2-pyridyl | Me | H |
| H | Me | $CF_3$ | 3-Cl-2-pyridyl | Me | Cl |
| H | Me | $CF_3$ | 3-Cl-2-pyridyl | Cl | H |
| H | Me | $CF_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | $CF_3$ | 3-Cl-2-pyridyl | Me | H |
| Me | Me | $CF_3$ | 3-Cl-2-pyridyl | Me | Cl |
| Me | Me | $CF_3$ | 3-Cl-2-pyridyl | Cl | H |
| Me | Me | $CF_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 14

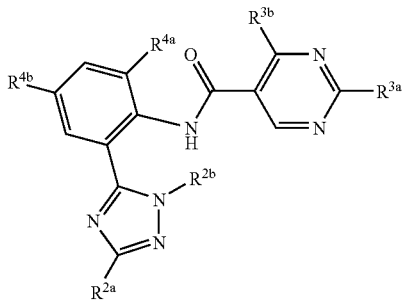

| $R^{2a}$ | $R^{2b}$ | $R^{3a}$ | $R^{3b}$ | $R^{4a}$ | $R^{4b}$ |
|---|---|---|---|---|---|
| H | H | $CF_3$ | 2-ClPh | Me | H |
| H | H | $CF_3$ | 2-ClPh | Me | Cl |
| H | H | $CF_3$ | 2-ClPh | Cl | H |
| H | H | $CF_3$ | Me | Me | Cl |
| H | H | $CF_3$ | Et | Me | Br |
| H | H | $CF_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | $CF_3$ | 2-ClPh | Me | H |
| Me | H | $CF_3$ | 2-ClPh | Me | Cl |
| Me | H | $CF_3$ | 2-ClPh | Cl | H |
| Me | H | $CF_3$ | Me | Me | Cl |
| Me | H | $CF_3$ | Et | Me | Br |
| Me | H | $CF_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | $CF_3$ | 2-ClPh | Me | H |
| H | Me | $CF_3$ | 2-ClPh | Me | Cl |
| H | Me | $CF_3$ | 2-ClPh | Cl | H |
| H | Me | $CF_3$ | Me | Me | Cl |
| H | Me | $CF_3$ | Et | Me | Br |
| H | Me | $CF_3$ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | $CF_3$ | 2-ClPh | Me | H |
| Me | Me | $CF_3$ | 2-ClPh | Me | Cl |
| Me | Me | $CF_3$ | 2-ClPh | Cl | H |
| Me | Me | $CF_3$ | Me | Me | Cl |
| Me | Me | $CF_3$ | Et | Me | Br |
| Me | Me | $CF_3$ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | $CF_3$ | 2-Cl-2-pyridyl | Me | H |
| H | H | $CF_3$ | 3-Cl-2-pyridyl | Me | Cl |
| H | H | $CF_3$ | 3-Cl-2-pyridyl | Cl | H |
| H | H | $CF_3$ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | $CF_3$ | 3-Cl-2-pyridyl | Me | H |
| Me | H | $CF_3$ | 3-Cl-2-pyridyl | Me | Cl |
| Me | H | $CF_3$ | 3-Cl-2-pyridyl | Cl | H |
| Me | H | $CF_3$ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | $CF_3$ | 3-Cl-2-pyridyl | Me | H |

TABLE 14-continued

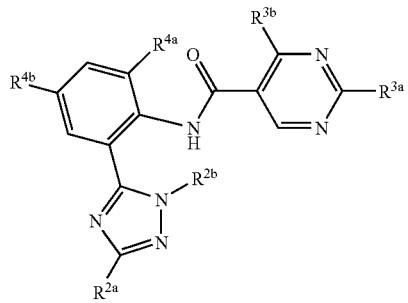

| $R^{2a}$ | $R^{2b}$ | $R^{3a}$ | $R^{3b}$ | $R^{4a}$ | $R^{4b}$ |
|---|---|---|---|---|---|
| H | Me | $CF_3$ | 3-Cl-2-pyridyl | Me | Cl |
| H | Me | $CF_3$ | 3-Cl-2-pyridyl | Cl | H |
| H | Me | $CF_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | $CF_3$ | 3-Cl-2-pyridyl | Me | H |
| Me | Me | $CF_3$ | 3-Cl-2-pyridyl | Me | Cl |
| Me | Me | $CF_3$ | 3-Cl-2-pyridyl | Cl | H |
| Me | Me | $CF_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 15

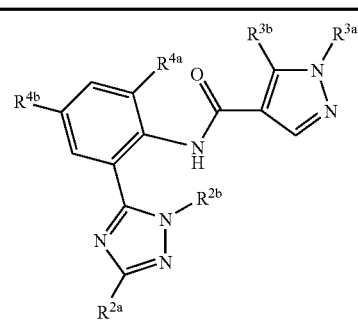

| $R^{2a}$ | $R^{2b}$ | $R^{3a}$ | $R^{3b}$ | $R^{4a}$ | $R^{4b}$ |
|---|---|---|---|---|---|
| H | H | $CH_2CF_3$ | 2-ClPh | Me | H |
| H | H | $CH_2CF_3$ | 2-ClPh | Me | Cl |
| H | H | $CH_2CF_3$ | 2-ClPh | Cl | H |
| H | H | $CH_2CF_3$ | 2-ClPh | Me | Br |
| H | H | $CH_2CF_3$ | 3-Cl-2-pyridyl | Me | H |
| H | H | $CH_2CF_3$ | 3-Cl-2-pyridyl | Cl | H |
| H | H | $CH_2CF_3$ | 3-Cl-2-pyridyl | Me | Br |
| H | H | $CH_2CF_3$ | 3-Cl-2-pyridyl | Me | Cl |
| H | H | $CH_2CF_3$ | Me | Me | Cl |
| H | H | $CH_2CF_3$ | Et | Me | Br |
| H | H | $CH_2CF_3$ | Ph | Me | Cl |
| H | H | $CHF_2$ | 2-ClPh | Me | H |
| H | H | $CHF_2$ | 2-ClPh | Me | Cl |
| H | H | $CHF_2$ | 2-ClPh | Cl | H |
| H | H | $CHF_2$ | 2-ClPh | Me | Br |
| H | H | $CHF_2$ | 3-Cl-2-pyridyl | Me | H |
| H | H | $CHF_2$ | 3-Cl-2-pyridyl | Cl | H |
| H | H | $CHF_2$ | 3-Cl-2-pyridyl | Me | Br |
| H | H | $CHF_2$ | 3-Cl-2-pyridyl | Me | Cl |
| Me | H | $CH_2CF_3$ | 2-ClPh | Me | H |

TABLE 15-continued

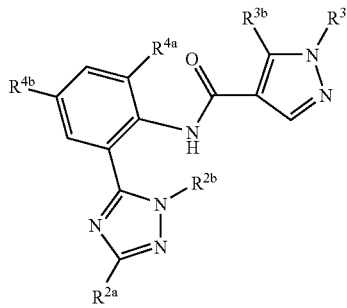

| R²ᵃ | R²ᵇ | R³ᵃ | R³ᵇ | R⁴ᵃ | R⁴ᵇ |
|---|---|---|---|---|---|
| Me | H | CH₂CF₃ | 2-ClPh | Me | Cl |
| Me | H | CH₂CF₃ | 2-ClPh | Cl | H |
| Me | H | CH₂CF₃ | 2-ClPh | Me | Br |
| Me | H | CH₂CF₃ | 3-Cl-2-pyridyl | Me | H |
| Me | H | CH₂CF₃ | 3-Cl-2-pyridyl | Cl | H |
| Me | H | CH₂CF₃ | 3-Cl-2-pyridyl | Me | Br |
| Me | H | CH₂CF₃ | 3-Cl-2-pyridyl | Me | Cl |
| Me | H | CH₂CF₃ | Me | Me | Cl |
| Me | H | CH₂CF₃ | Et | Me | Br |
| Me | H | CH₂CF₃ | Ph | Me | Cl |
| Me | H | CHF₂ | 2-ClPh | Me | H |
| Me | H | CHF₂ | 2-ClPh | Me | Cl |
| Me | H | CHF₂ | 2-ClPh | Cl | H |
| Me | H | CHF₂ | 2-ClPh | Me | Br |
| Me | H | CHF₂ | 3-Cl-2-pyridyl | Me | H |
| Me | H | CHF₂ | 3-Cl-2-pyridyl | Cl | H |
| Me | H | CHF₂ | 3-Cl-2-pyridyl | Me | Br |
| Me | H | CHF₂ | 3-Cl-2-pyridyl | Me | Cl |
| H | Me | CH₂CF₃ | 2-ClPh | Me | H |
| H | Me | CH₂CF₃ | 2-ClPh | Me | Cl |
| H | Me | CH₂CF₃ | 2-ClPh | Cl | H |
| H | Me | CH₂CF₃ | 2-ClPh | Me | Br |
| H | Me | CH₂CF₃ | 3-Cl-2-pyridyl | Me | H |
| H | Me | CH₂CF₃ | 3-Cl-2-pyridyl | Cl | H |
| H | Me | CH₂CF₃ | 3-Cl-2-pyridyl | Me | Br |
| H | Me | CH₂CF₃ | 3-Cl-2-pyridyl | Me | Cl |
| H | Me | CH₂CF₃ | Me | Me | Cl |
| H | Me | CH₂CF₃ | Et | Me | Br |
| H | Me | CH₂CF₃ | Ph | Me | Cl |
| H | Me | CHF₂ | 2-ClPh | Me | H |
| H | Me | CHF₂ | 2-ClPh | Me | Cl |
| H | Me | CHF₂ | 2-ClPh | Cl | H |
| H | Me | CHF₂ | 2-ClPh | Me | Br |
| H | Me | CHF₂ | 3-Cl-2-pyridyl | Me | H |
| H | Me | CHF₂ | 3-Cl-2-pyridyl | Cl | H |
| H | Me | CHF₂ | 3-Cl-2-pyridyl | Me | Br |
| H | Me | CHF₂ | 3-Cl-2-pyridyl | Me | Cl |
| Me | Me | CH₂CF₃ | 2-ClPh | Me | H |
| Me | Me | CH₂CF₃ | 2-ClPh | Me | Cl |
| Me | Me | CH₂CF₃ | 2-ClPh | Cl | H |
| Me | Me | CH₂CF₃ | 2-ClPh | Me | Br |
| Me | Me | CH₂CF₃ | 3-Cl-2-pyridyl | Me | H |
| Me | Me | CH₂CF₃ | 3-Cl-2-pyridyl | Cl | H |
| Me | Me | CH₂CF₃ | 3-Cl-2-pyridyl | Me | Br |
| Me | Me | CH₂CF₃ | 3-Cl-2-pyridyl | Me | Cl |
| Me | Me | CH₂CF₃ | Me | Me | Cl |
| Me | Me | CH₂CF₃ | Et | Me | Br |
| Me | Me | CH₂CF₃ | Ph | Me | Cl |
| Me | Me | CHF₂ | 2-ClPh | Me | H |
| Me | Me | CHF₂ | 2-ClPh | Me | Cl |
| Me | Me | CHF₂ | 2-ClPh | Cl | H |
| Me | Me | CHF₂ | 2-ClPh | Me | Br |
| Me | Me | CHF₂ | 3-Cl-2-pyridyl | Me | H |
| Me | Me | CHF₂ | 3-Cl-2-pyridyl | Cl | H |
| Me | Me | CHF₂ | 3-Cl-2-pyridyl | Me | Br |
| Me | Me | CHF₂ | 3-Cl-2-pyridyl | Me | Cl |

TABLE 16

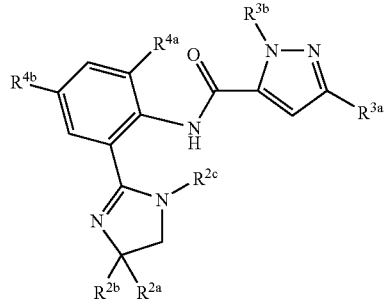

| R²ᵃ | R²ᵇ | R²ᶜ | R³ᵃ | R³ᵇ | R⁴ᵃ | R⁴ᵇ |
|---|---|---|---|---|---|---|
| H | H | H | CF₃ | 2-ClPh | Me | H |
| H | H | H | CF₃ | 2-ClPh | Me | Cl |
| H | H | H | CF₃ | 3-Cl-2-pyridyl | Me | H |
| H | H | H | CF₃ | 3-Cl-2-pyridyl | Me | Cl |
| H | H | H | CF₃ | 2-ClPh | Cl | H |
| H | H | H | CF₃ | 3-Cl-2-pyridyl | Cl | H |
| H | H | H | CF₃ | 3-Cl-2-pyridyl | Me | Br |
| H | H | H | CF₃ | Me | Me | Cl |
| H | H | H | CF₃ | Et | Me | Br |
| H | H | H | CF₃ | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF₃ | 2-ClPh | Me | H |
| Me | H | H | CF₃ | 2-ClPh | Me | Cl |
| Me | H | H | CF₃ | 3-Cl-2-pyridyl | Me | H |
| Me | H | H | CF₃ | 3-Cl-2-pyridyl | Me | Cl |
| Me | H | H | CF₃ | 2-ClPh | Cl | H |
| Me | H | H | CF₃ | 3-Cl-2-pyridyl | Cl | H |
| Me | H | H | CF₃ | 3-Cl-2-pyridyl | Me | Br |
| Me | H | H | CF₃ | Me | Me | Cl |
| Me | H | H | CF₃ | Et | Me | Br |
| Me | H | H | CF₃ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF₃ | 2-ClPh | Me | H |
| H | Me | H | CF₃ | 2-ClPh | Me | Cl |
| H | Me | H | CF₃ | 3-Cl-2-pyridyl | Me | H |
| H | Me | H | CF₃ | 3-Cl-2-pyridyl | Me | Cl |
| H | Me | H | CF₃ | 2-ClPh | Cl | H |
| H | Me | H | CF₃ | 3-Cl-2-pyridyl | Cl | H |
| H | Me | H | CF₃ | 3-Cl-2-pyridyl | Me | Br |
| H | Me | H | CF₃ | Me | Me | Cl |
| H | Me | H | CF₃ | Et | Me | Br |
| H | Me | H | CF₃ | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | CF₃ | 2-ClPh | Me | H |
| Me | Me | H | CF₃ | 2-ClPh | Me | Cl |
| Me | Me | H | CF₃ | 3-Cl-2-pyridyl | Me | H |
| Me | Me | H | CF₃ | 3-Cl-2-pyridyl | Me | Cl |
| Me | Me | H | CF₃ | 2-ClPh | Cl | H |
| Me | Me | H | CF₃ | 3-Cl-2-pyridyl | Cl | H |
| Me | Me | H | CF₃ | 3-Cl-2-pyridyl | Me | Br |
| Me | Me | H | CF₃ | Me | Me | Cl |
| Me | Me | H | CF₃ | Et | Me | Br |
| Me | Me | H | CF₃ | Ph | Me | Cl |

TABLE 16-continued

[Structure: pyrazole carboxamide with R3a, R3b on pyrazole; R4a, R4b on phenyl ring; N-H amide linked to phenyl bearing imidazoline with R2a, R2b, R2c substituents]

| R2a | R2b | R2c | R3a | R3b | R4a | R4b |
|---|---|---|---|---|---|---|
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 17

[Structure: benzamide with R3a, R3b on benzoyl phenyl ring; R4a, R4b on aniline phenyl ring; N-H amide linked to phenyl bearing imidazoline with R2a, R2b, R2c substituents]

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 2-ClPh | Me | H |
| H | H | H | CF3 | 2-ClPh | Me | H |
| H | H | H | CF3 | 2-ClPh | Cl | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 2-ClPh | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |

TABLE 17-continued

| R2a | R2b | R2c | R3a | R3b | R4a | R4b |
|---|---|---|---|---|---|---|
| Me | H | H | CF3 | 3-Cl-2-pyridyl | Cl | H |
| Me | H | H | CF3 | 3-Cl-2-pyridyl | Me | Br |
| Me | H | H | CF3 | Me | Me | Cl |
| Me | H | H | CF3 | Et | Me | Br |
| Me | H | H | CF3 | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF3 | 2-ClPh | Me | H |
| H | Me | H | CF3 | 2-ClPh | Me | Cl |
| H | Me | H | CF3 | 3-Cl-2-pyridyl | Me | H |
| H | Me | H | CF3 | 3-Cl-2-pyridyl | Me | Cl |
| H | Me | H | CF3 | 2-ClPh | Cl | H |
| H | Me | H | CF3 | 3-Cl-2-pyridyl | Cl | H |
| H | Me | H | CF3 | 3-Cl-2-pyridyl | Me | Br |
| H | Me | H | CF3 | Me | Me | Cl |
| H | Me | H | CF3 | Et | Me | Br |
| H | Me | H | CF3 | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF3 | 2-ClPh | Me | H |
| Me | Me | H | CF3 | 2-ClPh | Me | Cl |
| Me | Me | H | CF3 | 2-ClPh | Me | H |
| Me | Me | H | CF3 | 3-Cl-2-pyridyl | Me | H |
| Me | Me | H | CF3 | 2-ClPh | Cl | H |
| Me | Me | H | CF3 | 2-ClPh | Cl | H |
| Me | Me | H | CF3 | 3-Cl-2-pyridyl | Me | Br |
| Me | Me | H | CF3 | Me | Me | Cl |
| Me | Me | H | CF3 | Et | Me | Br |
| Me | Me | H | CF3 | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 18

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 2-ClPh | Me | H |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 3-Cl-2-pyridyl | Me | H |
| Me | H | H | CF$_3$ | 3-Cl-2-pyridyl | Me | H |
| Me | H | H | CF$_3$ | 2-ClPh | Cl | H |
| Me | H | H | CF$_3$ | 3-Cl-2-pyridyl | Cl | H |
| Me | H | H | CF$_3$ | 3-Cl-2-pyridyl | Me | Br |
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | H |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF$_3$ | 2-ClPh | Me | H |
| H | H | Me | CF$_3$ | 2-ClPh | Me | Cl |
| H | H | Me | CF$_3$ | 3-Cl-2-pyridyl | Me | H |
| H | H | Me | CF$_3$ | 3-Cl-2-pyridyl | Me | Cl |
| Me | H | Me | CF$_3$ | 3-Cl-2-pyridyl | Me | H |
| Me | H | Me | CF$_3$ | 3-Cl-2-pyridyl | Me | Cl |
| H | Me | Me | CF$_3$ | 3-Cl-2-pyridyl | Me | H |
| H | Me | Me | CF$_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 19

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CF$_3$ | 2-ClPh | Me | H |
| H | H | H | CF$_3$ | 2-ClPh | Me | Cl |
| H | H | H | CF$_3$ | 2-ClPh | Me | H |
| H | H | H | CF$_3$ | 2-ClPh | Cl | H |
| H | H | H | CF$_3$ | 3-Cl-2-pyridyl | Cl | H |
| H | H | H | CF$_3$ | 3-Cl-2-pyridyl | Me | Br |
| H | H | H | CF$_3$ | Me | Me | Cl |
| H | H | H | CF$_3$ | Et | Me | Br |
| H | H | H | CF$_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF$_3$ | 2-ClPh | Me | H |
| Me | H | H | CF$_3$ | 2-ClPh | Me | Cl |
| Me | H | H | CF$_3$ | 3-Cl-2-pyridyl | Me | H |
| Me | H | H | CF$_3$ | 3-Cl-2-pyridyl | Me | H |
| Me | H | H | CF$_3$ | 2-ClPh | Cl | H |
| Me | H | H | CF$_3$ | 3-Cl-2-pyridyl | Cl | H |

TABLE 19-continued

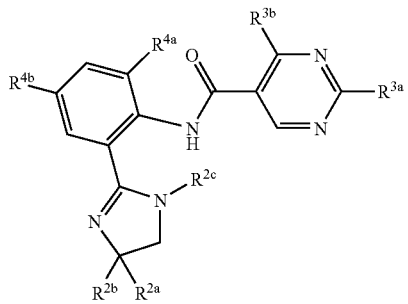

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | H | H | CF$_3$ | 3-Cl-2-pyridyl | Me | Br |
| Me | H | H | CF$_3$ | Me | Me | Cl |
| Me | H | H | CF$_3$ | Et | Me | Br |
| Me | H | H | CF$_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF$_3$ | 2-ClPh | Me | H |
| H | Me | H | CF$_3$ | 2-ClPh | Me | Cl |
| H | Me | H | CF$_3$ | 3-Cl-2-pyridyl | Me | H |
| H | Me | H | CF$_3$ | 3-Cl-2-pyridyl | Me | H |
| H | Me | H | CF$_3$ | 2-ClPh | Cl | H |
| H | Me | H | CF$_3$ | 3-Cl-2-pyridyl | Cl | H |
| H | Me | H | CF$_3$ | 3-Cl-2-pyridyl | Me | Br |
| H | Me | H | CF$_3$ | Me | Me | Cl |
| H | Me | H | CF$_3$ | Et | Me | Br |
| H | Me | H | CF$_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF$_3$ | 2-ClPh | Me | H |
| Me | Me | H | CF$_3$ | 2-ClPh | Me | Cl |
| Me | Me | H | CF$_3$ | 2-ClPh | Me | H |
| Me | Me | H | CF$_3$ | 3-Cl-2-pyridyl | Me | H |
| Me | Me | H | CF$_3$ | 2-ClPh | Cl | H |
| Me | Me | H | CF$_3$ | 2-ClPh | Cl | H |
| Me | Me | H | CF$_3$ | 3-Cl-2-pyridyl | Me | Br |
| Me | Me | H | CF$_3$ | Me | Me | Cl |
| Me | Me | H | CF$_3$ | Et | Me | Br |
| Me | Me | H | CF$_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF$_3$ | 2-ClPh | Me | H |
| H | H | Me | CF$_3$ | 2-ClPh | Me | Cl |
| H | H | Me | CF$_3$ | 3-Cl-2-pyridyl | Me | H |
| H | H | Me | CF$_3$ | 3-Cl-2-pyridyl | Me | Cl |
| Me | H | Me | CF$_3$ | 3-Cl-2-pyridyl | Me | H |
| Me | H | Me | CF$_3$ | 3-Cl-2-pyridyl | Me | Cl |
| H | Me | Me | CF$_3$ | 3-Cl-2-pyridyl | Me | H |
| H | Me | Me | CF$_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 20

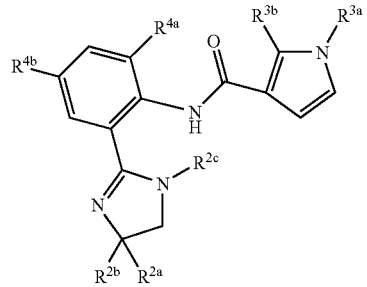

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | H |
| H | H | H | CH$_2$CF$_3$ | 2-ClPh | Cl | H |
| H | H | H | CHF$_2$ | 3-Cl-2-pyridyl | Cl | H |
| H | H | H | CH$_2$CF$_3$ | 3-Cl-2-pyridyl | Me | Br |
| H | H | H | CH$_2$CF$_3$ | Me | Me | Cl |
| H | H | H | CH$_2$CF$_3$ | Et | Me | Br |
| H | H | H | CHF$_2$ | Ph | Me | Cl |
| H | H | H | CH$_2$CF$_3$ | 2-ClPh | Cl | H |
| H | H | H | CH$_2$CF$_3$ | 2-ClPh | Me | Cl |
| H | H | H | CH$_2$CF$_3$ | 2-ClPh | Me | H |
| H | H | H | CH$_2$CF$_3$ | 2-ClPh | Me | Cl |
| H | H | H | CH$_2$CF$_3$ | 3-Cl-2-pyridyl | Me | Br |
| H | H | H | CHF$_2$ | 2-ClPh | Cl | H |
| H | H | H | CH$_2$CF$_3$ | 3-Cl-2-pyridyl | Cl | H |
| Me | H | H | CH$_2$CF$_3$ | 2-ClPh | Me | H |
| Me | H | H | CH$_2$CF$_3$ | 2-ClPh | Me | Cl |
| Me | H | H | CH$_2$CF$_3$ | 3-Cl-2-pyridyl | Me | H |
| Me | H | H | CHF$_2$ | 3-Cl-2-pyridyl | Me | H |
| Me | H | H | CH$_2$CF$_3$ | 2-ClPh | Cl | H |
| Me | H | H | CH$_2$CF$_3$ | 3-Cl-2-pyridyl | Cl | H |
| Me | H | H | CHF$_2$ | 3-Cl-2-pyridyl | Me | Br |
| Me | H | H | CH$_2$CF$_3$ | Me | Me | Cl |
| Me | H | H | CH$_2$CF$_3$ | Et | Me | Br |
| Me | H | H | CH$_2$CF$_3$ | Ph | Me | Cl |
| Me | H | H | CH$_2$CF$_3$ | 2-ClPh | Cl | H |
| Me | H | H | CHF$_2$ | 2-ClPh | Me | Cl |
| Me | H | H | CH$_2$CF$_3$ | 3-Cl-2-pyridyl | Me | H |
| Me | H | H | CH$_2$CF$_3$ | 3-Cl-2-pyridyl | Me | Cl |
| Me | H | H | CH$_2$CF$_3$ | 3-Cl-2-pyridyl | Me | Br |
| Me | H | H | CH$_2$CF$_3$ | 2-ClPh | Cl | H |
| Me | H | H | CHF$_2$ | 3-Cl-2-pyridyl | Cl | H |
| H | Me | H | CH$_2$CF$_3$ | 2-ClPh | Me | H |
| H | Me | H | CH$_2$CF$_3$ | 2-ClPh | Me | Cl |
| H | Me | H | CH$_2$CF$_3$ | 3-Cl-2-pyridyl | Me | H |
| H | Me | H | CHF$_2$ | 3-Cl-2-pyridyl | Me | H |
| H | Me | H | CH$_2$CF$_3$ | 2-ClPh | Cl | H |
| H | Me | H | CH$_2$CF$_3$ | 3-Cl-2-pyridyl | Cl | H |
| H | Me | H | CHF$_2$ | 3-Cl-2-pyridyl | Me | Br |
| H | Me | H | CH$_2$CF$_3$ | Me | Me | Cl |
| H | Me | H | CH$_2$CF$_3$ | Et | Me | Br |
| H | Me | H | CH$_2$CF$_3$ | Ph | Me | Cl |
| H | Me | H | CHF$_2$ | 2-ClPh | Cl | H |
| H | Me | H | CH$_2$CF$_3$ | 2-ClPh | Me | Cl |
| H | Me | H | CH$_2$CF$_3$ | 2-ClPh | Me | H |
| H | Me | H | CH$_2$CF$_3$ | 2-ClPh | Me | Cl |
| H | Me | H | CH$_2$CF$_3$ | 3-Cl-2-pyridyl | Me | Br |
| H | Me | H | CH$_2$CF$_3$ | 2-ClPh | Cl | H |
| H | Me | H | CH$_2$CF$_3$ | 2-ClPh | Cl | H |
| Me | Me | H | CHF$_2$ | 2-ClPh | Me | H |
| Me | Me | H | CH$_2$CF$_3$ | 2-ClPh | Me | Cl |
| Me | Me | H | CH$_2$CF$_3$ | 2-ClPh | Me | H |
| Me | Me | H | CH$_2$CF$_3$ | 3-Cl-2-pyridyl | Me | H |
| Me | Me | H | CH$_2$CF$_3$ | 2-ClPh | Cl | H |
| Me | Me | H | CHF$_2$ | 2-ClPh | Cl | H |
| Me | Me | H | CH$_2$CF$_3$ | 3-Cl-2-pyridyl | Me | Br |
| Me | Me | H | CH$_2$CF$_3$ | Me | Me | Cl |
| Me | Me | H | CH$_2$CF$_3$ | Et | Me | Br |
| Me | Me | H | CH$_2$CF$_3$ | Ph | Me | Cl |
| Me | Me | H | CH$_2$CF$_3$ | 2-ClPh | Cl | H |

TABLE 20-continued

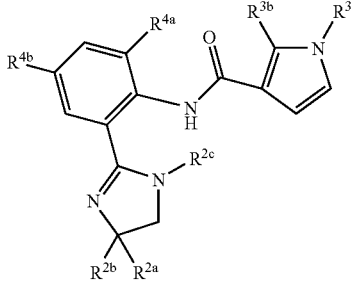

| R²ᵃ | R²ᵇ | R²ᶜ | R³ᵃ | R³ᵇ | R⁴ᵃ | R⁴ᵇ |
|---|---|---|---|---|---|---|
| Me | Me | H | CHF₂ | 2-ClPh | Me | Cl |
| Me | Me | H | CH₂CF₃ | 3-Cl-2-pyridyl | Me | H |
| Me | Me | H | CH₂CF₃ | 3-Cl-2-pyridyl | Me | Cl |
| Me | Me | H | CH₂CF₃ | 3-Cl-2-pyridyl | Me | Br |
| Me | Me | H | CHF₂ | 2-ClPh | Cl | H |
| Me | Me | H | CH₂CF₃ | 3-Cl-2-pyridyl | Cl | H |
| H | H | Me | CH₂CF₃ | 2-ClPh | Me | H |
| H | H | Me | CH₂CF₃ | 2-ClPh | Me | Cl |
| H | H | Me | CH₂CF₃ | 3-Cl-2-pyridyl | Me | H |
| H | H | Me | CH₂CF₃ | 3-Cl-2-pyridyl | Me | Cl |
| Me | H | Me | CH₂CF₃ | 3-Cl-2-pyridyl | Me | H |
| Me | H | Me | CH₂CF₃ | 3-Cl-2-pyridyl | Me | Cl |
| H | Me | Me | CH₂CF₃ | 3-Cl-2-pyridyl | Me | H |
| H | Me | Me | CH₂CF₃ | 3-Cl-2-pyridyl | Me | Cl |
| H | Me | Me | CH₂CF₃ | 3-Cl-2-pyridyl | Me | H |
| H | Me | Me | CH₂CF₃ | 3-Cl-2-pyridyl | Me | Cl |

TABLE 21

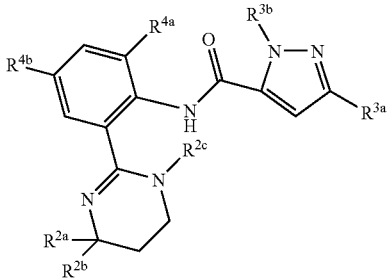

| R²ᵃ | R²ᵇ | R²ᶜ | R³ᵃ | R³ᵇ | R⁴ᵃ | R⁴ᵇ |
|---|---|---|---|---|---|---|
| H | H | H | CF₃ | 2-ClPh | Me | H |
| H | H | H | CF₃ | 2-ClPh | Me | Cl |
| H | H | H | CF₃ | 3-Cl-2-pyridyl | Me | H |
| H | H | H | CF₃ | 3-Cl-2-pyridyl | Me | Cl |
| H | H | H | CF₃ | 2-ClPh | Cl | H |
| H | H | H | CF₃ | 3-Cl-2-pyridyl | Cl | H |
| H | H | H | CF₃ | 3-Cl-2-pyridyl | Me | Br |
| H | H | H | CF₃ | Me | Me | Cl |
| H | H | H | CF₃ | Et | Me | Br |
| H | H | H | CF₃ | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF₃ | 2-ClPh | Me | H |
| Me | H | H | CF₃ | 2-ClPh | Me | Cl |
| Me | H | H | CF₃ | 3-Cl-2-pyridyl | Me | H |
| Me | H | H | CF₃ | 3-Cl-2-pyridyl | Me | Cl |
| Me | H | H | CF₃ | 2-ClPh | Cl | H |
| Me | H | H | CF₃ | 3-Cl-2-pyridyl | Cl | H |
| Me | H | H | CF₃ | 3-Cl-2-pyridyl | Me | Br |
| Me | H | H | CF₃ | Me | Me | Cl |

TABLE 21-continued

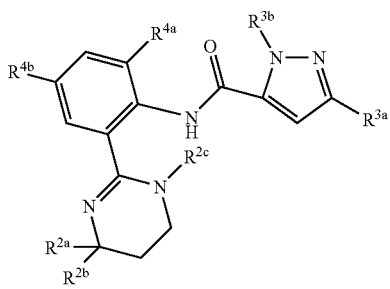

| R²ᵃ | R²ᵇ | R²ᶜ | R³ᵃ | R³ᵇ | R⁴ᵃ | R⁴ᵇ |
|---|---|---|---|---|---|---|
| Me | H | H | CF₃ | Et | Me | Br |
| Me | H | H | CF₃ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF₃ | 2-ClPh | Me | H |
| H | Me | H | CF₃ | 2-ClPh | Me | Cl |
| H | Me | H | CF₃ | 3-Cl-2-pyridyl | Me | H |
| H | Me | H | CF₃ | 3-Cl-2-pyridyl | Me | Cl |
| H | Me | H | CF₃ | 2-ClPh | Cl | H |
| H | Me | H | CF₃ | 3-Cl-2-pyridyl | Cl | H |
| H | Me | H | CF₃ | 3-Cl-2-pyridyl | Me | Br |
| H | Me | H | CF₃ | Me | Me | Cl |
| H | Me | H | CF₃ | Et | Me | Br |
| H | Me | H | CF₃ | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | CF₃ | 2-ClPh | Me | H |
| Me | Me | H | CF₃ | 2-ClPh | Me | Cl |
| Me | Me | H | CF₃ | 3-Cl-2-pyridyl | Me | H |
| Me | Me | H | CF₃ | 3-Cl-2-pyridyl | Me | Cl |
| Me | Me | H | CF₃ | 2-ClPh | Cl | H |
| Me | Me | H | CF₃ | 3-Cl-2-pyridyl | Cl | H |
| Me | Me | H | CF₃ | 3-Cl-2-pyridyl | Me | Br |
| Me | Me | H | CF₃ | Me | Me | Cl |
| Me | Me | H | CF₃ | Et | Me | Br |
| Me | Me | H | CF₃ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF₃ | 2-ClPh | Me | H |
| H | H | Me | CF₃ | 2-ClPh | Me | Cl |
| H | H | Me | CF₃ | 3-Cl-2-pyridyl | Me | H |
| H | H | Me | CF₃ | 3-Cl-2-pyridyl | Me | Cl |
| Me | H | Me | CF₃ | 3-Cl-2-pyridyl | Me | H |
| Me | H | Me | CF₃ | 3-Cl-2-pyridyl | Me | Cl |
| H | Me | Me | CF₃ | 3-Cl-2-pyridyl | Me | H |
| H | Me | Me | CF₃ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 22

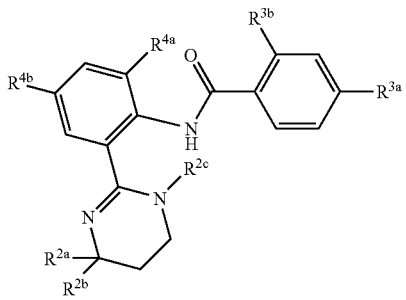

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | $CF_3$ | 2-ClPh | Me | H |
| H | H | H | $CF_3$ | 2-ClPh | Me | Cl |
| H | H | H | $CF_3$ | 2-ClPh | Me | H |
| H | H | H | $CF_3$ | 2-ClPh | Cl | H |
| H | H | H | $CF_3$ | 3-Cl-2-pyridyl | Cl | H |
| H | H | H | $CF_3$ | 3-Cl-2-pyridyl | Me | Br |
| H | H | H | $CF_3$ | Me | Me | Cl |
| H | H | H | $CF_3$ | Et | Me | Br |
| H | H | H | $CF_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | $CF_3$ | 2-ClPh | Me | H |
| Me | H | H | $CF_3$ | 2-ClPh | Me | Cl |
| Me | H | H | $CF_3$ | 3-Cl-2-pyridyl | Me | H |
| Me | H | H | $CF_3$ | 3-Cl-2-pyridyl | Me | Cl |
| Me | H | H | $CF_3$ | 2-ClPh | Cl | H |
| Me | H | H | $CF_3$ | 3-Cl-2-pyridyl | Cl | H |
| Me | H | H | $CF_3$ | 3-Cl-2-pyridyl | Me | Br |
| Me | H | H | $CF_3$ | Me | Me | Cl |
| Me | H | H | $CF_3$ | Et | Me | Br |
| Me | H | H | $CF_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | $CF_3$ | 2-ClPh | Me | H |
| H | Me | H | $CF_3$ | 2-ClPh | Me | Cl |
| H | Me | H | $CF_3$ | 3-Cl-2-pyridyl | Me | H |
| H | Me | H | $CF_3$ | 3-Cl-2-pyridyl | Me | H |
| H | Me | H | $CF_3$ | 2-ClPh | Cl | H |
| H | Me | H | $CF_3$ | 3-Cl-2-pyridyl | Cl | H |
| H | Me | H | $CF_3$ | 3-Cl-2-pyridyl | Me | Br |
| H | Me | H | $CF_3$ | Me | Me | Cl |
| H | Me | H | $CF_3$ | Et | Me | Br |
| H | Me | H | $CF_3$ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | $CF_3$ | 2-ClPh | Me | H |
| Me | Me | H | $CF_3$ | 2-ClPh | Me | Cl |
| Me | Me | H | $CF_3$ | 2-ClPh | Me | H |
| Me | Me | H | $CF_3$ | 3-Cl-2-pyridyl | Me | H |
| Me | Me | H | $CF_3$ | 2-ClPh | Cl | H |
| Me | Me | H | $CF_3$ | 2-ClPh | Cl | H |
| Me | Me | H | $CF_3$ | 3-Cl-2-pyridyl | Me | Br |
| Me | Me | H | $CF_3$ | Me | Me | Cl |
| Me | Me | H | $CF_3$ | Et | Me | Br |
| Me | Me | H | $CF_3$ | Ph | Me | Cl |
| Me | Me | H | Br | 2-ClPh | Cl | H |

TABLE 22-continued

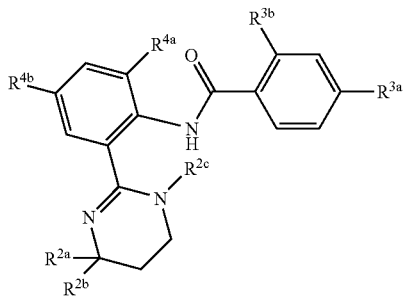

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | $CF_3$ | 2-ClPh | Me | H |
| H | H | Me | $CF_3$ | 2-ClPh | Me | Cl |
| H | H | Me | $CF_3$ | 3-Cl-2-pyridyl | Me | H |
| H | H | Me | $CF_3$ | 3-Cl-2-pyridyl | Me | Cl |
| Me | H | Me | $CF_3$ | 3-Cl-2-pyridyl | Me | H |
| Me | H | Me | $CF_3$ | 3-Cl-2-pyridyl | Me | Cl |
| H | Me | Me | $CF_3$ | 3-Cl-2-pyridyl | Me | H |
| H | Me | Me | $CF_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 23

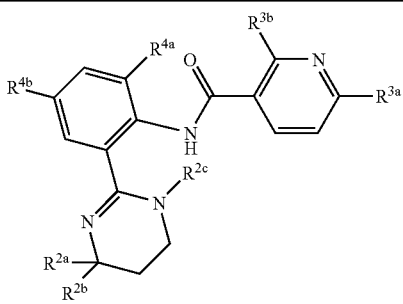

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | $CF_3$ | 2-ClPh | Me | H |
| H | H | H | $CF_3$ | 2-ClPh | Me | Cl |
| H | H | H | $CF_3$ | 2-ClPh | Me | H |
| H | H | H | $CF_3$ | 2-ClPh | Me | H |
| H | H | H | $CF_3$ | 2-ClPh | Cl | H |
| H | H | H | $CF_3$ | 3-Cl-2-pyridyl | Cl | H |
| H | H | H | $CF_3$ | 3-Cl-2-pyridyl | Me | Br |
| H | H | H | $CF_3$ | Me | Me | Cl |
| H | H | H | $CF_3$ | Et | Me | Br |
| H | H | H | $CF_3$ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | $CF_3$ | 2-ClPh | Me | H |
| Me | H | H | $CF_3$ | 2-ClPh | Me | Cl |
| Me | H | H | $CF_3$ | 3-Cl-2-pyridyl | Me | H |
| Me | H | H | $CF_3$ | 3-Cl-2-pyridyl | Me | Cl |
| Me | H | H | $CF_3$ | 2-ClPh | Cl | H |
| Me | H | H | $CF_3$ | 3-Cl-2-pyridyl | Cl | H |
| Me | H | H | $CF_3$ | 3-Cl-2-pyridyl | Me | Br |

TABLE 23-continued

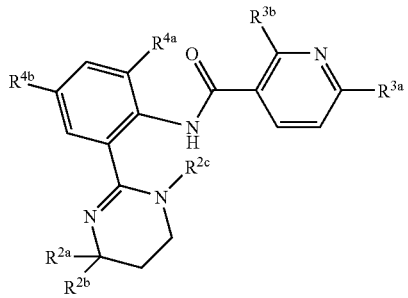

| R²ᵃ | R²ᵇ | R²ᶜ | R³ᵃ | R³ᵇ | R⁴ᵃ | R⁴ᵇ |
|---|---|---|---|---|---|---|
| Me | H | H | CF₃ | Me | Me | Cl |
| Me | H | H | CF₃ | Et | Me | Br |
| Me | H | H | CF₃ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF₃ | 2-ClPh | Me | H |
| H | Me | H | CF₃ | 2-ClPh | Me | Cl |
| H | Me | H | CF₃ | 3-Cl-2-pyridyl | Me | H |
| H | Me | H | CF₃ | 3-Cl-2-pyridyl | Me | Cl |
| H | Me | H | CF₃ | 2-ClPh | Cl | H |
| H | Me | H | CF₃ | 3-Cl-2-pyridyl | Cl | H |
| H | Me | H | CF₃ | 3-Cl-2-pyridyl | Me | Br |
| H | Me | H | CF₃ | Me | Me | Cl |
| H | Me | H | CF₃ | Et | Me | Br |
| H | Me | H | CF₃ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF₃ | 2-ClPh | Me | H |
| Me | Me | H | CF₃ | 2-ClPh | Me | Cl |
| Me | Me | H | CF₃ | 2-ClPh | Me | H |
| Me | Me | H | CF₃ | 3-Cl-2-pyridyl | Me | H |
| Me | Me | H | CF₃ | 2-ClPh | Cl | H |
| Me | Me | H | CF₃ | 2-ClPh | Cl | H |
| Me | Me | H | CF₃ | 3-Cl-2-pyridyl | Me | Br |
| Me | Me | H | CF₃ | Me | Me | Cl |
| Me | Me | H | CF₃ | Et | Me | Br |
| Me | Me | H | CF₃ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF₃ | 2-ClPh | Me | H |
| H | H | Me | CF₃ | 2-ClPh | Me | Cl |
| H | H | Me | CF₃ | 3-Cl-2-pyridyl | Me | H |
| H | H | Me | CF₃ | 3-Cl-2-pyridyl | Me | Cl |
| Me | H | Me | CF₃ | 3-Cl-2-pyridyl | Me | H |
| Me | H | Me | CF₃ | 3-Cl-2-pyridyl | Me | Cl |
| H | Me | Me | CF₃ | 3-Cl-2-pyridyl | Me | H |
| H | Me | Me | CF₃ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 24

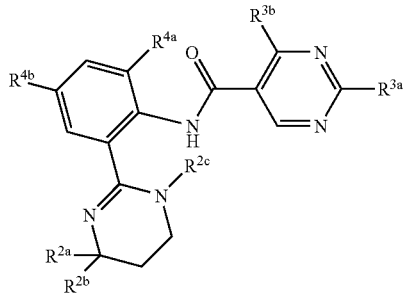

| R²ᵃ | R²ᵇ | R²ᶜ | R³ᵃ | R³ᵇ | R⁴ᵃ | R⁴ᵇ |
|---|---|---|---|---|---|---|
| H | H | H | CF₃ | 2-ClPh | Me | H |
| H | H | H | CF₃ | 2-ClPh | Me | Cl |
| H | H | H | CF₃ | 2-ClPh | Me | H |
| H | H | H | CF₃ | 2-ClPh | Cl | H |
| H | H | H | CF₃ | 3-Cl-2-pyridyl | Cl | H |
| H | H | H | CF₃ | 3-Cl-2-pyridyl | Me | Br |
| H | H | H | CF₃ | Me | Me | Cl |
| H | H | H | CF₃ | Et | Me | Br |
| H | H | H | CF₃ | Ph | Me | Cl |
| H | H | H | Br | 2-ClPh | Cl | H |
| H | H | H | Cl | 2-ClPh | Me | Cl |
| H | H | H | Br | 2-ClPh | Me | H |
| H | H | H | Br | 2-ClPh | Me | Cl |
| H | H | H | Cl | 3-Cl-2-pyridyl | Me | Br |
| H | H | H | Br | 3-Cl-2-pyridyl | Cl | H |
| Me | H | H | CF₃ | 2-ClPh | Me | H |
| Me | H | H | CF₃ | 2-ClPh | Me | Cl |
| Me | H | H | CF₃ | 3-Cl-2-pyridyl | Me | H |
| Me | H | H | CF₃ | 3-Cl-2-pyridyl | Me | H |
| Me | H | H | CF₃ | 2-ClPh | Cl | H |
| Me | H | H | CF₃ | 3-Cl-2-pyridyl | Cl | H |
| Me | H | H | CF₃ | 3-Cl-2-pyridyl | Me | Br |
| Me | H | H | CF₃ | Me | Me | Cl |
| Me | H | H | CF₃ | Et | Me | Br |
| Me | H | H | CF₃ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF₃ | 2-ClPh | Me | H |
| H | Me | H | CF₃ | 2-ClPh | Me | Cl |
| H | Me | H | CF₃ | 3-Cl-2-pyridyl | Me | H |
| H | Me | H | CF₃ | 3-Cl-2-pyridyl | Me | H |
| H | Me | H | CF₃ | 2-ClPh | Cl | H |
| H | Me | H | CF₃ | 3-Cl-2-pyridyl | Cl | H |
| H | Me | H | CF₃ | 3-Cl-2-pyridyl | Me | Br |
| H | Me | H | CF₃ | Me | Me | Cl |
| H | Me | H | CF₃ | Et | Me | Br |
| H | Me | H | CF₃ | Ph | Me | Cl |
| H | Me | H | Br | 2-ClPh | Cl | H |
| H | Me | H | Cl | 2-ClPh | Me | Cl |
| H | Me | H | Br | 2-ClPh | Me | H |
| H | Me | H | Br | 2-ClPh | Me | Cl |
| H | Me | H | Cl | 3-Cl-2-pyridyl | Me | Br |
| H | Me | H | Br | 2-ClPh | Cl | H |
| H | Me | H | Br | 2-ClPh | Cl | H |
| Me | Me | H | CF₃ | 2-ClPh | Me | H |
| Me | Me | H | CF₃ | 2-ClPh | Me | Cl |
| Me | Me | H | CF₃ | 2-ClPh | Me | H |
| Me | Me | H | CF₃ | 3-Cl-2-pyridyl | Me | H |
| Me | Me | H | CF₃ | 2-ClPh | Cl | H |
| Me | Me | H | CF₃ | 2-ClPh | Cl | H |
| Me | Me | H | CF₃ | 3-Cl-2-pyridyl | Me | Br |
| Me | Me | H | CF₃ | Me | Me | Cl |
| Me | Me | H | CF₃ | Et | Me | Br |
| Me | Me | H | CF₃ | Ph | Me | Cl |
| Me | Me | H | Br | 2-ClPh | Cl | H |

TABLE 24-continued

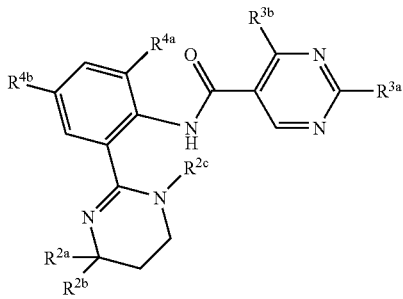

| R2a | R2b | R2c | R3a | R3b | R4a | R4b |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 25

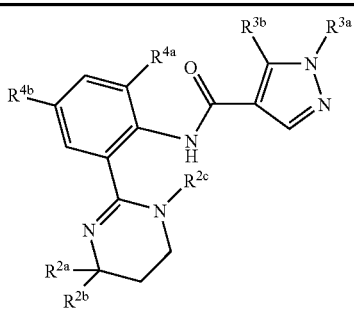

| R2a | R2b | R2c | R3a | R3b | R4a | R4b |
|---|---|---|---|---|---|---|
| H | H | H | CH2CF3 | 2-ClPh | Me | H |
| H | H | H | CH2CF3 | 2-ClPh | Me | Cl |
| H | H | H | CH2CF3 | 2-ClPh | Me | H |
| H | H | H | CH2CF3 | 2-ClPh | Me | H |
| H | H | H | CH2CF3 | 2-ClPh | Cl | H |
| H | H | H | CHF2 | 3-Cl-2-pyridyl | Cl | H |
| H | H | H | CH2CF3 | 3-Cl-2-pyridyl | Me | Br |
| H | H | H | CH2CF3 | Me | Me | Cl |
| H | H | H | CH2CF3 | Et | Me | Br |
| H | H | H | CHF2 | Ph | Me | Cl |
| H | H | H | CH2CF3 | 2-ClPh | Cl | H |
| H | H | H | CH2CF3 | 2-ClPh | Me | Cl |
| H | H | H | CH2CF3 | 2-ClPh | Me | H |
| H | H | H | CH2CF3 | 2-ClPh | Me | Cl |
| H | H | H | CH2CF3 | 3-Cl-2-pyridyl | Me | Br |
| H | H | H | CHF2 | 2-ClPh | Cl | H |
| H | H | H | CH2CF3 | 3-Cl-2-pyridyl | Cl | H |
| Me | H | H | CH2CF3 | 2-ClPh | Me | H |
| Me | H | H | CH2CF3 | 2-ClPh | Me | Cl |
| Me | H | H | CH2CF3 | 3-Cl-2-pyridyl | Me | H |
| Me | H | H | CHF2 | 3-Cl-2-pyridyl | Me | H |
| Me | H | H | CH2CF3 | 2-ClPh | Cl | H |
| Me | H | H | CH2CF3 | 3-Cl-2-pyridyl | Cl | H |

TABLE 25-continued

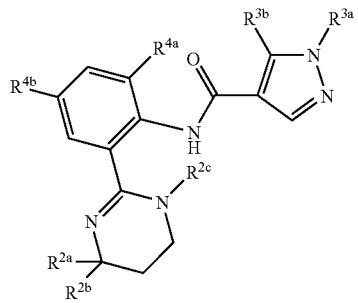

| R2a | R2b | R2c | R3a | R3b | R4a | R4b |
|---|---|---|---|---|---|---|
| Me | H | H | CHF2 | 3-Cl-2-pyridyl | Me | Br |
| Me | H | H | CH2CF3 | Me | Me | Cl |
| Me | H | H | CH2CF3 | Et | Me | Br |
| Me | H | H | CH2CF3 | Ph | Me | Cl |
| Me | H | H | CH2CF3 | 2-ClPh | Cl | H |
| Me | H | H | CHF2 | 2-ClPh | Me | Cl |
| Me | H | H | CH2CF3 | 3-Cl-2-pyridyl | Me | H |
| Me | H | H | CH2CF3 | 3-Cl-2-pyridyl | Me | Cl |
| Me | H | H | CH2CF3 | 3-Cl-2-pyridyl | Me | Br |
| Me | H | H | CH2CF3 | 2-ClPh | Cl | H |
| Me | H | H | CHF2 | 3-Cl-2-pyridyl | Cl | H |
| H | Me | H | CH2CF3 | 2-ClPh | Me | H |
| H | Me | H | CH2CF3 | 2-ClPh | Me | Cl |
| H | Me | H | CH2CF3 | 3-Cl-2-pyridyl | Me | H |
| H | Me | H | CHF2 | 3-Cl-2-pyridyl | Me | H |
| H | Me | H | CH2CF3 | 2-ClPh | Cl | H |
| H | Me | H | CH2CF3 | 3-Cl-2-pyridyl | Cl | H |
| H | Me | H | CHF2 | 3-Cl-2-pyridyl | Me | Br |
| H | Me | H | CH2CF3 | Me | Me | Cl |
| H | Me | H | CH2CF3 | Et | Me | Br |
| H | Me | H | CH2CF3 | Ph | Me | Cl |
| H | Me | H | CHF2 | 2-ClPh | Cl | H |
| H | Me | H | CH2CF3 | 2-ClPh | Me | Cl |
| H | Me | H | CH2CF3 | 2-ClPh | Me | H |
| H | Me | H | CHF2 | 2-ClPh | Me | Cl |
| H | Me | H | CH2CF3 | 3-Cl-2-pyridyl | Me | Br |
| H | Me | H | CH2CF3 | 2-ClPh | Cl | H |
| H | Me | H | CH2CF3 | 2-ClPh | Cl | H |
| Me | Me | H | CHF2 | 2-ClPh | Me | H |
| Me | Me | H | CH2CF3 | 2-ClPh | Me | Cl |
| Me | Me | H | CH2CF3 | 2-ClPh | Me | H |
| Me | Me | H | CH2CF3 | 3-Cl-2-pyridyl | Me | H |
| Me | Me | H | CH2CF3 | 2-ClPh | Cl | H |
| Me | Me | H | CHF2 | 2-ClPh | Cl | H |
| Me | Me | H | CH2CF3 | 3-Cl-2-pyridyl | Me | Br |
| Me | Me | H | CH2CF3 | Me | Me | Cl |
| Me | Me | H | CH2CF3 | Et | Me | Br |
| Me | Me | H | CH2CF3 | Ph | Me | Cl |
| Me | Me | H | CH2CF3 | 2-ClPh | Cl | H |
| Me | Me | H | CHF2 | 2-ClPh | Me | Cl |
| Me | Me | H | CH2CF3 | 3-Cl-2-pyridyl | Me | H |
| Me | Me | H | CH2CF3 | 3-Cl-2-pyridyl | Me | Cl |
| Me | Me | H | CH2CF3 | 3-Cl-2-pyridyl | Me | Br |
| Me | Me | H | CH2CF3 | 2-ClPh | Cl | H |
| Me | Me | H | CHF2 | 2-ClPh | Cl | H |
| Me | Me | H | CH2CF3 | 3-Cl-2-pyridyl | Cl | H |
| H | H | Me | CH2CF3 | 2-ClPh | Me | H |
| H | H | Me | CH2CF3 | 2-ClPh | Me | Cl |
| H | H | Me | CH2CF3 | 3-Cl-2-pyridyl | Me | H |
| H | H | Me | CH2CF3 | 3-Cl-2-pyridyl | Me | Cl |
| Me | H | Me | CH2CF3 | 3-Cl-2-pyridyl | Me | H |
| Me | H | Me | CH2CF3 | 3-Cl-2-pyridyl | Me | Cl |
| H | Me | Me | CH2CF3 | 3-Cl-2-pyridyl | Me | H |
| H | Me | Me | CH2CF3 | 3-Cl-2-pyridyl | Me | Cl |

TABLE 26

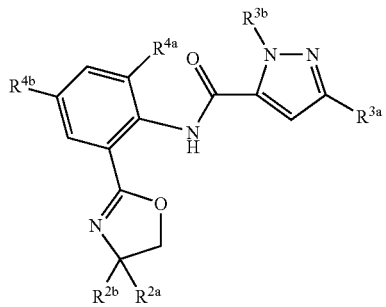

| R²ᵃ | R²ᵇ | R³ᵃ | R³ᵇ | R⁴ᵃ | R⁴ᵇ |
|---|---|---|---|---|---|
| H | H | CF₃ | 2-ClPh | Me | H |
| H | H | CF₃ | 2-ClPh | Me | Cl |
| H | H | CF₃ | 2-ClPh | Cl | H |
| H | H | CF₃ | Me | Me | Cl |
| H | H | CF₃ | Et | Me | Br |
| H | H | CF₃ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF₃ | 2-ClPh | Me | H |
| Me | H | CF₃ | 2-ClPh | Me | Cl |
| Me | H | CF₃ | 2-ClPh | Cl | H |
| Me | H | CF₃ | Me | Me | Cl |
| Me | H | CF₃ | Et | Me | Br |
| Me | H | CF₃ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF₃ | 2-ClPh | Me | H |
| H | Me | CF₃ | 2-ClPh | Me | Cl |
| H | Me | CF₃ | 2-ClPh | Cl | H |
| H | Me | CF₃ | Me | Me | Cl |
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |
| H | Me | CF₃ | 3-Cl-2-pyridyl | Cl | H |
| H | Me | CF₃ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF₃ | 3-Cl-2-pyridyl | Me | H |
| Me | Me | CF₃ | 3-Cl-2-pyridyl | Me | Cl |
| Me | Me | CF₃ | 3-Cl-2-pyridyl | Cl | H |
| Me | Me | CF₃ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 27

| R²ᵃ | R²ᵇ | R³ᵃ | R³ᵇ | R⁴ᵃ | R⁴ᵇ |
|---|---|---|---|---|---|
| H | H | CF₃ | 2-ClPh | Me | H |
| H | H | CF₃ | 2-ClPh | Me | Cl |
| H | H | CF₃ | 2-ClPh | Cl | H |
| H | H | CF₃ | Me | Me | Cl |
| H | H | CF₃ | Et | Me | Br |
| H | H | CF₃ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF₃ | 2-ClPh | Me | H |
| Me | H | CF₃ | 2-ClPh | Me | Cl |
| Me | H | CF₃ | 2-ClPh | Cl | H |
| Me | H | CF₃ | Me | Me | Cl |
| Me | H | CF₃ | Et | Me | Br |
| Me | H | CF₃ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |

TABLE 27-continued

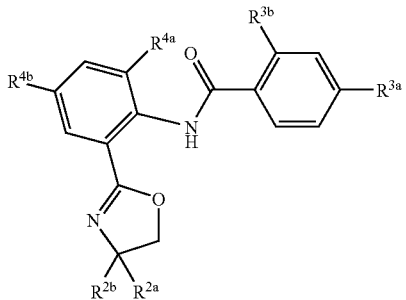

| R2a | R2b | R3a | R3b | R4a | R4b |
|---|---|---|---|---|---|
| H | Me | CF3 | 2-ClPh | Me | H |
| H | Me | CF3 | 2-ClPh | Me | Cl |
| H | Me | CF3 | 2-ClPh | Cl | H |
| H | Me | CF3 | Me | Me | Cl |
| H | Me | CF3 | Et | Me | Br |
| H | Me | CF3 | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF3 | 2-ClPh | Me | H |
| Me | Me | CF3 | 2-ClPh | Me | Cl |
| Me | Me | CF3 | 2-ClPh | Cl | H |
| Me | Me | CF3 | Me | Me | Cl |
| Me | Me | CF3 | Et | Me | Br |
| Me | Me | CF3 | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF3 | 3-Cl-2-pyridyl | Me | H |
| H | H | CF3 | 3-Cl-2-pyridyl | Me | Cl |
| H | H | CF3 | 3-Cl-2-pyridyl | Cl | H |
| H | H | CF3 | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF3 | 3-Cl-2-pyridyl | Me | H |
| Me | H | CF3 | 3-Cl-2-pyridyl | Me | Cl |
| Me | H | CF3 | 3-Cl-2-pyridyl | Cl | H |
| Me | H | CF3 | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF3 | 3-Cl-2-pyridyl | Me | H |
| H | Me | CF3 | 3-Cl-2-pyridyl | Me | Cl |
| H | Me | CF3 | 3-Cl-2-pyridyl | Cl | H |
| H | Me | CF3 | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF3 | 3-Cl-2-pyridyl | Me | H |
| Me | Me | CF3 | 3-Cl-2-pyridyl | Me | Cl |
| Me | Me | CF3 | 3-Cl-2-pyridyl | Cl | H |
| Me | Me | CF3 | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 28

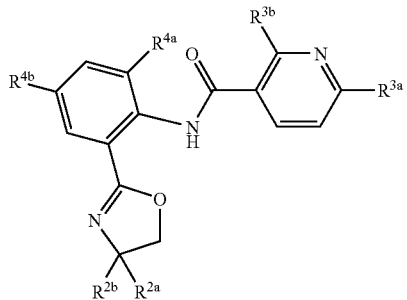

| R2a | R2b | R3a | R3b | R4a | R4b |
|---|---|---|---|---|---|
| H | H | CF3 | 2-ClPh | Me | H |
| H | H | CF3 | 2-ClPh | Me | Cl |
| H | H | CF3 | 2-ClPh | Cl | H |
| H | H | CF3 | Me | Me | Cl |
| H | H | CF3 | Et | Me | Br |
| H | H | CF3 | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF3 | 2-ClPh | Me | H |
| Me | H | CF3 | 2-ClPh | Me | Cl |
| Me | H | CF3 | 2-ClPh | Cl | H |
| Me | H | CF3 | Me | Me | Cl |
| Me | H | CF3 | Et | Me | Br |
| Me | H | CF3 | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF3 | 2-ClPh | Me | H |
| H | Me | CF3 | 2-ClPh | Me | Cl |
| H | Me | CF3 | 2-ClPh | Cl | H |
| H | Me | CF3 | Me | Me | Cl |
| H | Me | CF3 | Et | Me | Br |
| H | Me | CF3 | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF3 | 2-ClPh | Me | H |
| Me | Me | CF3 | 2-ClPh | Me | Cl |
| Me | Me | CF3 | 2-ClPh | Cl | H |
| Me | Me | CF3 | Me | Me | Cl |
| Me | Me | CF3 | Et | Me | Br |
| Me | Me | CF3 | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF3 | 3-Cl-2-pyridyl | Me | H |
| H | H | CF3 | 3-Cl-2-pyridyl | Me | Cl |
| H | H | CF3 | 3-Cl-2-pyridyl | Cl | H |
| H | H | CF3 | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF3 | 3-Cl-2-pyridyl | Me | H |
| Me | H | CF3 | 3-Cl-2-pyridyl | Me | Cl |
| Me | H | CF3 | 3-Cl-2-pyridyl | Cl | H |
| Me | H | CF3 | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF3 | 3-Cl-2-pyridyl | Me | H |

TABLE 28-continued

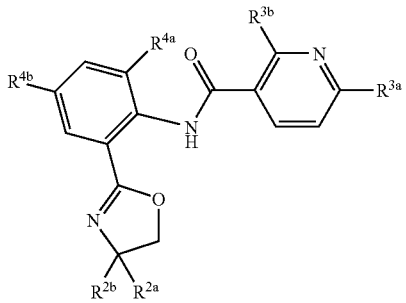

| R$^{2a}$ | R$^{2b}$ | R$^{3a}$ | R$^{3b}$ | R$^{4a}$ | R$^{4b}$ |
|---|---|---|---|---|---|
| H | Me | CF$_3$ | 3-Cl-2-pyridyl | Me | Cl |
| H | Me | CF$_3$ | 3-Cl-2-pyridyl | Cl | H |
| H | Me | CF$_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF$_3$ | 3-Cl-2-pyridyl | Me | H |
| Me | Me | CF$_3$ | 3-Cl-2-pyridyl | Me | Cl |
| Me | Me | CF$_3$ | 3-Cl-2-pyridyl | Cl | H |
| Me | Me | CF$_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 29

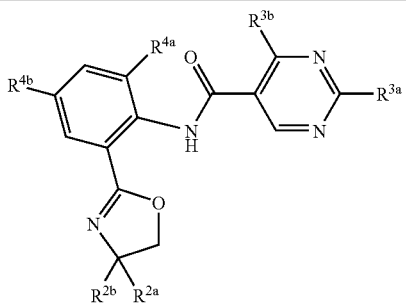

| R$^{2a}$ | R$^{2b}$ | R$^{3a}$ | R$^{3b}$ | R$^{4a}$ | R$^{4b}$ |
|---|---|---|---|---|---|
| H | H | CF$_3$ | 2-ClPh | Me | H |
| H | H | CF$_3$ | 2-ClPh | Me | Cl |
| H | H | CF$_3$ | 2-ClPh | Cl | H |
| H | H | CF$_3$ | Me | Me | Cl |
| H | H | CF$_3$ | Et | Me | Br |
| H | H | CF$_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF$_3$ | 2-ClPh | Me | H |
| Me | H | CF$_3$ | 2-ClPh | Me | Cl |
| Me | H | CF$_3$ | 2-ClPh | Cl | H |
| Me | H | CF$_3$ | Me | Me | Cl |
| Me | H | CF$_3$ | Et | Me | Br |
| Me | H | CF$_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |

TABLE 29-continued

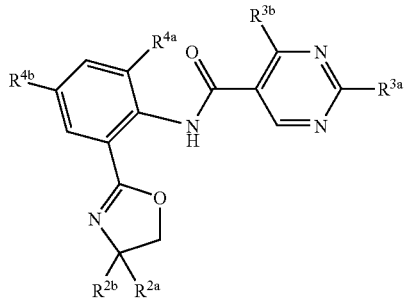

| R$^{2a}$ | R$^{2b}$ | R$^{3a}$ | R$^{3b}$ | R$^{4a}$ | R$^{4b}$ |
|---|---|---|---|---|---|
| H | Me | CF$_3$ | 2-ClPh | Me | H |
| H | Me | CF$_3$ | 2-ClPh | Me | Cl |
| H | Me | CF$_3$ | 2-ClPh | Cl | H |
| H | Me | CF$_3$ | Me | Me | Cl |
| H | Me | CF$_3$ | Et | Me | Br |
| H | Me | CF$_3$ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF$_3$ | 2-ClPh | Me | H |
| Me | Me | CF$_3$ | 2-ClPh | Me | Cl |
| Me | Me | CF$_3$ | 2-ClPh | Cl | H |
| Me | Me | CF$_3$ | Me | Me | Cl |
| Me | Me | CF$_3$ | Et | Me | Br |
| Me | Me | CF$_3$ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF$_3$ | 3-Cl-2-pyridyl | Me | H |
| H | H | CF$_3$ | 3-Cl-2-pyridyl | Me | Cl |
| H | H | CF$_3$ | 3-Cl-2-pyridyl | Cl | H |
| H | H | CF$_3$ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF$_3$ | 3-Cl-2-pyridyl | Me | H |
| Me | H | CF$_3$ | 3-Cl-2-pyridyl | Me | Cl |
| Me | H | CF$_3$ | 3-Cl-2-pyridyl | Cl | H |
| Me | H | CF$_3$ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF$_3$ | 3-Cl-2-pyridyl | Me | H |
| H | Me | CF$_3$ | 3-Cl-2-pyridyl | Me | Cl |
| H | Me | CF$_3$ | 3-Cl-2-pyridyl | Cl | H |
| H | Me | CF$_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF$_3$ | 3-Cl-2-pyridyl | Me | H |
| Me | Me | CF$_3$ | 3-Cl-2-pyridyl | Me | Cl |
| Me | Me | CF$_3$ | 3-Cl-2-pyridyl | Cl | H |
| Me | Me | CF$_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 30

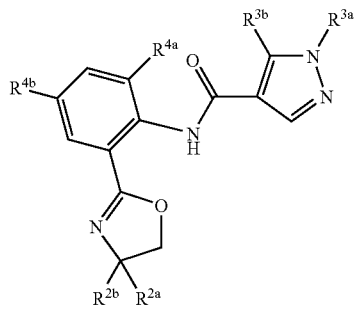

| R$^{2a}$ | R$^{2b}$ | R$^{3a}$ | R$^{3b}$ | R$^{4a}$ | R$^{4b}$ |
|---|---|---|---|---|---|
| H | H | CH$_2$CF$_3$ | 2-ClPh | Me | H |
| H | H | CH$_2$CF$_3$ | 2-ClPh | Me | Cl |
| H | H | CH$_2$CF$_3$ | 2-ClPh | Cl | H |
| H | H | CH$_2$CF$_3$ | 2-ClPh | Me | Br |
| H | H | CH$_2$CF$_3$ | 3-Cl-2-pyridyl | Me | H |
| H | H | CH$_2$CF$_3$ | 3-Cl-2-pyridyl | Cl | H |
| H | H | CH$_2$CF$_3$ | 3-Cl-2-pyridyl | Me | Br |
| H | H | CH$_2$CF$_3$ | 3-Cl-2-pyridyl | Me | Cl |
| H | H | CH$_2$CF$_3$ | Me | Me | Cl |
| H | H | CH$_2$CF$_3$ | Et | Me | Br |
| H | H | CH$_2$CF$_3$ | Ph | Me | Cl |
| H | H | CHF$_2$ | 2-ClPh | Me | H |
| H | H | CHF$_2$ | 2-ClPh | Me | Cl |
| H | H | CHF$_2$ | 2-ClPh | Cl | H |
| H | H | CHF$_2$ | 2-ClPh | Me | Br |
| H | H | CHF$_2$ | 3-Cl-2-pyridyl | Me | H |
| H | H | CHF$_2$ | 3-Cl-2-pyridyl | Cl | H |
| H | H | CHF$_2$ | 3-Cl-2-pyridyl | Me | Br |
| H | H | CHF$_2$ | 3-Cl-2-pyridyl | Me | Cl |
| Me | H | CH$_2$CF$_3$ | 2-ClPh | Me | H |
| Me | H | CH$_2$CF$_3$ | 2-ClPh | Me | Cl |
| Me | H | CH$_2$CF$_3$ | 2-ClPh | Cl | H |
| Me | H | CH$_2$CF$_3$ | 2-ClPh | Me | Br |
| Me | H | CH$_2$CF$_3$ | 3-Cl-2-pyridyl | Me | H |
| Me | H | CH$_2$CF$_3$ | 3-Cl-2-pyridyl | Cl | H |
| Me | H | CH$_2$CF$_3$ | 3-Cl-2-pyridyl | Me | Br |
| Me | H | CH$_2$CF$_3$ | 3-Cl-2-pyridyl | Me | Cl |
| Me | H | CH$_2$CF$_3$ | Me | Me | Cl |
| Me | H | CH$_2$CF$_3$ | Et | Me | Br |
| Me | H | CH$_2$CF$_3$ | Ph | Me | Cl |
| Me | H | CHF$_2$ | 2-ClPh | Me | H |
| Me | H | CHF$_2$ | 2-ClPh | Me | Cl |
| Me | H | CHF$_2$ | 2-ClPh | Cl | H |
| Me | H | CHF$_2$ | 2-ClPh | Me | Br |
| Me | H | CHF$_2$ | 3-Cl-2-pyridyl | Me | H |
| Me | H | CHF$_2$ | 3-Cl-2-pyridyl | Cl | H |
| Me | H | CHF$_2$ | 3-Cl-2-pyridyl | Me | Br |
| Me | H | CHF$_2$ | 3-Cl-2-pyridyl | Me | Cl |
| H | Me | CH$_2$CF$_3$ | 2-ClPh | Me | H |
| H | Me | CH$_2$CF$_3$ | 2-ClPh | Me | Cl |
| H | Me | CH$_2$CF$_3$ | 2-ClPh | Cl | H |
| H | Me | CH$_2$CF$_3$ | 2-ClPh | Me | Br |
| H | Me | CH$_2$CF$_3$ | 3-Cl-2-pyridyl | Me | H |
| H | Me | CH$_2$CF$_3$ | 3-Cl-2-pyridyl | Cl | H |
| H | Me | CH$_2$CF$_3$ | 3-Cl-2-pyridyl | Me | Br |
| H | Me | CH$_2$CF$_3$ | 3-Cl-2-pyridyl | Me | Cl |
| H | Me | CH$_2$CF$_3$ | Me | Me | Cl |
| H | Me | CH$_2$CF$_3$ | Et | Me | Br |
| H | Me | CH$_2$CF$_3$ | Ph | Me | Cl |
| H | Me | CHF$_2$ | 2-ClPh | Me | H |
| H | Me | CHF$_2$ | 2-ClPh | Me | Cl |
| H | Me | CHF$_2$ | 2-ClPh | Cl | H |
| H | Me | CHF$_2$ | 2-ClPh | Me | Br |
| H | Me | CHF$_2$ | 3-Cl-2-pyridyl | Me | H |
| H | Me | CHF$_2$ | 3-Cl-2-pyridyl | Cl | H |
| H | Me | CHF$_2$ | 3-Cl-2-pyridyl | Me | Br |
| H | Me | CHF$_2$ | 3-Cl-2-pyridyl | Me | Cl |
| Me | Me | CH$_2$CF$_3$ | 2-ClPh | Me | H |
| Me | Me | CH$_2$CF$_3$ | 2-ClPh | Me | Cl |
| Me | Me | CH$_2$CF$_3$ | 2-ClPh | Cl | H |
| Me | Me | CH$_2$CF$_3$ | 2-ClPh | Me | Br |

TABLE 30-continued

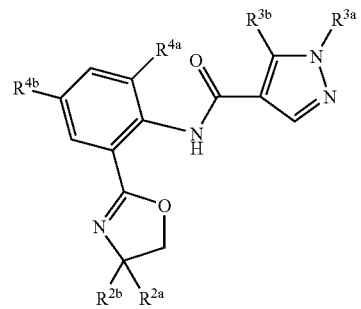

| R$^{2a}$ | R$^{2b}$ | R$^{3a}$ | R$^{3b}$ | R$^{4a}$ | R$^{4b}$ |
|---|---|---|---|---|---|
| Me | Me | CH$_2$CF$_3$ | 3-Cl-2-pyridyl | Me | H |
| Me | Me | CH$_2$CF$_3$ | 3-Cl-2-pyridyl | Cl | H |
| Me | Me | CH$_2$CF$_3$ | 3-Cl-2-pyridyl | Me | Br |
| Me | Me | CH$_2$CF$_3$ | 3-Cl-2-pyridyl | Me | Cl |
| Me | Me | CH$_2$CF$_3$ | Me | Me | Cl |
| Me | Me | CH$_2$CF$_3$ | Et | Me | Br |
| Me | Me | CH$_2$CF$_3$ | Ph | Me | Cl |
| Me | Me | CHF$_2$ | 2-ClPh | Me | H |
| Me | Me | CHF$_2$ | 2-ClPh | Me | Cl |
| Me | Me | CHF$_2$ | 2-ClPh | Cl | H |
| Me | Me | CHF$_2$ | 2-ClPh | Me | Br |
| Me | Me | CHF$_2$ | 3-Cl-2-pyridyl | Me | H |
| Me | Me | CHF$_2$ | 3-Cl-2-pyridyl | Cl | H |
| Me | Me | CHF$_2$ | 3-Cl-2-pyridyl | Me | Br |
| Me | Me | CHF$_2$ | 3-Cl-2-pyridyl | Me | Cl |

TABLE 31

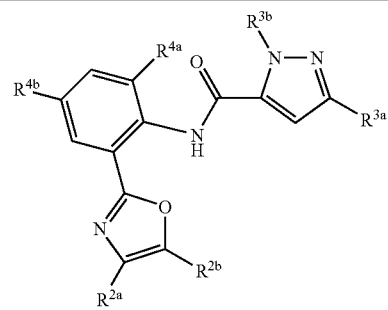

| R$^{2a}$ | R$^{2b}$ | R$^{3a}$ | R$^{3b}$ | R$^{4a}$ | R$^{4b}$ |
|---|---|---|---|---|---|
| H | H | CF$_3$ | 2-ClPh | Me | H |
| H | H | CF$_3$ | 2-ClPh | Me | Cl |
| H | H | CF$_3$ | 2-ClPh | Cl | H |
| H | H | CF$_3$ | Me | Me | Cl |
| H | H | CF$_3$ | Et | Me | Br |
| H | H | CF$_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF$_3$ | 2-ClPh | Me | H |
| Me | H | CF$_3$ | 2-ClPh | Me | Cl |
| Me | H | CF$_3$ | 2-ClPh | Cl | H |
| Me | H | CF$_3$ | Me | Me | Cl |
| Me | H | CF$_3$ | Et | Me | Br |
| Me | H | CF$_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF$_3$ | 2-ClPh | Me | H |
| H | Me | CF$_3$ | 2-ClPh | Me | Cl |
| H | Me | CF$_3$ | 2-ClPh | Cl | H |
| H | Me | CF$_3$ | Me | Me | Cl |

TABLE 31-continued

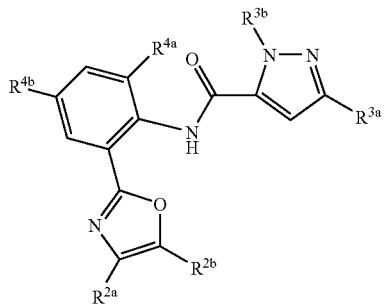

| $R^{2a}$ | $R^{2b}$ | $R^{3a}$ | $R^{3b}$ | $R^{4a}$ | $R^{4b}$ |
|---|---|---|---|---|---|
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |
| H | Me | CF₃ | 3-Cl-2-pyridyl | Cl | H |
| H | Me | CF₃ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF₃ | 3-Cl-2-pyridyl | Me | H |
| Me | Me | CF₃ | 3-Cl-2-pyridyl | Me | Cl |
| Me | Me | CF₃ | 3-Cl-2-pyridyl | Cl | H |
| Me | Me | CF₃ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 32

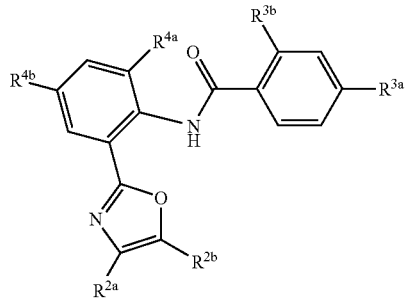

| $R^{2a}$ | $R^{2b}$ | $R^{3a}$ | $R^{3b}$ | $R^{4a}$ | $R^{4b}$ |
|---|---|---|---|---|---|
| H | H | CF₃ | 2-ClPh | Me | H |
| H | H | CF₃ | 2-ClPh | Me | Cl |
| H | H | CF₃ | 2-ClPh | Cl | H |
| H | H | CF₃ | Me | Me | Cl |
| H | H | CF₃ | Et | Me | Br |
| H | H | CF₃ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF₃ | 2-ClPh | Me | H |
| Me | H | CF₃ | 2-ClPh | Me | Cl |
| Me | H | CF₃ | 2-ClPh | Cl | H |
| Me | H | CF₃ | Me | Me | Cl |
| Me | H | CF₃ | Et | Me | Br |
| Me | H | CF₃ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF₃ | 2-ClPh | Me | H |
| H | Me | CF₃ | 2-ClPh | Me | Cl |
| H | Me | CF₃ | 2-ClPh | Cl | H |
| H | Me | CF₃ | Me | Me | Cl |
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |

TABLE 32-continued

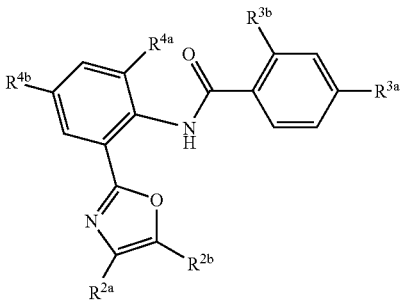

| $R^{2a}$ | $R^{2b}$ | $R^{3a}$ | $R^{3b}$ | $R^{4a}$ | $R^{4b}$ |
|---|---|---|---|---|---|
| H | Me | $CF_3$ | 3-Cl-2-pyridyl | Cl | H |
| H | Me | $CF_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | $CF_3$ | 3-Cl-2-pyridyl | Me | H |
| Me | Me | $CF_3$ | 3-Cl-2-pyridyl | Me | Cl |
| Me | Me | $CF_3$ | 3-Cl-2-pyridyl | Cl | H |
| Me | Me | $CF_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 33

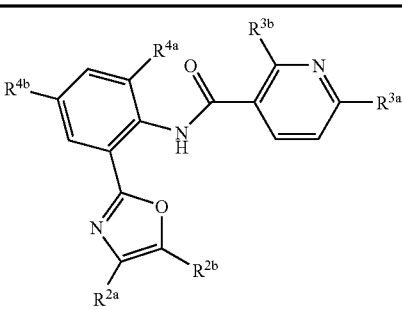

| $R^{2a}$ | $R^{2b}$ | $R^{3a}$ | $R^{3b}$ | $R^{4a}$ | $R^{4b}$ |
|---|---|---|---|---|---|
| H | H | $CF_3$ | 2-ClPh | Me | H |
| H | H | $CF_3$ | 2-ClPh | Me | Cl |
| H | H | $CF_3$ | 2-ClPh | Cl | H |
| H | H | $CF_3$ | Me | Me | Cl |
| H | H | $CF_3$ | Et | Me | Br |
| H | H | $CF_3$ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | $CF_3$ | 2-ClPh | Me | H |
| Me | H | $CF_3$ | 2-ClPh | Me | Cl |
| Me | H | $CF_3$ | 2-ClPh | Cl | H |
| Me | H | $CF_3$ | Me | Me | Cl |
| Me | H | $CF_3$ | Et | Me | Br |
| Me | H | $CF_3$ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | $CF_3$ | 2-ClPh | Me | H |

TABLE 33-continued

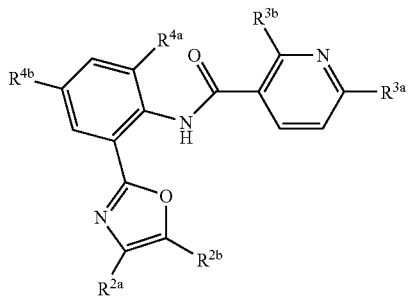

| $R^{2a}$ | $R^{2b}$ | $R^{3a}$ | $R^{3b}$ | $R^{4a}$ | $R^{4b}$ |
|---|---|---|---|---|---|
| H | Me | $CF_3$ | 2-ClPh | Me | Cl |
| H | Me | $CF_3$ | 2-ClPh | Cl | H |
| H | Me | $CF_3$ | Me | Me | Cl |
| H | Me | $CF_3$ | Et | Me | Br |
| H | Me | $CF_3$ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | $CF_3$ | 2-ClPh | Me | H |
| Me | Me | $CF_3$ | 2-ClPh | Me | Cl |
| Me | Me | $CF_3$ | 2-ClPh | Cl | H |
| Me | Me | $CF_3$ | Me | Me | Cl |
| Me | Me | $CF_3$ | Et | Me | Br |
| Me | Me | $CF_3$ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | $CF_3$ | 3-Cl-2-pyridyl | Me | H |
| H | H | $CF_3$ | 3-Cl-2-pyridyl | Me | Cl |
| H | H | $CF_3$ | 3-Cl-2-pyridyl | Cl | H |
| H | H | $CF_3$ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | $CF_3$ | 3-Cl-2-pyridyl | Me | H |
| Me | H | $CF_3$ | 3-Cl-2-pyridyl | Me | Cl |
| Me | H | $CF_3$ | 3-Cl-2-pyridyl | Cl | H |
| Me | H | $CF_3$ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Cl | Cl |
| Me | H | Br | 3-Cl-2-pyridyl | Me | Br |
| Me | H | Cl | 3-Cl-2-pyridyl | Me | Cl |
| H | Me | $CF_3$ | 3-Cl-2-pyridyl | Me | H |
| H | Me | $CF_3$ | 3-Cl-2-pyridyl | Me | Cl |
| H | Me | $CF_3$ | 3-Cl-2-pyridyl | Cl | H |
| H | Me | $CF_3$ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | $CF_3$ | 3-Cl-2-pyridyl | Me | H |
| Me | Me | $CF_3$ | 3-Cl-2-pyridyl | Me | Cl |
| Me | Me | $CF_3$ | 3-Cl-2-pyridyl | Cl | H |
| Me | Me | $CF_3$ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 34

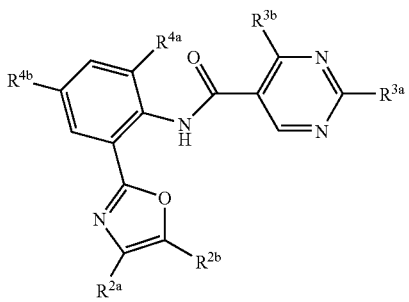

| R²ᵃ | R²ᵇ | R³ᵃ | R³ᵇ | R⁴ᵃ | R⁴ᵇ |
|---|---|---|---|---|---|
| H | H | CF₃ | 2-ClPh | Me | H |
| H | H | CF₃ | 2-ClPh | Me | Cl |
| H | H | CF₃ | 2-ClPh | Cl | H |
| H | H | CF₃ | Me | Me | Cl |
| H | H | CF₃ | Et | Me | Br |
| H | H | CF₃ | Ph | Me | Cl |
| H | H | Br | 2-ClPh | Cl | H |
| H | H | Br | 2-ClPh | Me | Cl |
| H | H | Br | 2-ClPh | Cl | Cl |
| H | H | Cl | 2-ClPh | Me | Cl |
| Me | H | CF₃ | 2-ClPh | Me | H |
| Me | H | CF₃ | 2-ClPh | Me | Cl |
| Me | H | CF₃ | 2-ClPh | Cl | H |
| Me | H | CF₃ | Me | Me | Cl |
| Me | H | CF₃ | Et | Me | Br |
| Me | H | CF₃ | Ph | Me | Cl |
| Me | H | Br | 2-ClPh | Cl | H |
| Me | H | Br | 2-ClPh | Me | Cl |
| Me | H | Br | 2-ClPh | Cl | Cl |
| Me | H | Cl | 2-ClPh | Me | Cl |
| H | Me | CF₃ | 2-ClPh | Me | H |
| H | Me | CF₃ | 2-ClPh | Me | Cl |
| H | Me | CF₃ | 2-ClPh | Cl | H |
| H | Me | CF₃ | Me | Me | Cl |
| H | Me | CF₃ | Et | Me | Br |
| H | Me | CF₃ | Ph | Me | Cl |
| H | Me | Br | 2-ClPh | Cl | H |
| H | Me | Br | 2-ClPh | Me | Cl |
| H | Me | Br | 2-ClPh | Cl | Cl |
| H | Me | Cl | 2-ClPh | Me | Cl |
| Me | Me | CF₃ | 2-ClPh | Me | H |
| Me | Me | CF₃ | 2-ClPh | Me | Cl |
| Me | Me | CF₃ | 2-ClPh | Cl | H |
| Me | Me | CF₃ | Me | Me | Cl |
| Me | Me | CF₃ | Et | Me | Br |
| Me | Me | CF₃ | Ph | Me | Cl |
| Me | Me | Br | 2-ClPh | Cl | H |
| Me | Me | Br | 2-ClPh | Me | Cl |
| Me | Me | Br | 2-ClPh | Cl | Cl |
| Me | Me | Cl | 2-ClPh | Me | Cl |
| H | H | CF₃ | 3-Cl-2-pyridyl | Me | H |
| H | H | CF₃ | 3-Cl-2-pyridyl | Me | Cl |
| H | H | CF₃ | 3-Cl-2-pyridyl | Cl | H |
| H | H | CF₃ | 3-Cl-2-pyridyl | Me | Br |
| H | H | Br | 3-Cl-2-pyridyl | Me | H |
| H | H | Br | 3-Cl-2-pyridyl | Me | Cl |
| H | H | Br | 3-Cl-2-pyridyl | Cl | H |
| H | H | Br | 3-Cl-2-pyridyl | Cl | Cl |
| H | H | Br | 3-Cl-2-pyridyl | Me | Br |
| H | H | Cl | 3-Cl-2-pyridyl | Me | Cl |
| Me | H | CF₃ | 3-Cl-2-pyridyl | Me | H |
| Me | H | CF₃ | 3-Cl-2-pyridyl | Me | Cl |
| Me | H | CF₃ | 3-Cl-2-pyridyl | Cl | H |
| Me | H | CF₃ | 3-Cl-2-pyridyl | Me | Br |
| Me | H | Br | 3-Cl-2-pyridyl | Me | H |
| Me | H | Br | 3-Cl-2-pyridyl | Me | Cl |
| Me | H | Br | 3-Cl-2-pyridyl | Cl | H |
| Me | H | Br | 3-Cl-2-pyridyl | Me | Br |
| Me | H | Cl | 3-Cl-2-pyridyl | Me | Cl |
| H | Me | CF₃ | 3-Cl-2-pyridyl | Me | H |
| H | Me | CF₃ | 3-Cl-2-pyridyl | Me | Cl |

TABLE 34-continued

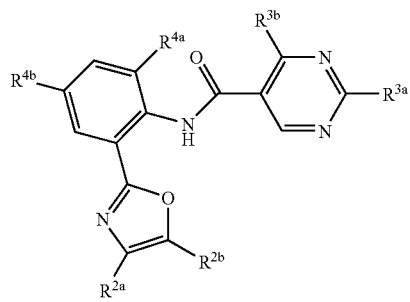

| R²ᵃ | R²ᵇ | R³ᵃ | R³ᵇ | R⁴ᵃ | R⁴ᵇ |
|---|---|---|---|---|---|
| H | Me | CF₃ | 3-Cl-2-pyridyl | Cl | H |
| H | Me | CF₃ | 3-Cl-2-pyridyl | Me | Br |
| H | Me | Br | 3-Cl-2-pyridyl | Me | H |
| H | Me | Br | 3-Cl-2-pyridyl | Me | Cl |
| H | Me | Br | 3-Cl-2-pyridyl | Cl | H |
| H | Me | Br | 3-Cl-2-pyridyl | Cl | Cl |
| H | Me | Br | 3-Cl-2-pyridyl | Me | Br |
| H | Me | Cl | 3-Cl-2-pyridyl | Me | Cl |
| Me | Me | CF₃ | 3-Cl-2-pyridyl | Me | H |
| Me | Me | CF₃ | 3-Cl-2-pyridyl | Me | Cl |
| Me | Me | CF₃ | 3-Cl-2-pyridyl | Cl | H |
| Me | Me | CF₃ | 3-Cl-2-pyridyl | Me | Br |
| Me | Me | Br | 3-Cl-2-pyridyl | Me | H |
| Me | Me | Br | 3-Cl-2-pyridyl | Me | Cl |
| Me | Me | Br | 3-Cl-2-pyridyl | Cl | H |
| Me | Me | Br | 3-Cl-2-pyridyl | Cl | Cl |
| Me | Me | Br | 3-Cl-2-pyridyl | Me | Br |
| Me | Me | Cl | 3-Cl-2-pyridyl | Me | Cl |

TABLE 35

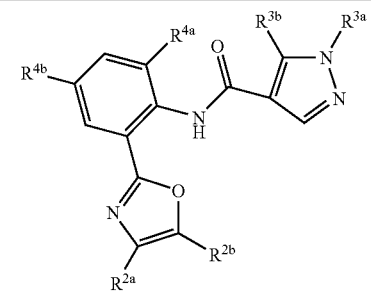

| R²ᵃ | R²ᵇ | R³ᵃ | R³ᵇ | R⁴ᵃ | R⁴ᵇ |
|---|---|---|---|---|---|
| H | H | CH₂CF₃ | 2-ClPh | Me | H |
| H | H | CH₂CF₃ | 2-ClPh | Me | Cl |
| H | H | CH₂CF₃ | 2-ClPh | Cl | H |
| H | H | CH₂CF₃ | 2-ClPh | Me | Br |
| H | H | CH₂CF₃ | 3-Cl-2-pyridyl | Me | H |
| H | H | CH₂CF₃ | 3-Cl-2-pyridyl | Cl | H |
| H | H | CH₂CF₃ | 3-Cl-2-pyridyl | Me | Br |
| H | H | CH₂CF₃ | 3-Cl-2-pyridyl | Me | Cl |
| H | H | CH₂CF₃ | Me | Me | Cl |
| H | H | CH₂CF₃ | Et | Me | Br |
| H | H | CH₂CF₃ | Ph | Me | Cl |
| H | H | CHF₂ | 2-ClPh | Me | H |
| H | H | CHF₂ | 2-ClPh | Me | Cl |
| H | H | CHF₂ | 2-ClPh | Cl | H |
| H | H | CHF₂ | 2-ClPh | Me | Br |
| H | H | CHF₂ | 3-Cl-2-pyridyl | Me | H |
| H | H | CHF₂ | 3-Cl-2-pyridyl | Cl | H |
| H | H | CHF₂ | 3-Cl-2-pyridyl | Me | Br |
| H | H | CHF₂ | 3-Cl-2-pyridyl | Me | Cl |
| Me | H | CH₂CF₃ | 2-ClPh | Me | H |
| Me | H | CH₂CF₃ | 2-ClPh | Me | Cl |
| Me | H | CH₂CF₃ | 2-ClPh | Cl | H |

TABLE 35-continued

| R2a | R2b | R3a | R3b | R4a | R4b |
|---|---|---|---|---|---|
| Me | H | CH2CF3 | 2-ClPh | Me | Br |
| Me | H | CH2CF3 | 3-Cl-2-pyridyl | Me | H |
| Me | H | CH2CF3 | 3-Cl-2-pyridyl | Cl | H |
| Me | H | CH2CF3 | 3-Cl-2-pyridyl | Me | Br |
| Me | H | CH2CF3 | 3-Cl-2-pyridyl | Me | Cl |
| Me | H | CH2CF3 | Me | Me | Cl |
| Me | H | CH2CF3 | Et | Me | Br |
| Me | H | CH2CF3 | Ph | Me | Cl |
| Me | H | CHF2 | 2-ClPh | Me | H |
| Me | H | CHF2 | 2-ClPh | Me | Cl |
| Me | H | CHF2 | 2-ClPh | Cl | H |
| Me | H | CHF2 | 2-ClPh | Me | Br |
| Me | H | CHF2 | 3-Cl-2-pyridyl | Me | H |
| Me | H | CHF2 | 3-Cl-2-pyridyl | Cl | H |
| Me | H | CHF2 | 3-Cl-2-pyridyl | Me | Br |
| Me | H | CHF2 | 3-Cl-2-pyridyl | Me | Cl |
| H | Me | CH2CF3 | 2-ClPh | Me | H |
| H | Me | CH2CF3 | 2-ClPh | Me | Cl |
| H | Me | CH2CF3 | 2-ClPh | Cl | H |
| H | Me | CH2CF3 | 2-ClPh | Me | Br |
| H | Me | CH2CF3 | 3-Cl-2-pyridyl | Me | H |
| H | Me | CH2CF3 | 3-Cl-2-pyridyl | Cl | H |
| H | Me | CH2CF3 | 3-Cl-2-pyridyl | Me | Br |
| H | Me | CH2CF3 | 3-Cl-2-pyridyl | Me | Cl |
| H | Me | CH2CF3 | Me | Me | Cl |
| H | Me | CH2CF3 | Et | Me | Br |
| H | Me | CH2CF3 | Ph | Me | Cl |
| H | Me | CHF2 | 2-ClPh | Me | H |
| H | Me | CHF2 | 2-ClPh | Me | Cl |
| H | Me | CHF2 | 2-ClPh | Cl | H |
| H | Me | CHF2 | 2-ClPh | Me | Br |
| H | Me | CHF2 | 3-Cl-2-pyridyl | Me | H |
| H | Me | CHF2 | 3-Cl-2-pyridyl | Cl | H |
| H | Me | CHF2 | 3-Cl-2-pyridyl | Me | Br |
| H | Me | CHF2 | 3-Cl-2-pyridyl | Me | Cl |
| Me | Me | CH2CF3 | 2-ClPh | Me | H |
| Me | Me | CH2CF3 | 2-ClPh | Me | Cl |
| Me | Me | CH2CF3 | 2-ClPh | Cl | H |
| Me | Me | CH2CF3 | 2-ClPh | Me | Br |
| Me | Me | CH2CF3 | 3-Cl-2-pyridyl | Me | H |
| Me | Me | CH2CF3 | 3-Cl-2-pyridyl | Cl | H |
| Me | Me | CH2CF3 | 3-Cl-2-pyridyl | Me | Br |
| Me | Me | CH2CF3 | 3-Cl-2-pyridyl | Me | Cl |
| Me | Me | CH2CF3 | Me | Me | Cl |
| Me | Me | CH2CF3 | Et | Me | Br |
| Me | Me | CH2CF3 | Ph | Me | Cl |
| Me | Me | CHF2 | 2-ClPh | Me | H |
| Me | Me | CHF2 | 2-ClPh | Me | Cl |
| Me | Me | CHF2 | 2-ClPh | Cl | H |
| Me | Me | CHF2 | 2-ClPh | Me | Br |
| Me | Me | CHF2 | 3-Cl-2-pyridyl | Me | H |
| Me | Me | CHF2 | 3-Cl-2-pyridyl | Cl | H |
| Me | Me | CHF2 | 3-Cl-2-pyridyl | Me | Br |
| Me | Me | CHF2 | 3-Cl-2-pyridyl | Me | Cl |

TABLE 36

| R2 | R3a | R3b | R4a | R4b | R2a | R3a | R3b | R4a | R4b |
|---|---|---|---|---|---|---|---|---|---|
| H | CF3 | 2-ClPh | Me | H | H | CF3 | 3-Cl-2-pyridyl | Me | H |
| H | CF3 | 2-ClPh | Me | Cl | H | CF3 | 3-Cl-2-pyridyl | Me | Cl |
| H | CF3 | 2-ClPh | Cl | H | H | CF3 | 3-Cl-2-pyridyl | Cl | H |
| H | CF3 | Me | Me | Cl | H | CF3 | 3-Cl-2-pyridyl | Me | Br |
| H | CF3 | Et | Me | Br | H | Br | 3-Cl-2-pyridyl | Me | H |
| H | CF3 | Ph | Me | Cl | H | Br | 3-Cl-2-pyridyl | Me | Cl |
| H | Br | 2-ClPh | Cl | H | H | Br | 3-Cl-2-pyridyl | Cl | H |
| H | Br | 2-ClPh | Me | Cl | H | Br | 3-Cl-2-pyridyl | Cl | Cl |
| H | Br | 2-ClPh | Cl | H | H | Br | 3-Cl-2-pyridyl | Me | Br |
| H | Cl | 2-ClPh | Me | Cl | H | Cl | 3-Cl-2-pyridyl | Me | Cl |
| Me | CF3 | 2-ClPh | Me | H | Me | CF3 | 3-Cl-2-pyridyl | Me | H |
| Me | CF3 | 2-ClPh | Me | Cl | Me | CF3 | 3-Cl-2-pyridyl | Me | Cl |
| Me | CF3 | 2-ClPh | Cl | H | Me | CF3 | 3-Cl-2-pyridyl | Cl | H |
| Me | CF3 | Me | Me | Cl | Me | CF3 | 3-Cl-2-pyridyl | Me | Br |
| Me | CF3 | Et | Me | Br | Me | Br | 3-Cl-2-pyridyl | Me | H |
| Me | CF3 | Ph | Me | Cl | Me | Br | 3-Cl-2-pyridyl | Me | Cl |
| Me | Br | 2-ClPh | Cl | H | Me | Br | 3-Cl-2-pyridyl | Cl | H |
| Me | Br | 2-ClPh | Me | Cl | Me | Br | 3-Cl-2-pyridyl | Cl | Cl |
| Me | Br | 2-ClPh | Cl | Cl | Me | Br | 3-Cl-2-pyridyl | Me | Br |
| Me | Cl | 2-ClPh | Me | Cl | Me | Cl | 3-Cl-2-pyridyl | Me | Cl |

TABLE 37

| R2 | R3a | R3b | R4a | R4b | R2a | R3a | R3b | R4a | R4b |
|---|---|---|---|---|---|---|---|---|---|
| H | CF3 | 2-ClPh | Me | H | H | CF3 | 3-Cl-2-pyridyl | Me | H |
| H | CF3 | 2-ClPh | Me | Cl | H | CF3 | 3-Cl-2-pyridyl | Me | Cl |
| H | CF3 | 2-ClPh | Cl | H | H | CF3 | 3-Cl-2-pyridyl | Cl | H |
| H | CF3 | Me | Me | Cl | H | CF3 | 3-Cl-2-pyridyl | Me | Br |
| H | CF3 | Et | Me | Br | H | Br | 3-Cl-2-pyridyl | Me | H |
| H | CF3 | Ph | Me | Cl | H | Br | 3-Cl-2-pyridyl | Me | Cl |
| H | Br | 2-ClPh | Cl | H | H | Br | 3-Cl-2-pyridyl | Cl | H |
| H | Br | 2-ClPh | Me | Cl | H | Br | 3-Cl-2-pyridyl | Cl | Cl |
| H | Br | 2-ClPh | Cl | Cl | H | Br | 3-Cl-2-pyridyl | Me | Br |
| H | Cl | 2-ClPh | Me | Cl | H | Cl | 3-Cl-2-pyridyl | Me | Cl |
| Me | CF3 | 2-ClPh | Me | H | Me | CF3 | 3-Cl-2-pyridyl | Me | H |
| Me | CF3 | 2-ClPh | Me | Cl | Me | CF3 | 3-Cl-2-pyridyl | Me | Cl |
| Me | CF3 | 2-ClPh | Cl | H | Me | CF3 | 3-Cl-2-pyridyl | Cl | H |
| Me | CF3 | Me | Me | Cl | Me | CF3 | 3-Cl-2-pyridyl | Me | Br |
| Me | CF3 | Et | Me | Br | Me | Br | 3-Cl-2-pyridyl | Me | H |
| Me | CF3 | Ph | Me | Cl | Me | Br | 3-Cl-2-pyridyl | Me | Cl |
| Me | Br | 2-ClPh | Cl | H | Me | Br | 3-Cl-2-pyridyl | Cl | H |
| Me | Br | 2-ClPh | Me | Cl | Me | Br | 3-Cl-2-pyridyl | Cl | Cl |
| Me | Br | 2-ClPh | Cl | Cl | Me | Br | 3-Cl-2-pyridyl | Me | Br |
| Me | Cl | 2-ClPh | Me | Cl | Me | Cl | 3-Cl-2-pyridyl | Me | Cl |

TABLE 38

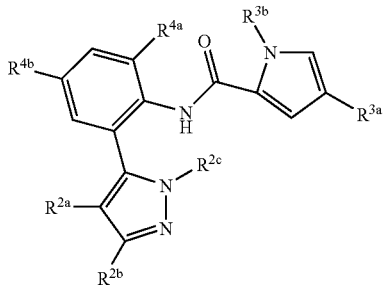

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 3-Cl-2-pyridyl | Me | H |
| H | H | H | CF3 | 3-Cl-2-pyridyl | Me | H |
| H | H | H | CF3 | 2-ClPh | Cl | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |
| Me | H | H | CF3 | 3-Cl-2-pyridyl | Cl | H |
| Me | H | H | CF3 | 3-Cl-2-pyridyl | Me | Br |
| Me | H | H | CF3 | Me | Me | Cl |
| Me | H | H | CF3 | Et | Me | Br |
| Me | H | H | CF3 | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | CF3 | 2-ClPh | Me | H |
| H | Me | H | CF3 | 2-ClPh | Me | Cl |
| H | Me | H | CF3 | 3-Cl-2-pyridyl | Me | H |
| H | Me | H | CF3 | 3-Cl-2-pyridyl | Me | H |
| H | Me | H | CF3 | 2-ClPh | Cl | H |
| H | Me | H | CF3 | 3-Cl-2-pyridyl | Cl | H |
| H | Me | H | CF3 | 3-Cl-2-pyridyl | Me | Br |
| H | Me | H | CF3 | Me | Me | Cl |
| H | Me | H | CF3 | Et | Me | Br |
| H | Me | H | CF3 | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | CF3 | 2-ClPh | Me | H |
| Me | Me | H | CF3 | 2-ClPh | Me | Cl |
| Me | Me | H | CF3 | 3-Cl-2-pyridyl | Me | H |
| Me | Me | H | CF3 | 3-Cl-2-pyridyl | Me | H |
| Me | Me | H | CF3 | 2-ClPh | Cl | H |
| Me | Me | H | CF3 | 3-Cl-2-pyridyl | Cl | H |
| Me | Me | H | CF3 | 3-Cl-2-pyridyl | Me | Br |
| Me | Me | H | CF3 | Me | Me | Cl |
| Me | Me | H | CF3 | Et | Me | Br |
| Me | Me | H | CF3 | Ph | Me | Cl |
| Me | Me | H | Br | 2-ClPh | Cl | H |

TABLE 38-continued

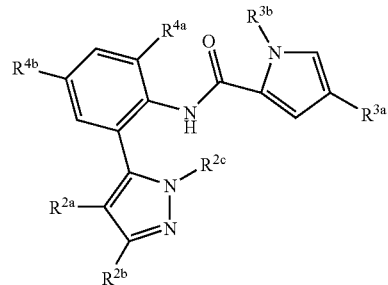

| R2a | R2b | R2c | R3a | R3b | R4a | R4b |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | CF3 | 2-ClPh | Me | H |
| H | H | Me | CF3 | 2-ClPh | Me | Cl |
| H | H | Me | CF3 | 3-Cl-2-pyridyl | Me | H |
| H | H | Me | CF3 | 3-Cl-2-pyridyl | Me | Cl |
| Me | H | Me | CF3 | 3-Cl-2-pyridyl | Me | H |
| Me | H | Me | CF3 | 3-Cl-2-pyridyl | Me | Cl |
| H | Me | Me | CF3 | 3-Cl-2-pyridyl | Me | H |
| H | Me | Me | CF3 | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 39

| R2a | R2b | R2c | R3a | R3b | R4a | R4b |
|---|---|---|---|---|---|---|
| H | H | H | CF3 | 2-ClPh | Me | H |
| H | H | H | CF3 | 2-ClPh | Me | Cl |
| H | H | H | CF3 | 3-Cl-2-pyridyl | Me | H |
| H | H | H | CF3 | 3-Cl-2-pyridyl | Me | H |
| H | H | H | CF3 | 2-ClPh | Cl | H |
| H | H | H | CF3 | 3-Cl-2-pyridyl | Cl | H |
| H | H | H | CF3 | 3-Cl-2-pyridyl | Me | Br |
| H | H | H | CF3 | Me | Me | Cl |
| H | H | H | CF3 | Et | Me | Br |
| H | H | H | CF3 | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | CF3 | 2-ClPh | Me | H |
| Me | H | H | CF3 | 2-ClPh | Me | Cl |
| Me | H | H | CF3 | 3-Cl-2-pyridyl | Me | H |
| Me | H | H | CF3 | 3-Cl-2-pyridyl | Me | H |
| Me | H | H | CF3 | 2-ClPh | Cl | H |
| Me | H | H | CF3 | 3-Cl-2-pyridyl | Cl | H |
| Me | H | H | CF3 | 3-Cl-2-pyridyl | Me | Br |

TABLE 39-continued

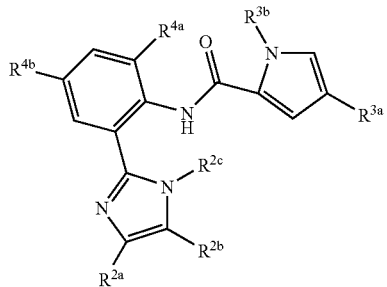

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | H | H | $CF_3$ | Me | Me | Cl |
| Me | H | H | $CF_3$ | Et | Me | Br |
| Me | H | H | $CF_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | $CF_3$ | 2-ClPh | Me | H |
| H | Me | H | $CF_3$ | 2-ClPh | Me | Cl |
| H | Me | H | $CF_3$ | 3-Cl-2-pyridyl | Me | H |
| H | Me | H | $CF_3$ | 3-Cl-2-pyridyl | Me | H |
| H | Me | H | $CF_3$ | 2-ClPh | Cl | H |
| H | Me | H | $CF_3$ | 3-Cl-2-pyridyl | Cl | H |
| H | Me | H | $CF_3$ | 3-Cl-2-pyridyl | Me | Br |
| H | Me | H | $CF_3$ | Me | Me | Cl |
| H | Me | H | $CF_3$ | Et | Me | Br |
| H | Me | H | $CF_3$ | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | $CF_3$ | 2-ClPh | Me | H |
| Me | Me | H | $CF_3$ | 2-ClPh | Me | Cl |
| Me | Me | H | $CF_3$ | 3-Cl-2-pyridyl | Me | H |
| Me | Me | H | $CF_3$ | 3-Cl-2-pyridyl | Me | H |
| Me | Me | H | $CF_3$ | 2-ClPh | Cl | H |
| Me | Me | H | $CF_3$ | 3-Cl-2-pyridyl | Cl | H |
| Me | Me | H | $CF_3$ | 3-Cl-2-pyridyl | Me | Br |
| Me | Me | H | $CF_3$ | Me | Me | Cl |
| Me | Me | H | $CF_3$ | Et | Me | Br |
| Me | Me | H | $CF_3$ | Ph | Me | Cl |
| Me | Me | H | Br | 2-ClPh | Cl | H |
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | $CF_3$ | 2-ClPh | Me | H |
| H | H | Me | $CF_3$ | 2-ClPh | Me | Cl |
| H | H | Me | $CF_3$ | 3-Cl-2-pyridyl | Me | H |
| H | H | Me | $CF_3$ | 3-Cl-2-pyridyl | Me | Cl |
| Me | H | Me | $CF_3$ | 3-Cl-2-pyridyl | Me | H |
| Me | H | Me | $CF_3$ | 3-Cl-2-pyridyl | Me | Cl |
| H | Me | Me | $CF_3$ | 3-Cl-2-pyridyl | Me | H |
| H | Me | Me | $CF_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 40

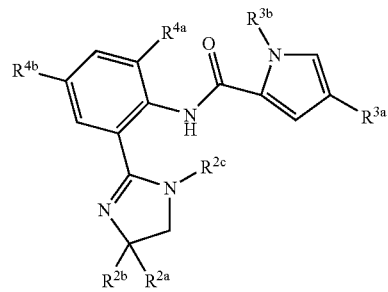

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | $CF_3$ | 2-ClPh | Me | H |
| H | H | H | $CF_3$ | 2-ClPh | Me | Cl |
| H | H | H | $CF_3$ | 3-Cl-2-pyridyl | Me | H |
| H | H | H | $CF_3$ | 3-Cl-2-pyridyl | Me | H |
| H | H | H | $CF_3$ | 2-ClPh | Cl | H |
| H | H | H | $CF_3$ | 3-Cl-2-pyridyl | Cl | H |
| H | H | H | $CF_3$ | 3-Cl-2-pyridyl | Me | Br |
| H | H | H | $CF_3$ | Me | Me | Cl |
| H | H | H | $CF_3$ | Et | Me | Br |
| H | H | H | $CF_3$ | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | $CF_3$ | 2-ClPh | Me | H |
| Me | H | H | $CF_3$ | 2-ClPh | Me | Cl |
| Me | H | H | $CF_3$ | 3-Cl-2-pyridyl | Me | H |
| Me | H | H | $CF_3$ | 3-Cl-2-pyridyl | Me | H |
| Me | H | H | $CF_3$ | 2-ClPh | Cl | H |
| Me | H | H | $CF_3$ | 3-Cl-2-pyridyl | Cl | H |
| Me | H | H | $CF_3$ | 3-Cl-2-pyridyl | Me | Br |
| Me | H | H | $CF_3$ | Me | Me | Cl |
| Me | H | H | $CF_3$ | Et | Me | Br |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | $CF_3$ | 2-ClPh | Me | H |
| H | H | Me | $CF_3$ | 2-ClPh | Me | Cl |
| H | H | Me | $CF_3$ | 3-Cl-2-pyridyl | Me | H |
| H | H | Me | $CF_3$ | 3-Cl-2-pyridyl | Me | Cl |
| Me | H | Me | $CF_3$ | 3-Cl-2-pyridyl | Me | H |
| Me | H | Me | $CF_3$ | 3-Cl-2-pyridyl | Me | Cl |
| H | Me | Me | $CF_3$ | 3-Cl-2-pyridyl | Me | H |
| H | Me | Me | $CF_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

TABLE 41

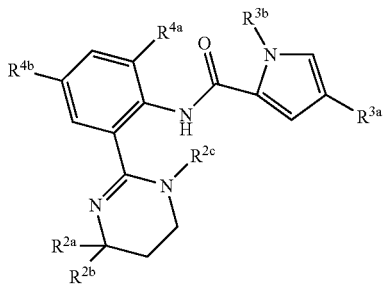

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| H | H | H | $CF_3$ | 2-ClPh | Me | H |
| H | H | H | $CF_3$ | 2-ClPh | Me | Cl |
| H | H | H | $CF_3$ | 3-Cl-2-pyridyl | Me | H |
| H | H | H | $CF_3$ | 3-Cl-2-pyridyl | Me | H |
| H | H | H | $CF_3$ | 2-ClPh | Cl | H |
| H | H | H | $CF_3$ | 3-Cl-2-pyridyl | Cl | H |
| H | H | H | $CF_3$ | 3-Cl-2-pyridyl | Me | Br |
| H | H | H | $CF_3$ | Me | Me | Cl |
| H | H | H | $CF_3$ | Et | Me | Br |
| H | H | H | $CF_3$ | Ph | Me | Cl |
| H | H | H | Br | 2-ClPh | Cl | H |
| H | H | H | Cl | 2-ClPh | Me | Cl |
| H | H | H | Br | 3-Cl-2-pyridyl | Me | H |
| H | H | H | Br | 3-Cl-2-pyridyl | Me | Cl |
| H | H | H | Cl | 3-Cl-2-pyridyl | Me | Br |
| H | H | H | Br | 2-ClPh | Cl | H |
| H | H | H | Br | 3-Cl-2-pyridyl | Cl | H |
| Me | H | H | $CF_3$ | 2-ClPh | Me | H |
| Me | H | H | $CF_3$ | 2-ClPh | Me | Cl |
| Me | H | H | $CF_3$ | 3-Cl-2-pyridyl | Me | H |
| Me | H | H | $CF_3$ | 3-Cl-2-pyridyl | Me | H |
| Me | H | H | $CF_3$ | 2-ClPh | Cl | H |
| Me | H | H | $CF_3$ | 3-Cl-2-pyridyl | Cl | H |
| Me | H | H | $CF_3$ | 3-Cl-2-pyridyl | Me | Br |
| Me | H | H | $CF_3$ | Me | Me | Cl |
| Me | H | H | $CF_3$ | Et | Me | Br |
| Me | H | H | $CF_3$ | Ph | Me | Cl |
| Me | H | H | Br | 2-ClPh | Cl | H |
| Me | H | H | Cl | 2-ClPh | Me | Cl |
| Me | H | H | Br | 3-Cl-2-pyridyl | Me | H |
| Me | H | H | Br | 3-Cl-2-pyridyl | Me | Cl |
| Me | H | H | Cl | 3-Cl-2-pyridyl | Me | Br |
| Me | H | H | Br | 2-ClPh | Cl | H |
| Me | H | H | Br | 3-Cl-2-pyridyl | Cl | H |
| H | Me | H | $CF_3$ | 2-ClPh | Me | H |
| H | Me | H | $CF_3$ | 2-ClPh | Me | Cl |
| H | Me | H | $CF_3$ | 3-Cl-2-pyridyl | Me | H |
| H | Me | H | $CF_3$ | 3-Cl-2-pyridyl | Me | H |
| H | Me | H | $CF_3$ | 2-ClPh | Cl | H |
| H | Me | H | $CF_3$ | 3-Cl-2-pyridyl | Cl | H |
| H | Me | H | $CF_3$ | 3-Cl-2-pyridyl | Me | Br |
| H | Me | H | $CF_3$ | Me | Me | Cl |
| H | Me | H | $CF_3$ | Et | Me | Br |
| H | Me | H | $CF_3$ | Ph | Me | Cl |
| H | Me | H | Br | 2-ClPh | Cl | H |
| H | Me | H | Cl | 2-ClPh | Me | Cl |
| H | Me | H | Br | 3-Cl-2-pyridyl | Me | H |
| H | Me | H | Br | 3-Cl-2-pyridyl | Me | Cl |
| H | Me | H | Cl | 3-Cl-2-pyridyl | Me | Br |
| H | Me | H | Br | 2-ClPh | Cl | H |
| H | Me | H | Br | 3-Cl-2-pyridyl | Cl | H |
| Me | Me | H | $CF_3$ | 2-ClPh | Me | H |
| Me | Me | H | $CF_3$ | 2-ClPh | Me | Cl |
| Me | Me | H | $CF_3$ | 3-Cl-2-pyridyl | Me | H |
| Me | Me | H | $CF_3$ | 3-Cl-2-pyridyl | Me | H |
| Me | Me | H | $CF_3$ | 2-ClPh | Cl | H |
| Me | Me | H | $CF_3$ | 3-Cl-2-pyridyl | Cl | H |
| Me | Me | H | $CF_3$ | 3-Cl-2-pyridyl | Me | Br |
| Me | Me | H | $CF_3$ | Me | Me | Cl |
| Me | Me | H | $CF_3$ | Et | Me | Br |
| Me | Me | H | $CF_3$ | Ph | Me | Cl |
| Me | Me | H | Br | 2-ClPh | Cl | H |

TABLE 41-continued

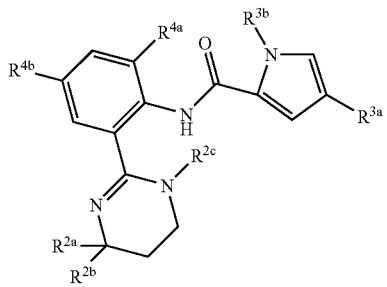

| $R^{2a}$ | $R^{2b}$ | $R^{2c}$ | $R^{3a}$ | $R^{3b}$ | $R^{4a}$ | $R^{4b}$ |
|---|---|---|---|---|---|---|
| Me | Me | H | Cl | 2-ClPh | Me | Cl |
| Me | Me | H | Br | 3-Cl-2-pyridyl | Me | H |
| Me | Me | H | Br | 3-Cl-2-pyridyl | Me | Cl |
| Me | Me | H | Cl | 3-Cl-2-pyridyl | Me | Br |
| Me | Me | H | Br | 2-ClPh | Cl | H |
| Me | Me | H | Br | 3-Cl-2-pyridyl | Cl | H |
| H | H | Me | $CF_3$ | 2-ClPh | Me | H |
| H | H | Me | $CF_3$ | 2-ClPh | Me | Cl |
| H | H | Me | $CF_3$ | 3-Cl-2-pyridyl | Me | H |
| H | H | Me | $CF_3$ | 3-Cl-2-pyridyl | Me | Cl |
| Me | H | Me | $CF_3$ | 3-Cl-2-pyridyl | Me | H |
| Me | H | Me | $CF_3$ | 3-Cl-2-pyridyl | Me | Cl |
| H | Me | Me | $CF_3$ | 3-Cl-2-pyridyl | Me | H |
| H | Me | Me | $CF_3$ | 3-Cl-2-pyridyl | Me | Cl |
| H | Me | Me | Br | 3-Cl-2-pyridyl | Me | H |
| H | Me | Me | Br | 3-Cl-2-pyridyl | Me | Cl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation, alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |

-continued

|  | Weight Percent | | |
| --- | --- | --- | --- |
|  | Active Ingredient | Diluent | Surfactant |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, thing, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
| --- | --- |
| Compound 1 | 10.0% |
| attapulgite granules (low volatile matter, 0.71/0.30 mm; U.S.S. No. 25-50 sieves) | 90.0%. |

EXAMPLE C

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
| --- | --- |
| Compound 1 | 20.0% |
| blend of oil soluble sulfonates and polyoxyethylene ethers | 10.0% |
| isophorone | 70.0%. |

EXAMPLE E

| Granule | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage lopper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginzosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahiniai* Mizukubo), German cockroach (*Blatella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyrphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g. *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armingera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrch-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculis* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphosmethyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, flufenerim, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux-mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametpyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl, clothiazoben/benclothiaz and fenamiphos; bactericides such as streptomycin; acaricides such as amidoflumet, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of exogenously applied invertebrate pest control compounds of this invention may be synergistic with the expressed toxin proteins.

A general reference for these agricultural protectants is *The Pesticide Manual* 12*th Edition*, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound or agent is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A through F for compound descriptions. The following abbreviation is used in the Index Tables that follow: Me is methyl. The abbreviation "Ex." stands for "Example" and is followed by a number indicating in which example the compound is prepared.

INDEX TABLE A

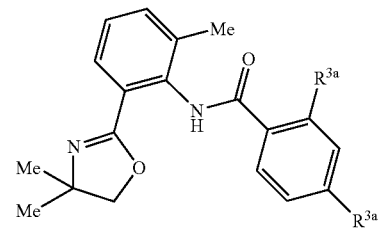

| Compound | $R^{3a}$ | $R^{3b}$ | m.p. (° C.) |
|---|---|---|---|
| 1 | H | $CF_3$ | 200-203 |
| 2 | H | $OCF_3$ | oil* |
| 3 | Me | Br | 122-125 |
| 4 | Me | $CF_3$ | 174-178 |

*See Index Table F for $^1$H NMR data

INDEX TABLE B

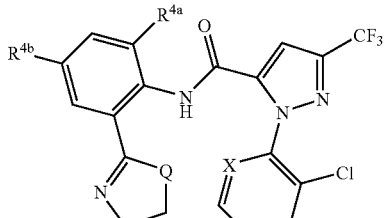

| Compound | Q | $R^{4a}$ | $R^{4b}$ | X | m.p. (° C.) |
|---|---|---|---|---|---|
| 5 (Ex. 4) | NH | Cl | Cl | N | * |
| 6 (Ex. 5) | NMe | Me | H | CH | 244-246 |
| 7 | O | Me | H | N | 217-220 |
| 8 | NMe | Me | H | N | * |
| 9 | NMe | Me | Br | N | * |
| 10 (Ex. 7) | NMe | Me | Br | CH | * |
| 11 (Ex. 1) | NH | Me | Br | N | * |

* See Index Table F for $^1$H NMR data

INDEX TABLE C

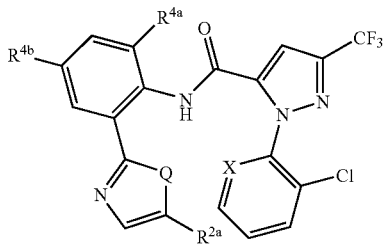

| Compound | Q | $R^{2a}$ | $R^{4a}$ | $R^{4b}$ | X | m.p. (° C.) |
|---|---|---|---|---|---|---|
| 12 | NMe | H | Me | H | N | * |
| 13 (Ex. 2) | NH | H | Me | H | N | 224-226 |
| 14 (Ex. 6) | NMe | H | Me | H | CH | * |
| 15 (Ex. 3) | NH | Br | Me | H | N | * |

* See Index Table F for $^1$H NMR data

INDEX TABLE D

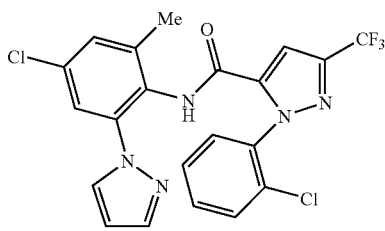

| Compound | m.p. (° C.) |
|---|---|
| 16 | 87-89 |

INDEX TABLE E

| Compound | X | m.p. (° C.) |
|---|---|---|
| 17 (Ex. 8) | N | * |

* See Index Table F for $^1$H NMR data

INDEX TABLE F

| Cpd. | $^1$H NMR Data (CDCl$_3$ solution unless indicated otherwise)$^a$ |
|---|---|
| 5 | δ 7.30 (d, 1H), 7.23 (d, 1H), 6.8 (bs, 2H), 4.7-4.6 (bs, 1H), 3.77 (bs, 4H). |
| 8 | δ 8.5 (dd, 1H), 7.9 (dd, 1H), 7.4 (dd, 1H), 7.29 (s, 1H), 7.2-7.1 (m, 3H), 3.87 (t, 2H), 3.43 (t, 2H), 2.69 (s, 3H), 2.14 (s, 3H). |
| 9 | δ 8.5 (dd, 1H), 7.9 (dd, 1H), 7.5 (dd, 1H), 7.4 (m, 2H), 7.30 (s, 1H), 3.79 (s, 4H), 2.20 (s, 3H). |
| 10 | δ 8.02 (s, 1H), 7.7-7.6 (d, 1H), 7.5-7.4 (m, 4H), 7.3 (d, 1H), 4.0-3.8 (bm, 4H), 2.94 (s, 3H), 2.34 (s, 3H). |
| 11 | δ 8.5 (dd, 1H), 7.9 (dd, 1H), 7.5 (dd, 1H), 7.4 (m, 2H), 7.30 (s, 1H), 3.79 (s, 4H), 2.20 (s, 3H). |
| 12 | δ 10.7 (s, 1H), 8.5 (dd, 1H), 7.9-7.8 (dd, 1H), 7.4 (m, 1H), 7.3-7.2 (m, 3H), 7.2 (d, 1H), 7.0-6.9 (d, 1H), 3.67 (s, 3H), 2.27 (s, 3H). |
| 14 | δ 10.5 (bs, 1H), 7.5 (m, 1H), 7.4 (m, 3H), 7.3-7.2 (m, 4H), 7.13 (d, 1H), 6.95 (d, 1H), 3.65 (s, 3H), 2.26 (s, 3H). |
| 15 | δ 10.7 (s, 1H), 8.5 (dd, 1H), 7.9-7.8 (dd, 1H), 7.4 (m, 1H), 7.3-7.2 (m, 3H), 7.2 (d, 1H), 7.0-6.9 (d, 1H), 3.67 (s, 3H), 2.27 (s, 3H). |
| 17 | δ 11.3 (bs, 1H), 8.5 (dd, 1H), 7.9 (dd, 1H), 7.5-7.4 (m, 1H), 7.4-7.2 (m, 3H), 7.18 (s, 1H), 3.85 (t, 3H), 2.54 (t, 2H), 2.23 (s, 3H). |

$^a$$^1$H NMR data are in ppm downfield from tetramethylsilane. Couplings are designated by (s)—singlet, (d)—doublet, (t)—triplet, (q)—quartet, (m)—multiplet, (dd)—doublet of doublets, (dt)—doublet of triplets, (br s)—broad singlet.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae-growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with 1/8 JJ custom body (Spraying Systems Co.) positioned 1.27 cm (0.5 inches) above the top of each test unit. All experimental compounds in this screen were sprayed at 250 ppm (or lower) and replicated three-times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (20% or less feeding damage): 1*, 2*, 3, 4*, 5*, 6, 7*, 8, 10*, 11*, 12*, 13*, 14*, 15*, and 17*.

Test B

For evaluating control of fall armyworm (*Spodoptera frugiperda*) the test unit consisted of a small open container with a 45-day-old corn (maize) plant inside. This was pre-infested with 10-15 1-day-old larvae on a piece of insect diet by use of a core sampler as described for Test A.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided excellent levels of plant protection (20% or less feeding damage): 7*, 10, 12*, 13*, 14* and 17*.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided excellent levels of plant protection (20% or less feeding damage): 7*, 10*, 11*, 12*, 13, 14* and 17*.

*Tested at 50 ppm.

What is claimed is:

1. A compound of Formula I, an N-oxide or salt thereof

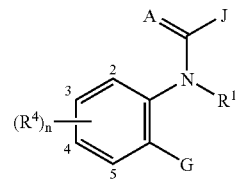

wherein
A is O or S;
G is a 6-membered nonaromatic heterocyclic ring optionally including one or two ring members independently selected from the group consisting of C(=O), SO or S(O)$_2$, each ring optionally substituted with from one to four $R^2$;
J is a pyrazole ring selected from the group consisting of J-5, J-6 and J-7, each ring substituted with $R^3$ and optionally substituted with $R^6$ or $R^7$;

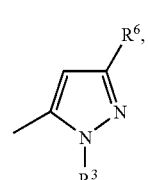

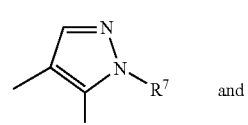 and

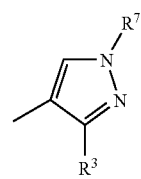

$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents independently selected from the group consisting of halogen, CN, NO$_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or C(=A)J;

each $R^2$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, CO$_2$H, CONH$_2$, NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or each $R^2$ is independently a phenyl, benzyl, benzoyl, phenoxy or 5- or 6-membered heteroaromatic ring, a naphthyl ring system, or an aromatic or nonaromatic 8-, 9- or 10-membered fused heterobicyclic ring system, each ring or ring system substituted with from one to three substituents independently selected from $R^5$;

$R^3$ is pyridine substituted with from one to three substituents independently selected from $R^5$;

each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, or $C_3$-$C_6$ trialkylsilyl; or each $R^4$ is independently a phenyl, benzyl or phenoxy ring, each ring substituted with from one to three substituents independently selected from $R^5$;

each $R^5$ is independently H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_7$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^6$ is independently H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio;

$R^7$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl; and n is an integer from 1 to 4.

2. The compound of claim 1 wherein
A is O;
G is selected from the group consisting of G-7 and G-43, each G optionally substituted with from one to four $R^2$

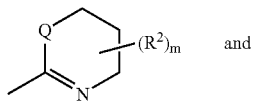

and

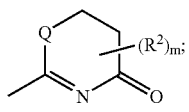

Q is O, S or $NR^2$;
one $R^4$ group is attached to remainder of Formula I at either the 2-position or 5-position of the phenyl ring, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl; and
m is an integer from 0 to 4.

3. The compound of claim 2 wherein
$R^1$ is H or $C_2$-$C_6$ alkyl;
and
n is 1 or 2.

4. The compound of claim 3 wherein
$R^1$ is H;
one $R^4$ is attached to remainder of Formula I at the 2-position of the phenyl ring ortho to the $NR^1C(\!=\!A)J$ moiety and is selected from the group consisting of $C_1$-$C_3$ alkyl, $CF_3$, $OCF_3$, $OCHF_2$, $S(O)_pCF_3$, $S(O)CHF_2$ and halogen and optionally a second $R^4$ is attached at the 4-position of the phenyl ring para to the $NR^1C(\!=\!A)J$ moiety and is selected from the group consisting of halogen, $C_1$-$C_3$ alkyl and $C_1$-$C_3$ haloalkyl; and
p is 0, 1 or 2.

5. The compound of claim 4 wherein
$R^3$ is H, $C_1$-$C_4$ alkyl, $C_1$-$C_4$ haloalkyl, or

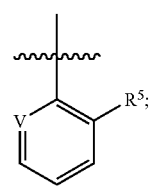

V is N; and
$R^5$ is H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio.

6. The compound of claim 5 wherein
$R^5$ is H, $C_1$-$C_4$ alkyl, $C_1$-$C_4$ haloalkyl, halogen or CN;
$R^6$ is H, $CH_3$, $CF_3$, $OCH_2CF_3$, $OCHF_2$ or halogen; and
$R^7$ is $CH_2CF_3$, $CHF_2$ or $CF_3$.

7. The compound of claim 6 wherein J substituted with $R^3$ and optionally substituted with $R^6$ is J-5; $R^5$ is Cl or Br; and $R^6$ is halogen, $OCH_2CF_3$, $OCHF_2$ or $CF_3$.

8. A composition for controlling an invertebrate pest comprising a biologically effective amount of a compound of claim 1 and at least one additional component selected from the group consisting of surfactants, solid diluents and liquid diluents.

9. The composition of claim 8 which further comprises at least one additional compound or agent for controlling an invertebrate pest.

* * * * *